(12) United States Patent
Ellmark et al.

(10) Patent No.: US 10,414,815 B2
(45) Date of Patent: Sep. 17, 2019

(54) SCFV ANTIBODY LIBRARY

(71) Applicant: ALLIGATOR BIOSCIENCE AB, Lund (SE)

(72) Inventors: Peter Ellmark, Lund (SE); Helena Persson, Jarfalla (SE)

(73) Assignee: ALLIGATOR BIOSCIENCE AB, Lund (SE)

( * ) Notice: Subject to any disclaimer, the term of this patent is extended or adjusted under 35 U.S.C. 154(b) by 131 days.

(21) Appl. No.: 15/115,313

(22) PCT Filed: Feb. 11, 2015

(86) PCT No.: PCT/EP2015/052893
§ 371 (c)(1),
(2) Date: Jul. 29, 2016

(87) PCT Pub. No.: WO2015/121314
PCT Pub. Date: Aug. 20, 2015

(65) Prior Publication Data
US 2017/0002061 A1    Jan. 5, 2017

(30) Foreign Application Priority Data
Feb. 14, 2014   (GB) .................. 1402631.4

(51) Int. Cl.
| | | |
|---|---|---|
| *C40B 40/10* | (2006.01) | |
| *C07K 16/00* | (2006.01) | |
| *C07K 16/18* | (2006.01) | |
| *C07K 16/28* | (2006.01) | |
| *C12N 15/10* | (2006.01) | |
| *G01N 33/68* | (2006.01) | |

(52) U.S. Cl.
CPC ............ *C07K 16/005* (2013.01); *C07K 16/18* (2013.01); *C07K 16/2878* (2013.01); *C12N 15/1037* (2013.01); *G01N 33/6854* (2013.01); *C07K 2317/21* (2013.01); *C07K 2317/56* (2013.01); *C07K 2317/565* (2013.01); *C07K 2317/622* (2013.01); *C07K 2317/92* (2013.01); *C40B 40/10* (2013.01)

(58) Field of Classification Search
None
See application file for complete search history.

(56) References Cited

FOREIGN PATENT DOCUMENTS

WO    2010/028791 A1    3/2010

OTHER PUBLICATIONS

Ponsel et al. (May 3, 2011) Molecules, Molecular Diversity Preservation vol. 16 pp. 3675 to 3700.*
Knappik et al. (Feb. 11, 2000) Journal of Molecular Biology vol. 296 pp. 57 to 86.*

(Continued)

*Primary Examiner* — Christian C Boesen
(74) *Attorney, Agent, or Firm* — Robert C. Netter, Jr.; Dann, Dorfman, Herrell & Skillman

(57) ABSTRACT

The invention provides libraries of antibody molecules, libraries of nucleic acids encoding antibody molecules, methods of producing said libraries, and methods of using said libraries to select an antibody which specifically binds to an antigen. The libraries of antibody molecules include a plurality of different antibody variable domains generated by creating diversity in the CDR regions.

7 Claims, 9 Drawing Sheets

Specification includes a Sequence Listing.

Summary of the three primer pools for VL CDR3
(K3-8a, K3-9a and K3-10a)

"3": Each triplet codon is independently selected to encode tyrosine, serine, glycine, alanine, phenylalanine, tryptophan, histidine, proline, valine, aspartate, asparagine, threonine or arginine. The overall frequency of a codon for each given amino acid in each available codon position is as follows: 25%Tyr, 15%Ser, 20%Gly, 5%Ala, 5%Phe, 5%Trp, 5%His, 5%Pro, 5%Val, 3%Asp, 3%Asn, 3%Thr, 1%Arg.

I = SEQ ID NO: 17, II = SEQ ID NO: 18

Library AL2 VL primers

(56) References Cited

OTHER PUBLICATIONS

Pini, Alesandro et al., "Desgian dn Use of a Phage Display Library", The Journal of Biological Chemistry, 273(34): 21769-21776 (1998).

Sidhu, Sachdev et al., "Phage-displayed Antibody Libraries of Synthetic Heavy Chain Complementarity Determining Regions", JMB, 338: 299-310 (2004).

Fellouse, Frederic A. et al., "Synthetic antibodies from a four-amino-acid code: A dominant role for tyrosine in antigen recognition", PNAS, 101(34): 12467-12472 (2004).

International Search Report and Written Opinion, dated Apr. 22, 2015, issued in corresponding International Application No. PCT/EP2015/052893.

* cited by examiner

FIGURE 1A
Library AL1 VH primers

Summary of the fifteen primer pools for VH CDR3
(H3-8, H3-9, H3-10, H3-11, H3-12, H3-13, H3-14, H3-15, H3-16, H3-17, H3-18, H3-19, H3-20, H3-21 and H3-22)

| I | | II |
|---|---|---|
| 3, 4, 5, 6, 7, 8, 9, 10, 11, 12, 13, 14, 15, 16 or 17 triplet codons independently selected as in "3" | | |

Summary of the primer pool for VH CDR1
(H1-1a)

| III | | IV |
|---|---|---|
| 4 triplet codons independently selected as in "1" | —ATG— | 1 triplet codon independently selected as in "1" |

Summary of the primer pool for VH CDR2
(H2-1a)

| V | | | | VI |
|---|---|---|---|---|
| 1 triplet codon independently selected as in "2" | —ATT— | 6 triplet codons independently selected as in "2" | —ACA— | 1 triplet codon independently selected as in "2" |

"1": Each triplet codon is independently selected to encode tyrosine, serine or glycine. The overall frequency of a codon for each given amino acid in each available codon position is equal.

"2": Each triplet codon is independently selected to encode tyrosine, serine or glycine. The overall frequency of a codon for each given amino acid in each available codon position is equal.

"3": Each triplet codon is independently selected to encode tyrosine, serine, glycine, alanine, phenylalanine, tryptophan, histidine, proline, valine, aspartate, asparagine, threonine or arginine. The overall frequency of a codon for each given amino acid in each available codon position is as follows: 25% Tyr, 15% Ser, 15% Gly, 5% Ala, 5% Phe, 10 % Trp, 5% His, 5% Pro, 5% Val, 3% Asp, 3% Asn, 3% Thr and 1% Arg.

I = SEQ ID NO: 11, II = SEQ ID NO: 12, III= SEQ ID NO: 7, IV = SEQ ID NO: 8, V= SEQ ID NO: 9, VI = SEQ ID NO:10

FIGURE 1B
Library AL1 VL primers

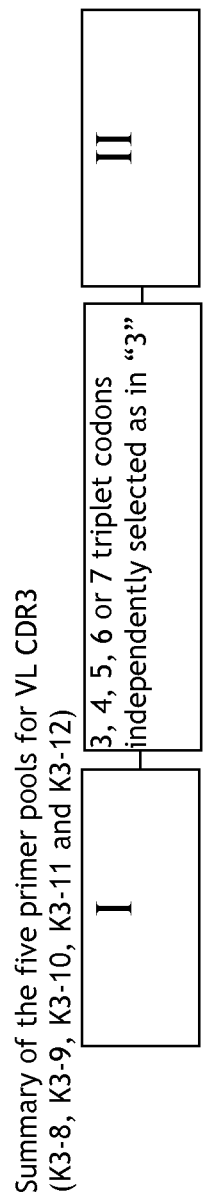

Summary of the five primer pools for VL CDR3 (K3-8, K3-9, K3-10, K3-11 and K3-12)

I 3, 4, 5, 6 or 7 triplet codons independently selected as in "3"

II

"3": Each triplet codon is independently selected to encode tyrosine, serine, glycine, alanine, phenylalanine, tryptophan, histidine, proline, valine, aspartate, asparagine, threonine or arginine. The overall frequency of a codon for each given amino acid in each available codon position is as follows: 25% Tyr, 15% Ser, 15% Gly, 5% Ala, 5% Phe, 10% Trp, 5% His, 5% Pro, 5% Val, 3% Asp, 3% Asn, 3% Thr and 1% Arg.

I = SEQ ID NO: 13, II = SEQ ID NO: 14

Library AL2 VH primers

FIGURE 1D
Library AL2 VL primers

Summary of the three primer pools for VL CDR3 (K3-8a, K3-9a and K3-10a)

I | 3, 4 or 5 triplet codons independently selected as in "3" | II

"3": Each triplet codon is independently selected to encode tyrosine, serine, glycine, alanine, phenylalanine, tryptophan, histidine, proline, valine, aspartate, asparagine, threonine or arginine. The overall frequency of a codon for each given amino acid in each available codon position is as follows: 25%Tyr, 15%Ser, 20%Gly, 5%Ala, 5%Phe, 5%Trp, 5%His, 5%Pro, 5%Val, 3%Asp, 3%Asn, 3%Thr, 1%Arg.

I = SEQ ID NO: 17, II = SEQ ID NO: 18

FIGURE 1E
Library AL3 VH primers

Summary of the ten primer pools for VH CDR3
(H3-8b, H3-9b, H3-10b, H3-11b, H3-12b, H3-13b, H3-14b, H3-15b, H3-16b and H3-17b)

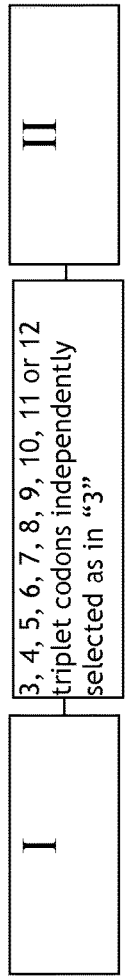

| I | II |
|---|---|
| 3, 4, 5, 6, 7, 8, 9, 10, 11 or 12 triplet codons independently selected as in "3" | |

Summary of the primer pool for VH CDR1
(H1-1a)

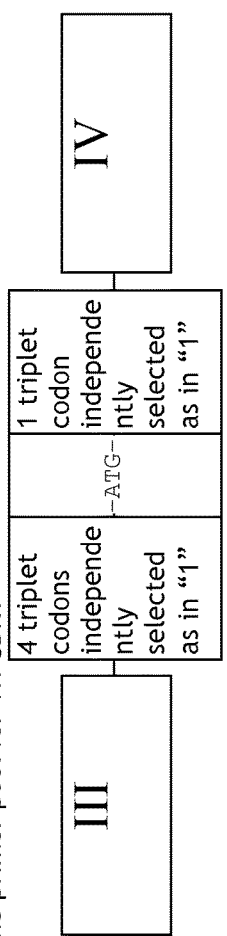

| III | | IV |
|---|---|---|
| 4 triplet codons independently selected as in "1" | –ATG– | 1 triplet codon independently selected as in "1" |

Summary of the primer pool for VH CDR2
(H2-1a)

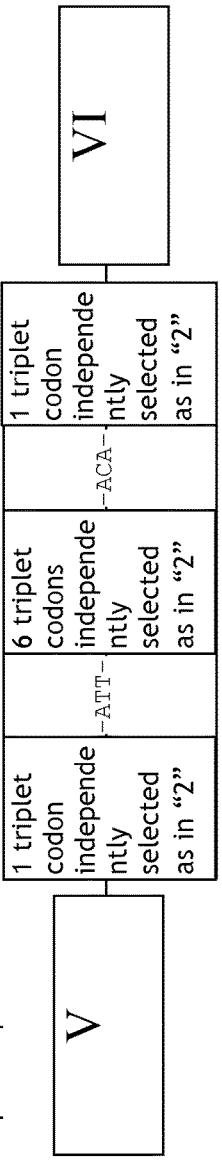

| V | | | | VI |
|---|---|---|---|---|
| 1 triplet codon independently selected as in "2" | –ATT– | 6 triplet codons independently selected as in "2" | –ACA– | 1 triplet codon independently selected as in "2" |

"1": Each triplet codon is independently selected to encode tyrosine, serine or glycine. The overall frequency of a codon for each given amino acid in each available codon position is equal.

"2": Each triplet codon is independently selected to encode tyrosine, serine or glycine. The overall frequency of a codon for each given amino acid in each available codon position is equal.

"3": Each triplet codon is independently selected to encode tyrosine, serine, glycine, alanine, phenylalanine, tryptophan, histidine, proline, valine, aspartate, asparagine, threonine or arginine. The overall frequency of a codon for each given amino acid in each available codon position is as follows: 20%Tyr, 15%Gly, 15%Ser, 5%Trp, 5%Ala, 5%Phe, 15%His, 5%Pro, 5%Val, 3%Asp, 3%Asn, 3%Thr, 1%Arg.

I = SEQ ID NO: 15, II = SEQ ID NO: 16, III= SEQ ID NO: 7, IV = SEQ ID NO: 8, V= SEQ ID NO: 9, VI = SEQ ID NO:10

Library AL3 VL primers

SEQUENCE LISTING

<160> NUMBER OF SEQ ID NOS: 26

<210> SEQ ID NO 1
<211> LENGTH: 98
<212> TYPE: PRT
<213> ORGANISM: Homo sapiens

<400> SEQUENCE: 1

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 2
<211> LENGTH: 14
<212> TYPE: PRT
<213> ORGANISM: Homo sapiens

<400> SEQUENCE: 2

```
Phe Asp Tyr Trp Gly Gln Gly Thr Leu Val Thr Val Ser Ser
1               5                   10
```

<210> SEQ ID NO 3
<211> LENGTH: 112
<212> TYPE: PRT
<213> ORGANISM: Homo sapiens

<400> SEQUENCE: 3

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Asp Tyr Trp Gly Gln Gly Thr Leu Val Thr Val Ser Ser
            100                 105                 110
```

<210> SEQ ID NO 4
<211> LENGTH: 95
<212> TYPE: PRT
<213> ORGANISM: Homo sapiens

<400> SEQUENCE: 4

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro
                85                  90                  95
```

<210> SEQ ID NO 5
<211> LENGTH: 12
<212> TYPE: PRT
<213> ORGANISM: Homo sapiens

<400> SEQUENCE: 5

```
Tyr Thr Phe Gly Gln Gly Thr Lys Leu Glu Ile Lys
1               5                   10
```

<210> SEQ ID NO 6
<211> LENGTH: 107
<212> TYPE: PRT
<213> ORGANISM: Homo sapiens

<400> SEQUENCE: 6

```
Asp Ile Gln Met Thr Gln Ser Pro Ser Ser Leu Ser Ala Ser Val Gly
```

```
              1               5                  10                 15
Asp Arg Val Thr Ile Thr Cys Arg Ala Ser Gln Ser Ile Ser Ser Tyr
                    20                  25                 30

Leu Asn Trp Tyr Gln Gln Lys Pro Gly Lys Ala Pro Lys Leu Leu Ile
            35                  40                 45

Tyr Ala Ala Ser Ser Leu Gln Ser Gly Val Pro Ser Arg Phe Ser Gly
        50                  55                 60

Ser Gly Ser Gly Thr Asp Phe Thr Leu Thr Ile Ser Ser Leu Gln Pro
65                  70                  75                 80

Glu Asp Phe Ala Thr Tyr Tyr Cys Gln Gln Ser Tyr Ser Thr Pro Tyr
                    85                  90                 95

Thr Phe Gly Gln Gly Thr Lys Leu Glu Ile Lys
                100                 105
```

<210> SEQ ID NO 7
<211> LENGTH: 18
<212> TYPE: DNA
<213> ORGANISM: artificial
<220> FEATURE:
<223> OTHER INFORMATION: primer

<400> SEQUENCE: 7
gccagcggat tcaccttt                                               18

<210> SEQ ID NO 8
<211> LENGTH: 18
<212> TYPE: DNA
<213> ORGANISM: artificial
<220> FEATURE:
<223> OTHER INFORMATION: primer

<400> SEQUENCE: 8
tgggtccgcc aggctcca                                               18

<210> SEQ ID NO 9
<211> LENGTH: 18
<212> TYPE: DNA
<213> ORGANISM: artificial
<220> FEATURE:
<223> OTHER INFORMATION: primer

<400> SEQUENCE: 9
gggctggagt gggtctca                                               18

<210> SEQ ID NO 10
<211> LENGTH: 18
<212> TYPE: DNA
<213> ORGANISM: artificial
<220> FEATURE:
<223> OTHER INFORMATION: primer

<400> SEQUENCE: 10
tatgcagact ccgtgaag                                               18

<210> SEQ ID NO 11
<211> LENGTH: 18
<212> TYPE: DNA
<213> ORGANISM: artificial
<220> FEATURE:
<223> OTHER INFORMATION: primer

<400> SEQUENCE: 11
gtatattatt gtgcgcgc                                               18

```
<210> SEQ ID NO 12
<211> LENGTH: 21
<212> TYPE: DNA
<213> ORGANISM: artificial
<220> FEATURE:
<223> OTHER INFORMATION: primer

<400> SEQUENCE: 12
wtkgactatt ggggccaggg a                                              21

<210> SEQ ID NO 13
<211> LENGTH: 18
<212> TYPE: DNA
<213> ORGANISM: artificial
<220> FEATURE:
<223> OTHER INFORMATION: primer

<400> SEQUENCE: 13
acttattact gtcaacag                                                  18

<210> SEQ ID NO 14
<211> LENGTH: 24
<212> TYPE: DNA
<213> ORGANISM: artificial
<220> FEATURE:
<223> OTHER INFORMATION: primer

<400> SEQUENCE: 14
cygyhcactt ttggccaggg gacc                                           24

<210> SEQ ID NO 15
<211> LENGTH: 20
<212> TYPE: DNA
<213> ORGANISM: artificial
<220> FEATURE:
<223> OTHER INFORMATION: primer

<400> SEQUENCE: 15
ctgtatatta ttgtgcgcgc                                                20

<210> SEQ ID NO 16
<211> LENGTH: 19
<212> TYPE: DNA
<213> ORGANISM: artificial
<220> FEATURE:
<223> OTHER INFORMATION: primer

<400> SEQUENCE: 16
wtkgactatt ggggccagg                                                 19

<210> SEQ ID NO 17
<211> LENGTH: 21
<212> TYPE: DNA
<213> ORGANISM: artificial
<220> FEATURE:
<223> OTHER INFORMATION: primer

<400> SEQUENCE: 17
gcaacttatt actgtcaaca g                                              21

<210> SEQ ID NO 18
<211> LENGTH: 23
<212> TYPE: DNA
<213> ORGANISM: artificial
<220> FEATURE:
```

```
<223> OTHER INFORMATION: primer

<400> SEQUENCE: 18
cygyhcactt ttggccaggg gac                                              23

<210> SEQ ID NO 19
<211> LENGTH: 18
<212> TYPE: DNA
<213> ORGANISM: artificial
<220> FEATURE:
<223> OTHER INFORMATION: primer

<400> SEQUENCE: 19
acttgccggg caagtcag                                                    18

<210> SEQ ID NO 20
<211> LENGTH: 19
<212> TYPE: DNA
<213> ORGANISM: artificial
<220> FEATURE:
<223> OTHER INFORMATION: primer

<400> SEQUENCE: 20
tatttaaatt ggtatcagc                                                   19

<210> SEQ ID NO 21
<211> LENGTH: 19
<212> TYPE: DNA
<213> ORGANISM: artificial
<220> FEATURE:
<223> OTHER INFORMATION: primer

<400> SEQUENCE: 21
ccctaagctc ctgatctat                                                   19

<210> SEQ ID NO 22
<211> LENGTH: 18
<212> TYPE: DNA
<213> ORGANISM: artificial
<220> FEATURE:
<223> OTHER INFORMATION: primer

<400> SEQUENCE: 22
gcatccagtt tgcaaagt                                                    18

<210> SEQ ID NO 23
<211> LENGTH: 15
<212> TYPE: PRT
<213> ORGANISM: artificial
<220> FEATURE:
<223> OTHER INFORMATION: Linker sequence

<400> SEQUENCE: 23

Gly Gly Gly Gly Ser Gly Gly Gly Gly Ser Gly Gly Gly Gly Ser
1               5                   10                  15

<210> SEQ ID NO 24
<211> LENGTH: 8
<212> TYPE: PRT
<213> ORGANISM: artificial
<220> FEATURE:
<223> OTHER INFORMATION: FLAG-tag sequence

<400> SEQUENCE: 24

Asp Tyr Lys Asp Asp Asp Asp Lys
1               5
```

<210> SEQ ID NO 25
<211> LENGTH: 711
<212> TYPE: DNA
<213> ORGANISM: artificial
<220> FEATURE:
<223> OTHER INFORMATION: template nucleic acid sequence for library

<400> SEQUENCE: 25

| | |
|---|---|
| gaggtgcagc tgttggagag cggggggaggc ttggtacagc ctggggggtc cctgcgcctc | 60 |
| tcctgtgcag ccagcggatt cacctttagc agctatgcca tgagctgggt ccgccaggct | 120 |
| ccagggaagg gctggagtg gtctcagct attagtggta gtggtggtag cacatactat | 180 |
| gcagactccg tgaagggccg gttcaccatc tcccgtgaca attccaagaa cacgctgtat | 240 |
| ctgcaaatga cagcctgcg tgccgaggac acggctgtat attattgtgc gcgctaataa | 300 |
| taatactttg actattgggg ccagggaacc ctggtcaccg tctcctcagg tggaggcggt | 360 |
| tcaggcggag gtggatccgg cggtggcgga tcggacatcc agatgaccca gtctccatcc | 420 |
| tccctgagcg catctgtagg agaccgcgtc accatcactt gccgggcaag tcagagcatt | 480 |
| agcagctatt taaattggta tcagcagaaa ccagggaaag cccctaagct cctgatctat | 540 |
| gctgcatcca gtttgcaaag tggggtccca tcacgtttca gtggcagtgg aagcgggaca | 600 |
| gatttcactc tcaccatcag cagtctgcaa cctgaagatt ttgcaactta ttactgtcaa | 660 |
| cagagttaat aataatacac ttttggccag gggaccaagc tggagatcaa a | 711 |

<210> SEQ ID NO 26
<211> LENGTH: 723
<212> TYPE: DNA
<213> ORGANISM: artificial
<220> FEATURE:
<223> OTHER INFORMATION: template nucleic acid sequence for library

<400> SEQUENCE: 26

| | |
|---|---|
| gaggtgcagc tgttggagag cggggggaggc ttggtacagc ctggggggtc cctgcgcctc | 60 |
| tcctgtgcag ccagcggatt cacctttagc agctatgcca tgagctgggt ccgccaggct | 120 |
| ccagggaagg gctggagtg gtctcagct attagtggta gtggtggtag cacatactat | 180 |
| gcagactccg tgaagggccg gttcaccatc tcccgtgaca attccaagaa cacgctgtat | 240 |
| ctgcaaatga cagcctgcg tgccgaggac acggctgtat attattgtgc gcgctaatga | 300 |
| taatgactcg agtactttga ctattggggc cagggaaccc tggtcaccgt ctcctcaggt | 360 |
| ggaggcggtt caggcggagg tggatccggc ggtggcggat cggacatcca gatgacccag | 420 |
| tctccatcct ccctgagcgc atctgtagga gaccgcgtca ccatcacttg ccgggcaagt | 480 |
| cagagcatta gcagctattt aaattggtat cagcagaaac cagggaaagc ccctaagctc | 540 |
| ctgatctatg ctgcatccag tttgcaaagt ggggtcccat cacgtttcag tggcagtgga | 600 |
| agcgggacag atttcactct caccatcagc agtctgcaac ctgaagattt tgcaacttat | 660 |
| tactgtcaac agagttacag tacccttat acttttggcc aggggaccaa gctggagatc | 720 |
| aaa | 723 |

SCFV ANTIBODY LIBRARY

This application is a § 371 application of PCT/EP2015/052893, filed Feb. 11, 2015, which in turn claims priority to GB Application 1402631.4, filed Feb. 14, 2014. The entire disclosure of each of the foregoing applications is incorporated by reference herein.

FIELD OF THE INVENTION

The invention provides libraries of antibody molecules, libraries of nucleic acids encoding antibody molecules, methods of producing said libraries, and methods of using said libraries to select an antibody which specifically binds to an antigen. The libraries of antibody molecules include a plurality of different antibody variable domains generated by creating diversity in the CDR regions.

BACKGROUND OF THE INVENTION

Monoclonal antibodies have proven useful as reagents for research, and also as clinical agents for both therapy and diagnosis. Human monoclonal antibodies are particularly useful for this purpose. The introduction of phage display technology has provided a tool for the generation of human antibodies which circumvents the limitations of earlier antibody generating technologies. Phage display technology made it possible to generate large antibody repertoires within E. coli. The antibody repertoire is expressed in the bacteria, and subsequently exposed to a selective pressure to thereby obtain desired antibody characteristics. Several other in vitro antibody display methods, such as ribosomal display and bacterial, yeast and mammalian cell surface display, have also emerged and also allow the production of diverse antibody libraries.

The antigen-binding site of an antibody typically comprises a heavy chain variable domain (VH) and a light chain variable domain (VL). The majority of the diversity in the antigen specificity of an antibody is provided by six loops or regions, known as the complementary determining regions (CDRs), with three CDRs present in the heavy chain variable domain (the VH CDRs 1, 2 and 3) and three CDRs present in the light chain variable domain (the VL CDRs 1, 2 and 3). All six CDRs of an antibody, supported by more conserved framework regions, constitute a functional antigen-binding site. VH CDR3 and VL CDR3 are naturally the most diverse and are therefore considered to be the most important for antigen recognition. The VH and VL CDRs 1 and 2 are considered to have a more subordinate role in antigen recognition.

A synthetic antibody library comprises designed diversity primarily in the CDRs, which is introduced by controlled synthesis of the genes encoding the variable domains. The earliest synthetic antibody libraries were semi-synthetic, comprising CDRs from natural sources with designed variations introduced in parts. Hoogenboom and Winter used in their design of a semi-synthetic scFV antibody library a variety of different framework genes in combination with diversity generated by randomization of positions in the VH CDR3 region (Hoogenboom and Winter, J Mol Biol. 1992 Sep. 20; 227(2):381-8). The synthetic design was expanded to length variations of CDR3. Residues in VL CDR3 as well as in the VH CDR3 were randomized. The added features of the synthetic design generated antibody libraries of increased size.

A fully synthetic library design was demonstrated by Sidhu et al., who applied a restricted design to the CDRs (Sidhu et al., J. Mol. Biol. 2007, 373, 924-940). The diversity was restricted to the binary code of tyrosine and serine in VH CDR1 and VH CDR2. The VL CDR3 was restricted to the binary code of tyrosine and serine while the VH CDR3 was allowed chemical complexity. The amino acid composition of VH CDR3 was biased for tyrosine, serine, and glycine, while allowing all other amino acids (19) except for cysteine which was excluded. The restricted design produced highly functional phage-displayed libraries.

The demand for novel high affinity antibodies for clinical uses remains high. Thus, there remains a need for diverse libraries of antibody molecules. This need is met by the present invention, which also provides other advantages.

SUMMARY OF THE INVENTION

The size and design of an antibody library are factors determining the quality of its performance in isolating high affinity binders to a variety of antigens. The preferred size for an antibody library of the invention is typically greater than $1 \times 10^{10}$ different molecules. The present invention relates to advances in the design of antibody libraries, which result in libraries with certain advantages relative to existing libraries.

The libraries of the present invention comprise deliberately designed restrictions in the permitted length and amino acid composition of the CDRs. This provides several advantages, including that target-specific antibody molecules selected from the libraries are stable, of high affinity and are produced in high yield. In addition, fewer of the antibody molecules in the libraries exhibit non-specific binding. A library that contains fewer antibody molecules exhibiting non-specific binding is advantageous for numerous reasons. The purpose of a library is primarily to enable the selection of target-specific antibodies. At the initial selection stage, there are typically only a few copies of each unique antibody molecule present. Target-specific binders must compete with all non-specific binders. If the number of antibody molecules exhibiting non-specific binding is low, the chance of successfully isolating clinically relevant molecules is higher. Further, a lower number of non-specific binders enables faster and cheaper selection and screening protocols, involving fewer negative control assays and negative selections. These advantages are particularly beneficial when the library of the invention is in the form of a phage display library or similar, since multiple rounds of selection and screening are typically required to select and isolate a clinically relevant clone.

In one aspect, the present invention provides a library of antibody molecules, designated library category AL2, in which the VH CDR3 and VL CDR3 are of restricted length and contain a low frequency of tryptophan residues. This contributes to production of high affinity antibody molecules which can be expressed in high yields. Thus, the present invention provides:

A library of antibody molecules, wherein each antibody molecule comprises:
  (i) a VH domain consisting of VH CDR1, CDR2, CDR3 and framework regions, wherein the VH domain amino acid sequence is a human germline antibody heavy chain sequence in which:
     (a) each solvent accessible residue in VH CDR1 and CDR2 is independently substituted with an amino acid selected from tyrosine, serine and glycine, wherein each of tyrosine, serine and glycine is equally preferred;

(b) the VH CDR3 consists of between 8 and 17 amino acids
(c) each solvent accessible residue in VH CDR3 is independently substituted with an amino acid selected from tyrosine, serine, glycine, alanine, phenylalanine, tryptophan, histidine, proline, valine, aspartate, asparagines, threonine and arginine in the following relative order of preference: 25% Tyr, 15% Ser, 20% Gly, 5% Ala, 5% Phe, 5% Trp, 5% His, 5% Pro, 5% Val, 3% Asp, 3% Asn, 3% Thr, 1% Arg;
(d) the residue at position 115 of VH CDR3 is independently substituted with an amino acid selected from phenylalanine, isoleucine, leucine and methionine, wherein each of phenylalanine, isoleucine, leucine and methionine is equally preferred;
and
(ii) a VL domain consisting of VL CDR1, CDR2, CDR3 and framework regions, wherein the VL domain amino acid sequence is a human germline antibody light chain sequence in which:
(a) the VL CDR3 consists of between 8 and 12 amino acids;
(b) each solvent accessible residue in VL CDR3 is independently substituted with an amino acid selected from tyrosine, serine, glycine, alanine, phenylalanine, tryptophan, histidine, proline, valine, aspartate, asparagines, threonine and arginine in the following relative order of preference: 25% Tyr, 15% Ser, 20% Gly, 5% Ala, 5% Phe, 5% Trp, 5% His, 5% Pro, 5% Val, 3% Asp, 3% Asn, 3% Thr, 1% Arg;
(c) the residue at position 115 in VL CDR3 is independently substituted with an amino acid selected from phenylalanine and leucine, wherein each of phenylalanine and leucine is equally preferred;
(d) the residue at position 116 in VL CDR3 is independently substituted with an amino acid selected from histidine, proline, leucine, tyrosine, serine and phenylalanine, wherein each of histidine, proline, leucine, tyrosine, serine and phenylalanine is equally preferred.

The present invention also provides a library of antibody molecules, designated library category AL3, in which the amino acid composition of the CDRs is selected to favour antibodies which are stable and display high affinity and/or improved tumour penetration at low pH, since the pH in a tumour microenvironment is more acidic than that of healthy tissues. Thus, in this library, the VH CDR3 contains a high frequency of histidine residues. This leads to improved stability and high affinity in low pH environments. In addition, the VH CDR3 and VL CDR3 are of restricted length and contain a low frequency of tryptophan residues. This leads to production of high affinity antibodies in high yields. Thus, the present invention also provides:

A library of antibody molecules, wherein each antibody molecule comprises:
(i) a VH domain consisting of VH CDR1, CDR2, CDR3 and framework regions, wherein the VH domain amino acid sequence is a human germline antibody heavy chain sequence in which:
(a) each solvent accessible residue in VH CDR1 and CDR2 is independently substituted with an amino acid selected from tyrosine, serine and glycine, wherein each of tyrosine, serine and glycine is equally preferred;
(b) the VH CDR3 consists of between 8 and 17 amino acids
(c) each solvent accessible residue in VH CDR3 is independently substituted with an amino acid selected from tyrosine, glycine, serine, tryptophan, alanine, phenylalanine, histidine, proline, valine, aspartate, asparagines, threonine and arginine, in the following relative order of preference 20% Tyr, 15% Gly, 15% Ser, 5% Trp, 5% Ala, 5% Phe, 15% His, 5% Pro, 5% Val, 3% Asp, 3% Asn, 3% Thr, 1% Arg.
(d) the residue at position 115 of VH CDR3 is independently substituted with an amino acid selected from phenylalanine, isoleucine, leucine and methionine, wherein each of phenylalanine, isoleucine, leucine and methionine is equally preferred.
and
(ii) a VL domain consisting of VL CDR1, CDR2, CDR3 and framework regions, wherein the VL domain amino acid sequence is a human germline antibody light chain sequence in which:
(a) the residues at positions 28 and 37 in VL CDR1 are each independently substituted with an amino acid selected from tyrosine, serine, glycine, asparagine and alanine, wherein each of tyrosine, serine, glycine, asparagine and alanine is equally preferred;
(b) the residue at position 36 in VL CDR1 is independently substituted with an amino acid selected from serine and arginine, wherein each of serine and arginine is equally preferred;
(c) the residue in position 56 of VL CDR2 is independently substituted with an amino acid selected from tyrosine, serine, glycine, asparagine and alanine, wherein each of tyrosine, serine, glycine, asparagine and alanine is equally preferred;
(d) the VL CDR3 consists of between 8 and 12 amino acids
(e) each solvent accessible residue in VL CDR3 is independently substituted with an amino acid selected from tyrosine, glycine, serine, tryptophan, alanine, phenylalanine, histidine, proline, valine, aspartate, asparagines, threonine and arginine, in the following relative order of preference: 25% Tyr, 20% Gly, 15% Ser, 5% Trp, 5% Ala, 5% Phe, 5% His, 5% Pro, 5% Val, 3% Asp, 3% Asn, 3% Thr, 1% Arg;
(f) the residue at position 115 in VL CDR3 is independently substituted with an amino acid selected from phenylalanine and leucine, wherein each of phenylalanine and leucine is equally preferred;
(g) the residue at position 116 in VL CDR3 is independently substituted with an amino acid selected from histidine, proline, leucine, tyrosine, serine and phenylalanine, wherein each of histidine, proline, leucine, tyrosine, serine and phenylalanine is equally preferred.

The present invention also provides a library of antibody molecules, in which a proportion of the antibody molecules are each as defined in category AL2 and a proportion of the antibody molecules are each as defined in category AL3, preferably wherein said proportions are equal.

The present invention also provides a library of antibody molecules, designated library category AL1. Thus the present invention provides:

A library of antibody molecules, wherein each antibody molecule comprises
(i) a VH domain consisting of VH CDR1, CDR2, CDR3 and framework regions, wherein the VH domain amino acid sequence is a human germline antibody heavy chain sequence in which:

(a) each solvent accessible residue in VH CDR1 and CDR2 is independently substituted with an amino acid selected from tyrosine, serine and glycine, wherein each of tyrosine, serine and glycine is equally preferred;
(b) the VH CDR3 consists of between 8 and 22 amino acids
(c) each solvent accessible residue in VH CDR3 is independently substituted with an amino acid selected from tyrosine, serine, glycine, alanine, phenylalanine, tryptophan, histidine, proline, valine, aspartate, asparagine, threonine and arginine in the following relative order of preference: 25% Tyr, 15% Ser, 15% Gly, 5% Ala, 5% Phe, 10% Trp, 5% His, 5% Pro, 5% Val, 3% Asp, 3% Asn, 3% Thr and 1% Arg;
(d) the residue at position 115 of VH CDR3 is independently substituted with an amino acid selected from phenylalanine, isoleucine, leucine and methionine, wherein each of phenylalanine, isoleucine, leucine and methionine is equally preferred;
and
(ii) a VL domain consisting of VL CDR1, CDR2, CDR3 and framework regions, wherein the VL domain amino acid sequence is a human germline antibody light chain sequence in which:
(a) the VL CDR3 consists of between 8 and 12 amino acids;
(b) each solvent accessible residue in VL CDR3 is independently substituted with an amino acid selected from tyrosine, serine, glycine, alanine, phenylalanine, tryptophan, histidine, proline, valine, aspartate, asparagines, threonine and arginine in the following relative order of preference: 25% Tyr, 15% Ser, 15% Gly, 5% Ala, 5% Phe, 10% Trp, 5% His, 5% Pro, 5% Val, 3% Asp, 3% Asn, 3% Thr and 1% Arg;
(c) the residue at position 115 in VL CDR3 is independently substituted with an amino acid selected from phenylalanine and leucine, wherein each of phenylalanine and leucine is equally preferred;
(d) the residue at position 116 in VL CDR3 is independently substituted with an amino acid selected from histidine, proline, leucine, tyrosine, serine and phenylalanine, wherein each of histidine, proline, leucine, tyrosine, serine and phenylalanine is equally preferred.

The present invention also provides a library of nucleic acid molecules which encodes a library of antibody molecules according to the invention, wherein each nucleic acid molecule in the library comprises a sequence which encodes at least one antibody molecule.

The present invention also provides a method of producing a library of antibody molecules, comprising:
(i) preparing a population of bacteriophage or phagemid vectors containing a library of nucleic acid molecules according to the invention; and
(ii) infecting a population of bacterial cells with said population of vectors under conditions which permit phage reproduction, optionally wherein said cells are *E. coli*.

The present invention also provides a method of selecting an antibody molecule that binds to an antigen comprising:
(i) providing a library of antibody molecules according to the invention;
(ii) contacting said library with said antigen;
(iii) selecting an antibody molecule which binds to the antigen.

The present invention also provides the use of a library according to the invention for screening for an antibody molecule that binds to an antigen.

The present invention also provides for an antibody molecule, preferably a human IgG antibody molecule, which comprises the VH and VL domain sequences of an antibody molecule selected in accordance with a method of the invention. Such an antibody may be formulated in a composition, which optionally comprises a pharmaceutically acceptable diluent or carrier.

BRIEF DESCRIPTION OF THE SEQUENCES

Figure 1C:
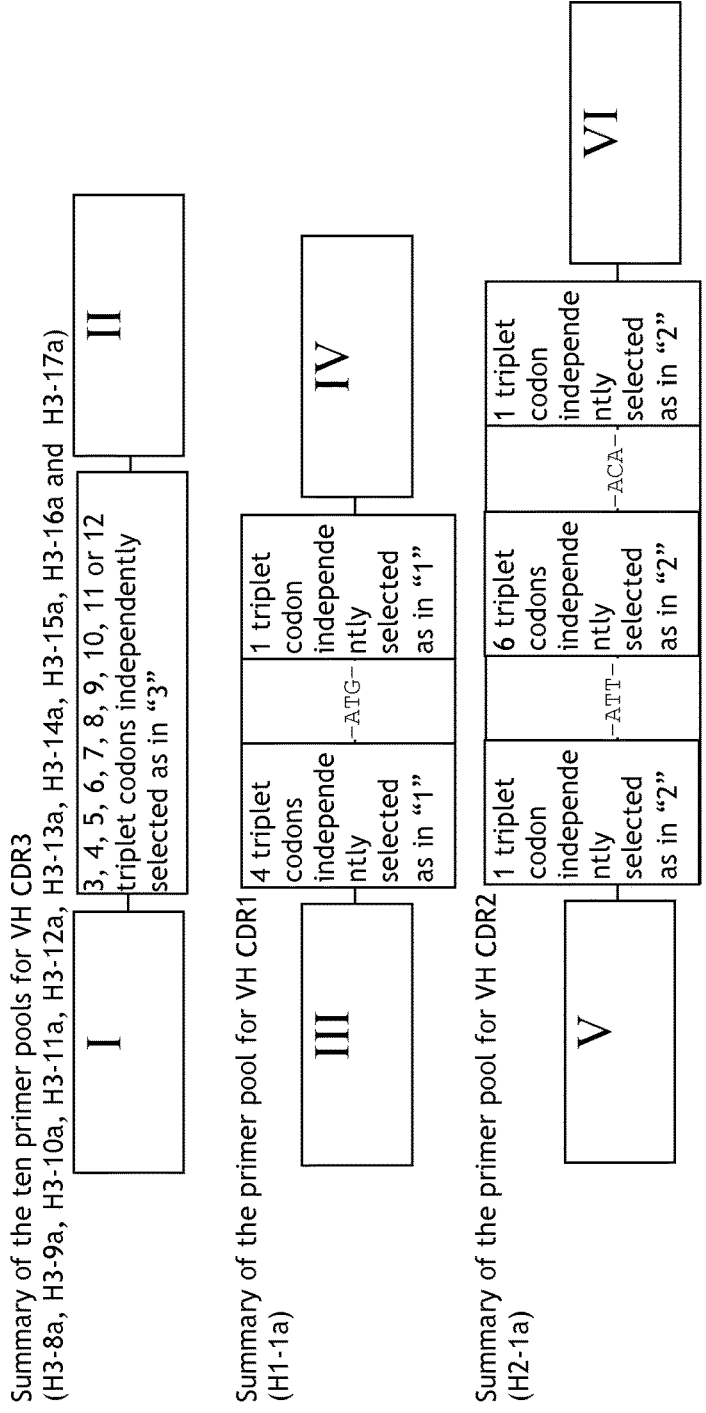
FIG. 1 summarises mutagenic primer pools which may be used to generate libraries according to the invention.
Figure 1F:
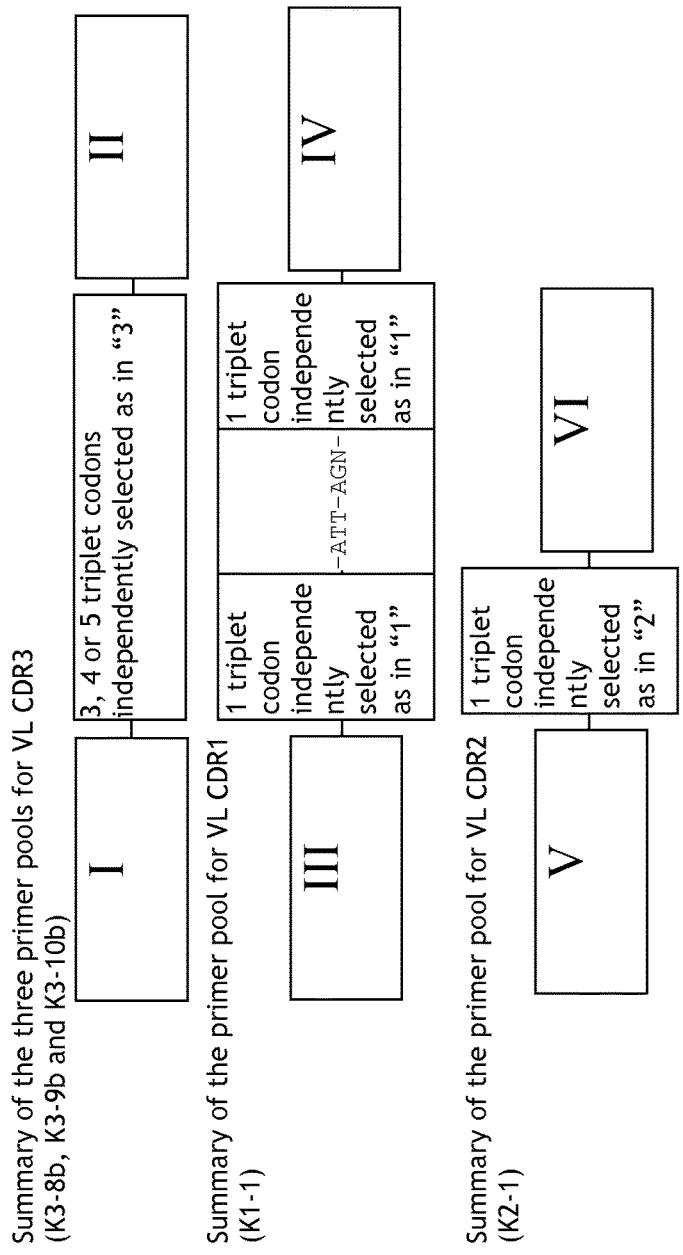

SEQ ID NO: 1: human germline antibody heavy chain amino acid sequence IgHV3-23;
SEQ ID NO: 2: human germline antibody heavy chain amino acid sequence of Jµ region 00256;
SEQ ID NO: 3: antibody heavy chain template amino acid sequence consisting of SEQ ID NOs: 1 and 2;
SEQ ID NO: 4: human germline antibody light chain amino acid sequence IgκV1-39;
SEQ ID NO: 5: human germline antibody light chain amino acid sequence of Jκ delta region 00242;
SEQ ID NO: 6: antibody light chain template amino acid sequence consisting of SEQ ID NOs: 4 and 5
SEQ ID NOs: 7 to 22: flanking sequences used to produce mutagenic primers of the invention, summarized in FIGS. 1A-F;
SEQ ID NO: 23: linker amino acid sequence;
SEQ ID NO: 24: FLAG-tag amino acid sequence.
SEQ ID NO: 25: Template nucleic acid sequence for library AL1
SEQ ID NO: 26: Template nucleic acid sequence for libraries AL2 & AL3

DETAILED DESCRIPTION OF THE INVENTION

Library of Antibody Molecules

The present invention is concerned with a library of antibody molecules, wherein each antibody molecule comprises a VH domain and a VL domain. Each antibody molecule may be an scFv molecule, in which the VH and VL domains are joined by a linker. Said linker may consist of the sequence GGGGSGGGGSGGGGS (SEQ ID NO: 23). Alternatively each antibody molecule may be an antibody fragment such as a Fab or F(ab')$_2$ fragment, or may be a complete IgG molecule. Each antibody molecule may optionally additionally comprise other amino acid sequences, such as an affinity tag to facilitate isolation of the antibody molecule. Suitable affinity tags include those which are known in the art, such as the FLAG-tag sequence (DYKDDDDK; SEQ ID NO: 24), streptavidin, or a His-tag sequence. Each antibody molecule may be present as a fusion protein with a coat protein of a bacteriophage, such that the library is a so-called "phage display" library.

"Phage display" is a well known laboratory technique, in which foreign protein are expressed on the surface of phage particles (see for example Antibody Engineering, Volume 1, Second edition, 2010, page 151-164). The most common bacteriophages used in phage display are M13 and fd filamentous phage, though T4, T7, and λ phage have also been used. The phages carry within them a nucleotide sequence encoding the expressed protein, and hence there is a direct link between phage genotype and phenotype. This link between the genotype and the phenotype in the phage format enables generation, selection and screening of large molecular libraries. Antibody phage display libraries are frequently based on fusion of scFvs (Fab and other antibody fragments have also been employed) to a coat protein of a bacteriophage. Coat protein pIII of the filamentous phage M13 is commonly used. Selection of a particular antibody molecule from an antibody phage display library typically involves several rounds of selection against one or several targets, either in solution or immobilized to beads or a surface, where the phage output from each selection round is amplified prior to the following selection round. The stringency of the selections are generally increased for each selection step to enrich for binders with high affinity and specificity.

Library Diversity

The diversity of the antibody molecules in a library of the invention derives from differences in the VH and VL domains. Each VH domain comprises three complementarity determining regions, VH CDRs 1, 2 and 3, separated by framework regions. Each VH domain comprises or consists of a human germline antibody heavy chain sequence in which substitutions have been made at certain positions within one or more of the CDRs. The length of one or more VH CDRs in each antibody molecule is fixed within a desired range. Each VL domain also comprises three complementarity determining regions, VL CDRs 1, 2 and 3, separated by framework regions. Each VL domain comprises or consists of a human germline antibody light chain sequence in which substitutions have been made at certain positions within one or more of the CDRs. The length of one or more VL CDRs in each antibody molecule is fixed within a desired range.

The human germline sequences are preferably selected as a pair, that is one heavy chain sequence and one light chain sequence. In this context, heavy chain and light chain sequences are typically selected which, when combined, result in antibodies that are stable and expressed at high yields.

A preferred human germline antibody heavy chain sequence comprises the IgHV3-23 sequence (SEQ ID NO: 1). A particularly preferred human germline antibody heavy chain sequence comprises the IgHV3-23 sequence linked to the Jµ region 00256 sequence (SEQ ID NO: 2). SEQ ID NO: 3 shows the IgHV3-23 sequence and Jµ region 00256 sequence arranged as a single contiguous sequence. This sequence can be considered the starting template for the VH domains of libraries of the invention, into which diversity is introduced.

A preferred human germline antibody light chain sequence comprises the Igκ1-39 sequence (SEQ ID NO: 4). A particularly preferred human germline antibody heavy chain sequence comprises the IgκV1-39 sequence linked to Jκ delta region 00242 sequence (SEQ ID NO: 5). SEQ ID NO: 6 shows the IgκV1-39 sequence and Jκ delta region 00242 sequence arranged as a single contiguous sequence. This sequence can be considered the starting template for the VL domains of libraries of the invention, into which diversity is introduced.

| Description | Amino acid sequence | SEQ ID: |
|---|---|---|
| IGHV3-23 | EVQLLESGGGLVQPGGSLRLSCAASGFTFSSYAMSWVRQAPGKGLEWVSAISGSGGST YYADSVKGRFTISRDNSKNTLYLQMNSLRAEDTAVYYCAR | 1 |
| Jµ0256 | FDYWGQGTLVTVSS | 2 |
| VH starting template | EVQLLESGGGLVQPGGSLRLSCAASGFTFSSYAMSWVRQAPGKGLEWVSAISGSGGST YYADSVKGRFTISRDNSKNTLYLQMNSLRAEDTAVYYCARFDYWGQGTLVTVSS | 3 |
| IGKV1-39 | DIQMTQSPSSLSASVGDRVTITCRASQSISSYLNWYQQKPGKAPKLLIYAASSLQSGV PSRFSGSGSGTDFTLTISSLQPEDFATYYCQQSYSTP | 4 |
| Jκ0242 | YTFGQGTKLEIK | 5 |
| VL starting template | DIQMTQSPSSLSASVGDRVTITCRASQSISSYLNWYQQKPGKAPKLLIYAASSLQSGV PSRFSGSGSGTDFTLTISSLQPEDFATYYCQQSYSTPYTFGQGTKLEIK | 6 |

All numbering of amino acid positions within antibody molecules as used herein is in accordance with the IMGT numbering system (www.imgt.org). The term "substitution" in the context of a numbered amino acid position in an antibody molecule herein may mean (i) the replacement in a first sequence (such as a wild type sequence) of an amino acid corresponding to the numbered position with another amino acid; (ii) the removal from a first sequence (such as a wild type sequence) of an amino acid corresponding to the numbered position; or (iii) the addition to a first sequence (such as a wild type sequence) of an additional amino acid at the position corresponding to the numbered position. Addition and removal of amino acids is used in particular where it is desirable for the length of a CDR of an antibody molecule to be within a desired range.

The substitutions which may be made to the human germline heavy and/or light chain sequences are typically confined to positions which are predicted to be solvent accessible in the context of a fully-folded antigen-binding domain of an antibody molecule comprising said sequence.

Solvent accessible positions are those which are expected to be exposed on the surface of the antigen-binding site. Amino acids in these positions are therefore likely to interact directly with the antigen when bound and substitutions in these positions are expected to have the greatest impact on antigen specificity. However, substitutions may also be made to residues which are expected to be buried within the internal structure of an antigen-binding site (not solvent exposed). In particular, substitutions may be made to such residues if they are predicted to influence the three dimensional conformation of the antigen-binding site.

Positions in VH CDR3 which are expected to be solvent accessible include positions 107, 108, 109, 110, 111, 111.1, 111.2, 111.3, 111.4, 112.5, 112.4, 112.3, 112.2, 112.1, 112, 113 and 114. In the libraries of the invention, each antibody molecule may comprise a human germline heavy chain antibody sequence in which one, two, three, four, five, six, seven, eight, nine, ten, eleven, twelve, thirteen, fourteen, fifteen, sixteen or seventeen of these positions may be substituted relative to the wild type human germline heavy chain antibody sequence. Position 115 of VH CDR3 may also be substituted relative to the wild type human germline heavy chain antibody sequence. Position 115 of VH CDR3 is a buried residue which is predicted to influence binding-site conformation.

Positions in VH CDR2 which are expected to be solvent accessible include positions 55, 57, 58, 59, 62, 63, 64 and 66. In the libraries of the invention, each antibody molecule may comprise a human germline heavy chain antibody sequence in which one, two, three, four, five, six, seven or all eight of these positions may be substituted relative to the wild type human germline heavy chain antibody sequence.

Positions in VH CDR1 which are expected to be solvent accessible include positions 35, 36, 37, 38 and 40. In the libraries of the invention, each antibody molecule may comprise a human germline heavy chain antibody sequence in which one, two, three, four or all five of these positions may be substituted relative to the wild type human germline heavy chain antibody sequence.

Positions in VL CDR3 which are expected to be solvent accessible include positions 107, 108, 109, 110, 112, 113 and 114. In the libraries of the invention, each antibody molecule may comprise a human germline heavy chain antibody sequence in which one, two, three, four, five, six or all seven of these positions may be substituted relative to the wild type human germline heavy chain antibody sequence. Position 115 and/or 116 of VL CDR3 may also be substituted relative to the wild type human germline heavy chain antibody sequence. Positions 115 and 116 of VH CDR3 are buried residues which are predicted to influence binding-site conformation.

Positions in VL CDR2 which are expected to be solvent accessible include position 56. In the libraries of the invention, each antibody molecule may comprise a human germline heavy chain antibody sequence in which this position may be substituted relative to the wild type human germline heavy chain antibody sequence.

Positions in VL CDR1 which are expected to be solvent accessible include positions 28, 36 and 37. In the libraries of the invention, each antibody molecule may comprise a human germline heavy chain antibody sequence in which one, two or all three of these positions may be substituted relative to the wild type human germline heavy chain antibody sequence.

The antibody molecules in the libraries of the invention may comprise any combination of substitutions at any of the above-described positions in VH CDRs 1, 2 and 3 and VL CDRs 1, 2 and 3. The diversity in the libraries of the invention is controlled by favouring particular amino acids in particular positions, as is explained in more detail below.

In one category of library of the invention, designated category AL2, substitutions are typically made to positions in each of VH CDR1, 2 and 3 and VL CDR3. In a library of category AL2, the length of the VH CDR3 is preferably between 8 and 17 amino acids. This is achieved by allowing the amino acid at each of positions 109, 110, 111, 111.1, 111.2, 112.2, 112.1, 112 and 113 to independently be present or absent. The length of the VL CDR3 is preferably between 8 and 12 amino acids. This is achieved by allowing the amino acid at each of positions 109, 110, 112 and 113 to independently be present or absent. In a library of category AL2, specific types of amino acid are preferred in each position. In particular, for the VH domain of a library of category AL2:

Firstly, for each antibody molecule in the library, each solvent accessible residue in VH CDRs 1 and 2 is independently substituted with an amino acid selected from tyrosine, serine and glycine, wherein each of tyrosine, serine and glycine is equally preferred. Taking the total population of antibody molecules in the library as whole, tyrosine, serine and glycine are therefore present equally frequently in each said position.

Secondly, for each antibody molecule in the library, each solvent accessible residue in VH CDR3 is independently substituted with an amino acid selected from tyrosine, serine, glycine, alanine, phenylalanine, tryptophan, histidine, proline, valine, aspartate, asparagine, threonine and arginine in the following relative order of preference: 25% Tyr, 15% Ser, 20% Gly, 5% Ala, 5% Phe, 5% Trp, 5% His, 5% Pro, 5% Val, 3% Asp, 3% Asn, 3% Thr, 1% Arg. Taking the total population of antibody molecules in the library as whole, tyrosine, serine, glycine, alanine, phenylalanine, tryptophan, histidine, proline, valine, aspartate, asparagine, threonine and arginine are therefore present at the above-indicated frequencies in each said position.

Thirdly, for each antibody molecule in the library, the amino acid at position 115 of VH CDR3 is independently substituted with an amino acid selected from phenylalanine, isoleucine, leucine and methionine, wherein each of phenylalanine, isoleucine, leucine and methionine is equally preferred. Taking the total population of antibody molecules in the library as whole, phenylalanine, isoleucine, leucine and methionine are therefore present equally frequently in each said position.

In addition, for the VL domain of a library of category AL2:

Firstly, for each antibody molecule in the library, each solvent accessible residue in VL CDR3 is independently substituted with an amino acid selected from tyrosine, serine, glycine, alanine, phenylalanine, tryptophan, histidine, proline, valine, aspartate, asparagines, threonine and arginine in the following relative order of preference: 25% Tyr, 15% Ser, 20% Gly, 5% Ala, 5% Phe, 5% Trp, 5% His, 5% Pro, 5% Val, 3% Asp, 3% Asn, 3% Thr, 1% Arg. Taking the total population of antibody molecules in the library as whole, tyrosine, serine, glycine, alanine, phenylalanine, tryptophan, histidine, proline, valine, aspartate, asparagines, threonine and arginine are therefore present at the above-indicated frequencies in each said position.

Secondly, for each antibody molecule in the library, the residue at position 115 in VL CDR3 is independently substituted with an amino acid selected from phenylalanine and leucine, wherein each of phenylalanine and leucine is equally preferred. Taking the total population of antibody molecules in the library as whole, phenylalanine and leucine are therefore present equally frequently in each said position.

Thirdly, for each antibody molecule in the library, the residue at position 116 in VL CDR3 is independently substituted with an amino acid selected from histidine, proline, leucine, tyrosine, serine and phenylalanine, wherein each of histidine, proline, leucine, tyrosine, serine and phenylalanine is equally preferred. Taking the total population of antibody molecules in the library as whole, histidine, proline, leucine, tyrosine, serine and phenylalanine are therefore present equally frequently in each said position.

In a second category of library of the invention, designated category AL3, substitutions as set out above are typically made to positions in each of VH CDR1, 2 and 3 and VL CDR1, 2 and 3. In such a library, the length of the VH CDR3 is preferably between 8 and 17 amino acids. This is achieved by allowing the amino acid at each of positions 109, 110, 111, 111.1, 111.2, 112.2, 112.1, 112 and 113 to independently be present or absent. The length of the VL CDR3 is preferably between 8 and 12 amino acids. This is achieved by allowing the amino acid at each of positions 109, 110, 112 and 113 to independently be present or absent. In a library of category AL3, specific types of amino acid are preferred in each position. In particular, for the VH domain of a library of category AL3:

Firstly, for each antibody molecule in the library, each solvent accessible residue in VH CDRs 1 and 2 is independently substituted with an amino acid selected from tyrosine, serine and glycine, wherein each of wherein each of tyrosine, serine and glycine is equally preferred. Taking the total population of antibody molecules in the library as whole, tyrosine, serine and glycine are therefore present equally frequently in each said position.

Secondly, for each antibody molecule in the library, each solvent accessible residue in VH CDR3 is independently substituted with an amino acid selected from tyrosine, glycine, serine, tryptophan, alanine, phenylalanine, histidine, proline, valine, aspartate, asparagine, threonine and arginine in the following relative order of preference: 20% Tyr, 15% Gly, 15% Ser, 5% Trp, 5% Ala, 5% Phe, 15% His, 5% Pro, 5% Val, 3% Asp, 3% Asn, 3% Thr, 1% Arg. Taking the total population of antibody molecules in the library as whole, tyrosine, glycine, serine, tryptophan, alanine, phenylalanine, histidine, proline, valine, aspartate, asparagine, threonine and arginine are therefore present at the above-indicated frequencies in each said position.

Thirdly, for each antibody molecule in the library, the amino acid at position 115 of VH CDR3 is independently substituted with an amino acid selected from phenylalanine, isoleucine, leucine and methionine, wherein each of phenylalanine, isoleucine, leucine and methionine is equally preferred. Taking the total population of antibody molecules in the library as whole, phenylalanine, isoleucine, leucine and methionine are therefore present equally frequently in each said position.

In addition, for the VL domain of a library of category AL3:

Firstly, for each antibody molecule in the library, the residues at positions 28 and 37 in VL CDR1 are each independently substituted with an amino acid selected from tyrosine, serine, glycine, asparagine and alanine, wherein each of tyrosine, serine, glycine, asparagine and alanine is equally preferred. Taking the total population of antibody molecules in the library as whole, tyrosine, serine, glycine, asparagine and alanine are therefore present equally frequently in each said position.

Secondly, for each antibody molecule in the library, the residue at position 36 in VL CDR1 is independently substituted with an amino acid selected from serine and arginine, wherein each of serine and arginine is equally preferred. Taking the total population of antibody molecules in the library as whole, serine and arginine are therefore present equally frequently in each said position.

Thirdly, for each antibody molecule in the library, the residue at position 56 in VL CDR2 is independently substituted with an amino acid selected from tyrosine, serine, glycine, asparagine and alanine, wherein each of tyrosine, serine, glycine, asparagine and alanine is equally preferred. Taking the total population of antibody molecules in the library as whole, tyrosine, serine, glycine, asparagine and alanine are therefore present equally frequently in each said position.

Fourthly, for each antibody molecule in the library, each solvent accessible residue in VL CDR3 is independently substituted with an amino acid selected from tyrosine, glycine, serine, tryptophan, alanine, phenylalanine, histidine, proline, valine, aspartate, asparagine, threonine and arginine, in the following relative order of preference: 25% Tyr, 20% Gly, 15% Ser, 5% Trp, 5% Ala, 5% Phe, 5% His, 5% Pro, 5% Val, 3% Asp, 3% Asn, 3% Thr, 1% Arg. Taking the total population of antibody molecules in the library as whole, tyrosine, glycine, serine, tryptophan, alanine, phenylalanine, histidine, proline, valine, aspartate, asparagine, threonine and arginine are therefore present at the above-indicated frequencies in each said position.

Fifthly, for each antibody molecule in the library, the residue at position 115 in VL CDR3 is independently substituted with an amino acid selected from phenylalanine and leucine, wherein each of phenylalanine and leucine is equally preferred. Taking the total population of antibody molecules in the library as whole, phenylalanine and leucine are therefore present equally frequently in each said position.

Sixthly, for each antibody molecule in the library, the residue at position 116 in VL CDR3 is independently substituted with an amino acid selected from histidine, proline, leucine, tyrosine, serine and phenylalanine, wherein each of histidine, proline, leucine, tyrosine, serine and phenylalanine is equally preferred. Taking the total population of antibody molecules in the library as whole, histidine, proline, leucine, tyrosine, serine and phenylalanine are therefore present equally frequently in each said position.

In another category of library of the invention, designated category AL2/3, a proportion of the antibody molecules in the library are defined as in library category AL2 and a proportion of antibody molecules in the library are defined as in library category AL3. The proportions may preferably be equal. However, the proportions may be varied such that the proportion of antibody molecules as defined in AL2 is higher or lower than the proportion of antibody molecules as defined in AL3. Thus, the ratio of the proportion of antibody molecules as defined in AL2 relative to the proportion of antibody molecules as defined in AL3 may be 1:2, 1:3, 1:4, 1:5, 1:6, 1:7, 1:8, 1:9, 9:1, 8:1, 7:1, 6:1, 5:1, 4:1, 3:1 or 2:1.

In another category of library of the invention, designated category AL1, substitutions as set out above are typically made to positions in each of VH CDR1, 2 and 3 and VL CDR3. In such a library, the length of the VH CDR3 is preferably between 8 and 22 amino acids. The length of the VL CDR3 is preferably between 8 and 12 amino acids. This is achieved by allowing the amino acid at each of positions 109, 110, 111, 111.1, 111.2, 111.3, 111.4, 112.5, 112.4, 112.3, 112.2, 112.1, 112 and 113 to independently be present or absent. The length of the VL CDR3 is preferably between 8 and 12 amino acids. This is achieved by allowing the amino acid at each of positions 109, 110, 112 and 113 to independently be present or absent. In a library of category AL1, specific types of amino acid are preferred in each position. In particular, for the VH domain of a library of category AL1:

Firstly, for each antibody molecule in the library, each solvent accessible residue in VH CDRs 1 and 2 is independently substituted with an amino acid selected from tyrosine, serine and glycine, wherein each of wherein each of tyrosine, serine and glycine is equally preferred. Taking the total population of antibody molecules in the library as whole, tyrosine, serine and glycine are therefore present equally frequently in each said position.

Secondly, for each antibody molecule in the library, each solvent accessible residue in VH CDR3 is independently substituted with an amino acid selected from tyrosine, serine, glycine, alanine, phenylalanine, tryptophan, histidine, proline, valine, aspartate, asparagine, threonine and arginine in the following relative order of preference: 25% Tyr, 15% Ser, 15% Gly, 5% Ala, 5% Phe, 10% Trp, 5% His, 5% Pro, 5% Val, 3% Asp, 3% Asn, 3% Thr and 1% Arg. Taking the total population of antibody molecules in the library as whole, tyrosine, serine, glycine, alanine, phenylalanine, tryptophan, histidine, proline, valine, aspartate, asparagine, threonine and arginine are therefore present at the above-indicated frequencies in each said position.

Thirdly, for each antibody molecule in the library, the amino acid at position 115 of VH CDR3 is independently substituted with an amino acid selected from phenylalanine, isoleucine, leucine and methionine, wherein each of phenylalanine, isoleucine, leucine and methionine is equally preferred. Taking the total population of antibody molecules in the library as whole, phenylalanine, isoleucine, leucine and methionine are therefore present equally frequently in each said position.

In addition, for the VL domain of a library of category AL1:

Firstly, for each antibody molecule in the library, each solvent accessible residue in VL CDR3 is independently substituted with an amino acid selected from tyrosine, serine, glycine, alanine, phenylalanine, tryptophan, histidine, proline, valine, aspartate, asparagine, threonine and arginine in the following relative order of preference: 25% Tyr, 15% Ser, 15% Gly, 5% Ala, 5% Phe, 10% Trp, 5% His, 5% Pro, 5% Val, 3% Asp, 3% Asn, 3% Thr and 1% Arg. Taking the total population of antibody molecules in the library as whole, tyrosine, serine, glycine, alanine, phenylalanine, tryptophan, histidine, proline, valine, aspartate, asparagine, threonine and arginine are therefore present at the above-indicated frequencies in each said position.

Secondly, for each antibody molecule in the library, the residue at position 115 in VL CDR3 is independently substituted with an amino acid selected from phenylalanine and leucine, wherein each of phenylalanine and leucine is equally preferred. Taking the total population of antibody molecules in the library as whole, phenylalanine and leucine are therefore present equally frequently in each said position.

Thirdly, for each antibody molecule in the library, the residue at position 116 in VL CDR3 is independently substituted with an amino acid selected from histidine, proline, leucine, tyrosine, serine and phenylalanine, wherein each of histidine, proline, leucine, tyrosine, serine and phenylalanine is equally preferred. Taking the total population of antibody molecules in the library as whole, histidine, proline, leucine, tyrosine, serine and phenylalanine are therefore present equally frequently in each said position.

In each of library categories AL2, AL3 and AL1, the unsubstituted human germline heavy chain antibody preferably comprises SEQ ID NO: 1 linked to SEQ ID NO: 2. SEQ ID NO: 3 shows these two sequence linked as a contiguous sequence, which may be considered a starting template for the libraries. In each of library categories AL2, AL3 and AL1, the unsubstituted human germline light chain antibody preferably comprises SEQ ID NO: 4 linked to SEQ ID NO: 5. SEQ ID NO: 6 shows these two sequence linked as a contiguous sequence, which may be considered a starting template for the libraries.

The diversity in the VH domains of the antibody molecules in library categories AL2, AL3 and AL1 is summarised in Table 1. The diversity in the VL domains of the antibody molecules in library categories AL2, AL3 and AL1 is summarised in Table 2. Tables 1 and 2 recite amino acid sequences in the standard single letter amino acid code. Positions within each CDR are numbered according to the IMGT scheme. The wildtype sequences are shown for comparison.

In Table 1, the human germline heavy chain template sequence of SEQ ID NO: 3 is shown in the first row ("T"). Sequences of library categories AL1, AL2 and AL3 are in the subsequent rows as indicated ("1", "2" and "3"). "." means an amino acid is identical to the template sequence at that position. "-" means a residue is absent in the sequence. Where multiple amino acid codes are shown in a position (e.g. "YSG") this means that each of the amino acids shown is equally preferred in that position. "1" in a position indicates that amino acids are present in the following relative order of preference: 25% Tyr, 15% Ser, 15% Gly, 5% Ala, 5% Phe, 10% Trp, 5% His, 5% Pro, 5% Val, 3% Asp, 3% Asn, 3% Thr and 1% Arg. "2" in a position indicates that amino acids are present in the following relative order of preference: 25% Tyr, 15% Ser, 20% Gly, 5% Ala, 5% Phe, 5% Trp, 5% His, 5% Pro, 5% Val, 3% Asp, 3% Asn, 3% Thr, 1% Arg. "3" in a position indicates that amino acids are present in the following relative order of preference: 20% Tyr, 15% Gly, 15% Ser, 5% Trp, 5% Ala, 5% Phe, 15% His, 5% Pro, 5% Val, 3% Asp, 3% Asn, 3% Thr, 1% Arg.

Since the length of VH CDR3 in library AL1 may vary between 8 and 22 amino acids in length, the amino acid at each of positions 109, 110, 111, 111.1, 111.2, 111.3, 111.4, 112.5, 112.4, 112.3, 112.2, 112.1, 112 and 113 may independently be absent, or present as shown in Table 1. Since the length of VH CDR3 in libraries AL2 and 3 may vary between 8 and 17 amino acids in length, the amino acid at each of positions 109, 110, 111, 111.1, 111.2, 112.2, 112.1, 112 and 113 may independently be absent, or present as shown in Table 1.

TABLE 1

The sequence provided in row "T" is SEQ ID NO: 3.

CDR 1 residues:

|   |   |   |   |   |   |   |   |   |   |   |   |   |   |   |   |   |   |   |   |   |   |   |   |   |   | 27 | 28 | 29 | 30 | 35 | 36 | 37 | 38 | 39 | 40 |   |   |   |   |
|---|---|---|---|---|---|---|---|---|---|---|---|---|---|---|---|---|---|---|---|---|---|---|---|---|---|----|----|----|----|----|----|----|----|----|----|---|---|---|---|
| T | E | V | Q | L | L | E | G | G | G | L | V | Q | P | G | G | S | L | R | L | S | C | A | A | S | G | F  | T  | F  | S  | S  | S  | Y  | A  | M  | S  | W | B | Q | A | P |
| 2 | . | . | . | . | . | . | . | . | . | . | . | . | . | . | . | . | . | . | . | . | . | . | . | . | . | .  | .  | .  | .  | Y  | Y  | Y  | Y  | Y  | Y  | . | . | . | . | . |
|   |   |   |   |   |   |   |   |   |   |   |   |   |   |   |   |   |   |   |   |   |   |   |   |   |   |    |    |    |    | G  | G  | G  | G  | G  | G  |   |   |   |   |
| 3 | . | . | . | . | . | . | . | . | . | . | . | . | . | . | . | . | . | . | . | . | . | . | . | . | . | .  | .  | .  | .  | Y  | Y  | Y  | Y  | Y  | Y  | . | . | . | . | . |
|   |   |   |   |   |   |   |   |   |   |   |   |   |   |   |   |   |   |   |   |   |   |   |   |   |   |    |    |    |    | S  | S  | S  | S  | S  | S  |   |   |   |   |
| 1 | . | . | . | . | . | . | . | . | . | . | . | . | . | . | . | . | . | . | . | . | . | . | . | . | . | .  | .  | .  | .  | Y  | Y  | Y  | Y  | Y  | Y  | . | . | . | . | . |
|   |   |   |   |   |   |   |   |   |   |   |   |   |   |   |   |   |   |   |   |   |   |   |   |   |   |    |    |    |    | G  | G  | G  | G  | G  | G  |   |   |   |   |

CDR 2 residues:

|   |   |   |   |   |   |   |   |   |   |   |   |   |   |   |   |   | 55 | 56 | 57 | 58 | 59 | 62 | 63 | 64 | 65 | 66 |   |   |   |   |   |   |   |   |   |   |   |
|---|---|---|---|---|---|---|---|---|---|---|---|---|---|---|---|---|----|----|----|----|----|----|----|----|----|----|---|---|---|---|---|---|---|---|---|---|---|
| T | G | K | G | L | E | W | V | S | A | I | S | G | S | G | G | S | T  | Y  | Y  | A  | D  | S  | V  | K  | G  | R  | F | T | I | S | R | D | N | S | K | N | T | L | Y | L |
| 2 | . | . | . | . | . | . | . | . | . | Y | Y | Y | Y | Y | Y | . | Y  |    |    |    |    |    |    |    |    |    |   |   |   |   |   |   |   |   |   |   |   |   |   |
|   |   |   |   |   |   |   |   |   |   | G | G | G | G | G | G |   |    |    |    |    |    |    |    |    |    |    |   |   |   |   |   |   |   |   |   |   |   |   |   |
| 3 | . | . | . | . | . | . | . | . | . | Y | Y | Y | Y | Y | Y | . | Y  |    |    |    |    |    |    |    |    |    |   |   |   |   |   |   |   |   |   |   |   |   |   |
|   |   |   |   |   |   |   |   |   |   | S | S | S | S | S | S |   |    |    |    |    |    |    |    |    |    |    |   |   |   |   |   |   |   |   |   |   |   |   |   |
| 1 | . | . | . | . | . | . | . | . | . | Y | Y | Y | Y | Y | Y | . | Y  |    |    |    |    |    |    |    |    |    |   |   |   |   |   |   |   |   |   |   |   |   |   |
|   |   |   |   |   |   |   |   |   |   | G | G | G | G | G | G |   |    |    |    |    |    |    |    |    |    |    |   |   |   |   |   |   |   |   |   |   |   |   |   |

CDR 3 residues:

|   |   |   |   |   |   |   |   |   |   |   |   | 105 | 106 | 107 | 108 | 109 | 110 | 111 | 112 | 113 | 114 | 115 | 116 | 117 |   |   |   |   |
|---|---|---|---|---|---|---|---|---|---|---|---|-----|-----|-----|-----|-----|-----|-----|-----|-----|-----|-----|-----|-----|---|---|---|---|
| T | Q | M | N | S | L | R | A | E | D | T | A | V   | Y   | Y   | C   | A   | R   | —   | —   | —   | —   | —   | —   | —   | F | D | Y | W | G | Q |
| 2 | . | . | . | . | . | . | . | . | . | . | . | .   | .   | .   | .   | .   | .   | 2   | 2   | 2   | 2   | 2   | 2   | 2   | F | F | . | . | . | . |
|   |   |   |   |   |   |   |   |   |   |   |   |     |     |     |     |     |     |     |     |     |     |     |     |     | I | I |   |   |   |   |
|   |   |   |   |   |   |   |   |   |   |   |   |     |     |     |     |     |     |     |     |     |     |     |     |     | L | L |   |   |   |   |
|   |   |   |   |   |   |   |   |   |   |   |   |     |     |     |     |     |     |     |     |     |     |     |     |     | M | M |   |   |   |   |
| 3 | . | . | . | . | . | . | . | . | . | . | . | .   | .   | .   | .   | .   | .   | 3   | 3   | 3   | 3   | 3   | 3   | 3   | F | F | . | . | . | . |
|   |   |   |   |   |   |   |   |   |   |   |   |     |     |     |     |     |     |     |     |     |     |     |     |     | I | I |   |   |   |   |
|   |   |   |   |   |   |   |   |   |   |   |   |     |     |     |     |     |     |     |     |     |     |     |     |     | L | L |   |   |   |   |
|   |   |   |   |   |   |   |   |   |   |   |   |     |     |     |     |     |     |     |     |     |     |     |     |     | M | M |   |   |   |   |
| 1 | . | . | . | . | . | . | . | . | . | . | . | .   | .   | .   | .   | .   | .   | 1   | 1   | 1   | 1   | 1   | 1   | 1   | F | F | . | . | . | . |
|   |   |   |   |   |   |   |   |   |   |   |   |     |     |     |     |     |     |     |     |     |     |     |     |     | I | I |   |   |   |   |
|   |   |   |   |   |   |   |   |   |   |   |   |     |     |     |     |     |     |     |     |     |     |     |     |     | L | L |   |   |   |   |
|   |   |   |   |   |   |   |   |   |   |   |   |     |     |     |     |     |     |     |     |     |     |     |     |     | M | M |   |   |   |   |

TABLE 1-continued

The sequence provided in row "T" is SEQ ID NO: 3.

| G | T | L | V | T | V | S | S | . | . | . |
| . | . | . | . | . | . | . | . | . | . | . |

In Table 2, the human germline light chain template sequence of SEQ ID NO: 6 is shown in the first row ("T"). Sequences of library categories AL1, AL2 and AL3 are in the subsequent rows as indicated ("1", "2" and "3"). "." means an amino acid is identical to the template sequence at that position. "-" means a residue is absent in the sequence. Where multiple amino acid codes are shown in a position (e.g. "YSG") this means that each of the amino acids shown is equally preferred in that position. "1" in a position indicates that amino acids are present in the following relative order of preference: 25% Tyr, 15% Ser, 15% Gly, 5% Ala, 5% Phe, 10% Trp, 5% His, 5% Pro, 5% Val, 3% Asp, 3% Asn, 3% Thr and 1% Arg. "2" in a position indicates that amino acids are present in the following relative order of preference: 25% Tyr, 15% Ser, 20% Gly, 5% Ala, 5% Phe, 5% Trp, 5% His, 5% Pro, 5% Val, 3% Asp, 3% Asn, 3% Thr, 1% Arg. "3" in a position indicates that amino acids are present in the following relative order of preference: 25% Tyr, 15% Ser, 20% Gly, 5% Ala, 5% Phe, 5% Trp, 5% His, 5% Pro, 5% Val, 3% Asp, 3% Asn, 3% Thr, 1% Arg.

Since the length of VL CDR3 in all three libraries may vary between 8 and 12 amino acids in length, the amino acid at each of positions 109, 110, 112 and 113 may independently be absent, or present as shown in Table 2.

TABLE 2

The sequence provided in row "T" is SEQ ID NO: 3.

```
                                                          2 2 3 3
                                                          8 9 6 7
T  D I Q M T Q S P D D L S D V G D R V T I T C R A S Q S I S S Y L N W Y Q Q K P
23 . . . . . . . . . . . . . . . . . . . . . . . . . . . Y R Y . . . . . . . . .
                                                          S s G . . . . . . . . .
                                                          G   D . . . . . . . . .
                                                          D   A . . . . . . . . .
                                                          A
1  . . . . . . . . . . . . . . . . . . . . . . . . . . . . . . . . . . . . . . .
                         5
                         6
T  G K A P K L L I Y A A S S L Q S G V P S R F S G S G S G T D F T L T I S S L Q P
23 . . . . . . . . . . . Y . . . . . . . . . . . . . . . . . . . . . . . . . . .
                         S
                         G
                         D
                         A
1  . . . . . . . . . . . . . . . . . . . . . . . . . . . . . . . . . . . . . . .

1 1 1 1 1 1 1 1 1 1 1 1 1
                  0 0 0 0 0 1 1 1 1 1 1 1 1
                  5 6 7 8 9 0 1 2 3 4 5 6 7
CDR 3 residues:
T  E D F A T Y Y C Q Q — Y S T P Y T F G Q G T K L E I K
2                      2 2 2 2 2 2

3  . . . . . . . . . . 3 3 3 3 3 3 P H
                                     L P
                                     Y L
                                     S Y
                                     F S
                                         F
1  . . . . . . . . . . 1 1 1 1 1 1 1 PL H
                                       P P
                                       L L
                                       Y Y
                                       S S
                                       F F
```

Substitutions of amino acids may be introduced into a germline heavy or light chain sequence by any suitable method. Such methods typically involve making substitutions to a nucleic acid sequence encoding the amino acid sequence of a germline heavy or light chain variable domain. The heavy or light chain variable domain incorporating the substitutions may then be produced by expressing the nucleic acid sequence.

Preferred methods introduce a range of different amino acids at a desired frequency in each position, such that the method results in a population of antibody molecules in which, when considering the population as whole, a particular amino acid is present at a particular frequency in a particular position, thus providing a library of the invention. Some suitable methods are outlined below and in the Examples.

Nucleic Acid Molecules, Library Thereof and Methods of Producing Libraries

The present invention provides a library of nucleic acid molecules which encodes a library of antibody molecules of the invention. Such a library of nucleic acid molecules comprises a population of different nucleic acid molecules which each encode a different antibody molecule or a domain thereof. It is possible to produce such a library by introducing multiple different changes to the sequence of a nucleic acid molecule encoding a germline sequence, such that multiple different nucleic acid sequences are produced. Methods for introducing specific changes into a nucleic acid sequence are well established. A preferred method is the Kunkel method (Kunkel et al., Methods Enzymol. (1987), 154:367-382), which is a form of oligonucleotide-directed mutagenesis. This method is described further below and in the Examples.

In Kunkel's method, the DNA fragment to be mutated is inserted into a phagemid vector, such as a M13 phagemid. The DNA fragment is typically linked to the gene encoding a bacteriophage coat protein such as pIII. The phagemid vector is then transformed into an E. coli strain deficient in two enzymes, dUTPase (dut) and uracil deglycosidase (ung). Helper phage is typically present in the medium as required, to enable phage replication. dUTPase and uraceil deglycosidase are both part of a DNA repair pathway that protects the bacterial chromosome from mutations by the spontaneous deamination of dCTP to dUTP. The dUTPase deficiency prevents the breakdown of dUTP, resulting in a high level of dUTP in the cell. The uracil deglycosidase deficiency prevents the removal of uracil from newly synthesized DNA. As the double-mutant E. coli replicates the phage DNA, its enzymatic machinery may, therefore, misincorporate dUTP instead of dTTP, resulting in single-strand DNA that contains some uracils (ssUDNA). The ssUDNA is extracted from the bacteriophage that is released into the medium, and then used as template for mutagenesis. An oligonucleotide containing the desired mutation (a "mutagenic oligonucleotide" or "mutagenic primer") is used for primer extension. The heteroduplex DNA that forms consists of one parental non-mutated strand containing dUTP and a mutated strand containing dTTP. The DNA is then transformed into an E. coli strain carrying the wildtype dut and ung genes. Here, the uracil-containing parental DNA strand is degraded, so that nearly all of the resulting DNA consists of the mutated strand. An advantage of this mutagenesis approach is that the mutated DNA strands are already present as phagemid vectors, which may then be used to transform further E. coli resulting in expression of the mutated polypeptide products, typically linked to a coat protein of the bacteriophage that are produced. That is, a phage display library of the mutated polypeptide products may be readily produced.

In the context of the present invention, the dut– ung– E. coli is transformed with a phagemid vector incorporating a nucleic acid sequence which encodes a human germline antibody sequence. For example, said phagemid vector may comprise a nucleic acid sequence encoding the human germline antibody heavy chain sequence of SEQ ID NO: 1 linked to SEQ ID NO:2, and/or a nucleic acid sequence encoding the human germline antibody light chain sequence of SEQ ID NO: 4 linked to SEQ ID NO: 5, optionally wherein said nucleic acid sequences are joined by a linking nucleic acid sequence, which linking sequence may encode an amino acid sequence such as GGGGSGGGGSGGGGS (SEQ ID NO: 23). Said nucleic acid sequence encoding a human germline antibody sequence is typically linked to a further nucleic acid sequence encoding a coat protein of a filamentous bacteriophage, optionally wherein said coat protein is pIII. Additional coding sequences may also be included, such a sequence encoding an affinity tag to facilitate isolation of the expressed antibody molecule. Other sequences may also be included, for example to introduce cleavage sites between the coat protein and the antibody molecule. Suitable nucleic acid sequences are shown as SEQ ID NO: 25 and 26.

Starting with such a phagemid vector, the different nucleic acid libraries of the invention (and ultimately the antibody molecule libraries of the invention) may then be produced by using suitable mutagenic primers in the primer extension step of Kunkel's method as outlined above. This introduces changes in the nucleic acid sequence encoding the human germline antibody sequence, which result in changes in the amino acid sequence of the expressed antibody molecules.

The design of appropriate mutagenic primers is possible based on the known degeneracy of codons in the genetic code. That is, one selects an appropriate triplet codon in each position of the mutagenic oligonucleotide such that a desired amino acid is encoded by the resulting mutated DNA. The following table summarises the triplet codons which encode each amino acid.

| Amino acid | Codons | Compressed annotation (IUPAC) | Amino acid | Codons | Compressed annotation (IUPAC) |
| --- | --- | --- | --- | --- | --- |
| Ala/A | GCU, GCC, GCA, GCG | GCN | Leu/L | UUA, UUG, CUU, CUC, CUA, CUG | YUR, CUN |
| Arg/R | CGU, CGC, CGA, CGG, AGA, AGG | CGN, MGR | Lys/K | AAA, AAG | AAR |
| Asn/N | AAU, AAC | AAY | Met/M | AUG | |

| Amino acid | Codons | Compressed annotation (IUPAC) | Amino acid | Codons | Compressed annotation (IUPAC) |
|---|---|---|---|---|---|
| Asp/D | GAU, GAC | GAY | Phe/F | UUU, UUC | UUY |
| Cys/C | UGU, UGC | UGY | Pro/P | CCU, CCC, CCA, CCG | CCN |
| Gln/Q | CAA, CAG | CAR | Ser/S | UCU, UCC, UCA, UCG, AGU, AGC | UCN, AGY |
| Glu/E | GAA, GAG | GAR | Thr/T | ACU, ACC, ACA, ACG | CAN |
| Gly/G | GGU, GGC, GGA, GGG | GGN | Trp/W | UGG | |
| His/H | CAU, CAC | CAY | Tyr/Y | UAU, UAC | UAY |
| Ile/I | AUU, AUC, AUA | AUH | Val/V | GUU, GUC, GUA, GUG | GUN |
| START | AUG | | STOP | UAA, UGA, UAG | UAR, URA |

The nucleic acid notation used herein is as formalized by the International Union of Pure and Applied Chemistry (IUPAC), which is summarised in the following table.

| IUPAC code | Description | Bases represented |
|---|---|---|
| A | Adenine | A |
| C | Cytosine | C |
| G | Guanine | G |
| T (or U) | Thymine (or Uracil) | T (or U) |
| R | Purine | A or G |
| Y | Pyrimidine | C or T |
| S | Strong | G or C |
| W | Weak | A or T |
| K | Keto | G or T |
| M | Amino | A or C |
| B | Not A | C or G or T |
| D | Not C | A or G or T |
| H | Not G | A or C or T |
| V | Not T (nor U) | A or C or G |
| N | Any base | Any base |
| — | Gap | Gap |

For example, to produce a library of category AL1, different pools of primers may be designed to introduce the desired diversity into different positions of the various CDRs of the human germline sequences, as well as different lengths of CDR. Exemplary pools of primers which may be used to produce a library of category AL1 may be as follows (and as summarised in FIGS. 1A and B):

For VH CDR1, a single pool of primers was prepared, referred to as H1-1a. Each primer in pool H1-1a comprises a conserved sequence at the 5' end (GCC AGC GGA TTC ACC TTT—SEQ ID NO: 7) and a conserved sequence at the 3' end (TGG GTC CGC CAG GCT CCA—SEQ ID NO: 8), joined together by one of multiple possible variant sequences. The variant sequences each consist of six nucleotide triplet codons, i.e. 18 nucleotides in total. The fifth codon (nucleotides 13, 14, 15) is ATG. The first to fourth and sixth codons are each independently selected to encode tyrosine, serine or glycine. Within the pool as whole, in each of these codon positions, codons for tyrosine, serine and glycine are present at equal frequencies.

For VH CDR2, a single pool of primers was prepared, referred to as H2-1a. Each primer in pool H2-1a comprises a conserved sequence at the 5' end (GGG CTG GAG TGG GTC TCA—SEQ ID NO: 9) and a conserved sequence at the 3' end (TAT GCA GAC TCC GTG AAG—SEQ ID NO: 10), joined together by one of multiple possible variant sequences. The variant sequences each consist of ten nucleotide triplet codons, i.e. 30 nucleotides in total. The second codon (nucleotides 3, 4, 5) is ATT. The ninth codon (nucleotides 25, 26, 27) is ACA. The first, third to eighth and tenth codons are each independently selected to encode tyrosine, serine or glycine. Within the pool as whole, in each of these codon positions, codons for tyrosine, serine and glycine are present at equal frequencies.

For VH CDR3, fifteen different pools of primers were prepared, one pool for each of the permitted VH CDR3 lengths of 8, 9, 10, 11, 12, 13, 14, 15, 16, 17, 18, 19, 20, 21 and 22 amino acids.

The primer pool for a VH CDR3 length of 8 amino acids is referred to as H3-8. Each primer in pool H3-8 comprises a conserved sequence at the 5' end (GTA TAT TAT TGT GCG CGC—SEQ ID NO: 11) and a conserved sequence at the 3' end (WTK GAC TAT TGG GGC CAG GGA—SEQ ID NO: 12), joined together by one of multiple possible variant sequences. The variant sequences each consist of three nucleotide triplet codons, i.e. 9 nucleotides in total. These codons are each independently selected to encode tyrosine, serine, glycine, alanine, phenylalanine, tryptophan, histidine, proline, valine, aspartate, asparagine, threonine or arginine. Within the pool as whole, in each of these codon positions, codons for the listed amino acids are present at the following frequencies: 25% Tyr, 15% Ser, 15% Gly, 5% Ala, 5% Phe, 10% Trp, 5% His, 5% Pro, 5% Val, 3% Asp, 3% Asn, 3% Thr and 1% Arg.

The primer pool for a VH CDR3 length of 9 amino acids is referred to as H3-9. Each primer in pool H3-9 comprises the same conserved sequences at the 5' and 3' ends as the primers in pool H3-8, joined by one of multiple possible variant sequences. However, each variant sequence consists of four nucleotide triplet codons, i.e. 12 nucleotides in total. These codons are each independently selected to encode amino acids from the same list as in pool H3-8. Within the pool as a whole, codons for said amino acids are present at the same frequencies as in pool H3-8.

The primer pool for a VH CDR3 length of 10 amino acids is referred to as H3-10. Each primer in pool H3-10 comprises the same conserved sequences at the 5' and 3' ends as the primers in pool H3-8, joined by one of multiple possible variant sequences. However, each variant sequence consists of 5 nucleotide triplet codons, i.e. 15 nucleotides in total. These codons are each independently selected to encode amino acids from the same list as in pool H3-8. Within the pool as a whole, codons for said amino acids are present at the same frequencies as in pool H3-8.

The primer pool for a VH CDR3 length of 11 amino acids is referred to as H3-11. Each primer in pool H3-11 comprises the same conserved sequences at the 5' and 3' ends as the primers in pool H3-8, joined by one of multiple possible variant sequences. However, each variant sequence consists of 6 nucleotide triplet codons, i.e. 18 nucleotides in total. These codons are each independently selected to encode amino acids from the same list as in pool H3-8. Within the pool as a whole, codons for said amino acids are present at the same frequencies as in pool H3-8.

The primer pool for a VH CDR3 length of 12 amino acids is referred to as H3-12. Each primer in pool H3-12 comprises the same conserved sequences at the 5' and 3' ends as the primers in pool H3-8, joined by one of multiple possible variant sequences. However, each variant sequence consists of 7 nucleotide triplet codons, i.e. 21 nucleotides in total. These codons are each independently selected to encode amino acids from the same list as in pool H3-8. Within the pool as a whole, codons for said amino acids are present at the same frequencies as in pool H3-8.

The primer pool for a VH CDR3 length of 13 amino acids is referred to as H3-13. Each primer in pool H3-13 comprises the same conserved sequences at the 5' and 3' ends as the primers in pool H3-8, joined by one of multiple possible variant sequences. However, each variant sequence consists of 8 nucleotide triplet codons, i.e. 24 nucleotides in total. These codons are each independently selected to encode amino acids from the same list as in pool H3-8. Within the pool as a whole, codons for said amino acids are present at the same frequencies as in pool H3-8.

The primer pool for a VH CDR3 length of 14 amino acids is referred to as H3-14. Each primer in pool H3-14 comprises the same conserved sequences at the 5' and 3' ends as the primers in pool H3-8, joined by one of multiple possible variant sequences. However, each variant sequence consists of 9 nucleotide triplet codons, i.e. 27 nucleotides in total. These codons are each independently selected to encode amino acids from the same list as in pool H3-8. Within the pool as a whole, codons for said amino acids are present at the same frequencies as in pool H3-8.

The primer pool for a VH CDR3 length of 15 amino acids is referred to as H3-15. Each primer in pool H3-15 comprises the same conserved sequences at the 5' and 3' ends as the primers in pool H3-8, joined by one of multiple possible variant sequences. However, each variant sequence consists of 10 nucleotide triplet codons, i.e. 30 nucleotides in total. These codons are each independently selected to encode amino acids from the same list as in pool H3-8. Within the pool as a whole, codons for said amino acids are present at the same frequencies as in pool H3-8.

The primer pool for a VH CDR3 length of 16 amino acids is referred to as H3-16. Each primer in pool H3-16 comprises the same conserved sequences at the 5' and 3' ends as the primers in pool H3-8, joined by one of multiple possible variant sequences. However, each variant sequence consists of 11 nucleotide triplet codons, i.e. 33 nucleotides in total. These codons are each independently selected to encode amino acids from the same list as in pool H3-8. Within the pool as a whole, codons for said amino acids are present at the same frequencies as in pool H3-8.

The primer pool for a VH CDR3 length of 17 amino acids is referred to as H3-17. Each primer in pool H3-17 comprises the same conserved sequences at the 5' and 3' ends as the primers in pool H3-8, joined by one of multiple possible variant sequences. However, each variant sequence consists of 12 nucleotide triplet codons, i.e. 36 nucleotides in total. These codons are each independently selected to encode amino acids from the same list as in pool H3-8. Within the pool as a whole, codons for said amino acids are present at the same frequencies as in pool H3-8.

The primer pool for a VH CDR3 length of 18 amino acids is referred to as H3-18. Each primer in pool H3-18 comprises the same conserved sequences at the 5' and 3' ends as the primers in pool H3-8, joined by one of multiple possible variant sequences. However, each variant sequence consists of 13 nucleotide triplet codons, i.e. 39 nucleotides in total. These codons are each independently selected to encode amino acids from the same list as in pool H3-8. Within the pool as a whole, codons for said amino acids are present at the same frequencies as in pool H3-8.

The primer pool for a VH CDR3 length of 19 amino acids is referred to as H3-19. Each primer in pool H3-19 comprises the same conserved sequences at the 5' and 3' ends as the primers in pool H3-8, joined by one of multiple possible variant sequences. However, each variant sequence consists of 14 nucleotide triplet codons, i.e. 42 nucleotides in total. These codons are each independently selected to encode amino acids from the same list as in pool H3-8. Within the pool as a whole, codons for said amino acids are present at the same frequencies as in pool H3-8.

The primer pool for a VH CDR3 length of 20 amino acids is referred to as H3-20. Each primer in pool H3-20 comprises the same conserved sequences at the 5' and 3' ends as the primers in pool H3-8, joined by one of multiple possible variant sequences. However, each variant sequence consists of 15 nucleotide triplet codons, i.e. 45 nucleotides in total. These codons are each independently selected to encode amino acids from the same list as in pool H3-8. Within the pool as a whole, codons for said amino acids are present at the same frequencies as in pool H3-8.

The primer pool for a VH CDR3 length of 21 amino acids is referred to as H3-21. Each primer in pool H3-21 comprises the same conserved sequences at the 5' and 3' ends as the primers in pool H3-8, joined by one of multiple possible variant sequences. However, each variant sequence consists of 16 nucleotide triplet codons, i.e. 48 nucleotides in total. These codons are each independently selected to encode amino acids from the same list as in pool H3-8. Within the pool as a whole, codons for said amino acids are present at the same frequencies as in pool H3-8.

The primer pool for a VH CDR3 length of 22 amino acids is referred to as H3-22. Each primer in pool H3-22 comprises the same conserved sequences at the 5' and 3' ends as the primers in pool H3-8, joined by one of multiple possible variant sequences. However, each variant sequence consists of 17 nucleotide triplet codons, i.e. 51 nucleotides in total. These codons are each independently selected to encode amino acids from the same list as in pool H3-8. Within the pool as a whole, codons for said amino acids are present at the same frequencies as in pool H3-8.

For VL CDR3, five different pools of primers were prepared, one pool for each of the permitted VL CDR3 lengths of 8, 9, 10, 11 and 12 amino acids.

The primer pool for a VL CDR3 length of 8 amino acids is referred to as K3-8. Each primer in pool K3-8 comprises a conserved sequence at the 5' end (ACT TAT TAC TGT CAA CAG—SEQ ID NO: 13) and a conserved sequence at the 3' end (CYG YHC ACT TTT GGC CAG GGG ACC—SEQ ID NO: 14), joined together by one of multiple possible variant sequences. The variant sequences each consist of three nucleotide triplet codons, i.e. 9 nucleotides in total. These codons are each independently selected to encode tyrosine, serine, glycine, alanine, phenylalanine, tryptophan, histidine, proline, valine, aspartate, asparagine, threonine or arginine. Within the pool as whole, in each of these codon positions, codons for the listed amino acids are present at the following frequencies: 25% Tyr, 15% Ser, 15% Gly, 5% Ala, 5% Phe, 10% Trp, 5% His, 5% Pro, 5% Val, 3% Asp, 3% Asn, 3% Thr and 1% Arg.

The primer pool for a VL CDR3 length of 9 amino acids is referred to as K3-9. Each primer in pool K3-9 comprises the same conserved sequences at the 5' and 3' ends as the primers in pool K3-8, joined by one of multiple possible variant sequences. However, each variant sequence consists of four nucleotide triplet codons, i.e. 12 nucleotides in total. These codons are each independently selected to encode amino acids from the same list as in pool K3-8. Within the pool as a whole, codons for said amino acids are present at the same frequencies as in pool K3-8.

The primer pool for a VL CDR3 length of 10 amino acids is referred to as K3-10. Each primer in pool K3-10 comprises the same conserved sequences at the 5' and 3' ends as the primers in pool K3-8, joined by one of multiple possible variant sequences. However, each variant sequence consists of 5 nucleotide triplet codons, i.e. 15 nucleotides in total. These codons are each independently selected to encode amino acids from the same list as in pool K3-8. Within the pool as a whole, codons for said amino acids are present at the same frequencies as in pool K3-8.

The primer pool for a VL CDR3 length of 11 amino acids is referred to as K3-11. Each primer in pool K3-11 comprises the same conserved sequences at the 5' and 3' ends as the primers in pool K3-8, joined by one of multiple possible variant sequences. However, each variant sequence consists of 6 nucleotide triplet codons, i.e. 18 nucleotides in total. These codons are each independently selected to encode amino acids from the same list as in pool K3-8. Within the pool as a whole, codons for said amino acids are present at the same frequencies as in pool K3-8.

The primer pool for a VL CDR3 length of 12 amino acids is referred to as K3-12. Each primer in pool K3-12 comprises the same conserved sequences at the 5' and 3' ends as the primers in pool K3-8, joined by one of multiple possible variant sequences. However, each variant sequence consists of 7 nucleotide triplet codons, i.e. 21 nucleotides in total. These codons are each independently selected to encode amino acids from the same list as in pool K3-8. Within the pool as a whole, codons for said amino acids are present at the same frequencies as in pool K3-8.

As a further example, to produce a library of category AL2, different pools of primers may be designed to introduce the desired diversity into different positions of the various CDRs of the human germline sequences, as well as different lengths of CDR. Exemplary pools of primers which may be used to produce a library of category AL2 may be as follows (and as summarised in FIGS. 1C and D):

For VH CDR1, the same pool of primers was used as for libraries of category AL1, that is pool H1-1a. For VH CDR2, the same pool of primers was used as for libraries of category AL1, that is pool H2-1a.

For VH CDR3, ten different pools of primers were prepared, one pool for each of the permitted VH CDR3 lengths of 8, 9, 10, 11, 12, 13, 14, 15, 16 and 17 amino acids.

The primer pool for a VH CDR3 length of 8 amino acids is referred to as H3-8a. Each primer in pool H3-8a comprises a conserved sequence at the 5' end (CT GTA TAT TAT TGT GCG CGC—SEQ ID NO: 15) and a conserved sequence at the 3' end (WTK GAC TAT TGG GGC CAG G—SEQ ID NO: 16), joined together by one of multiple possible variant sequences. The variant sequences each consist of three nucleotide triplet codons, i.e. 9 nucleotides in total. These codons are each independently selected to encode tyrosine, serine, glycine, alanine, phenylalanine, tryptophan, histidine, proline, valine, aspartate, asparagines, threonine or arginine. Within the pool as whole, in each of these codon positions, codons for the listed amino acids are present at the following frequencies: of 25% Tyr, 15% Ser, 20% Gly, 5% Trp, 5% Ala, 5% Phe, 5% His, 5% Pro, 5% Val, 3% Asp, 3% Asn, 3% Thr and 1% Arg.

The primer pool for a VH CDR3 length of 9 amino acids is referred to as H3-9a. Each primer in pool H3-9a comprises the same conserved sequences at the 5' and 3' ends as the primers in pool H3-8a, joined by one of multiple possible variant sequences. However, each variant sequence consists of four nucleotide triplet codons, i.e. 12 nucleotides in total. These codons are each independently selected to encode amino acids from the same list as in pool H3-8a. Within the pool as a whole, codons for said amino acids are present at the same frequencies as in pool H3-8a.

The primer pool for a VH CDR3 length of 10 amino acids is referred to as H3-10a. Each primer in pool H3-10a comprises the same conserved sequences at the 5' and 3' ends as the primers in pool H3-8a, joined by one of multiple possible variant sequences. However, each variant sequence consists of 5 nucleotide triplet codons, i.e. 15 nucleotides in total. These codons are each independently selected to encode amino acids from the same list as in pool H3-8a. Within the pool as a whole, codons for said amino acids are present at the same frequencies as in pool H3-8a.

The primer pool for a VH CDR3 length of 11 amino acids is referred to as H3-11a. Each primer in pool H3-11a comprises the same conserved sequences at the 5' and 3' ends as the primers in pool H3-8a, joined by one of multiple possible variant sequences. However, each variant sequence consists of 6 nucleotide triplet codons, i.e. 18 nucleotides in total. These codons are each independently selected to encode amino acids from the same list as in pool H3-8a. Within the pool as a whole, codons for said amino acids are present at the same frequencies as in pool H3-8a.

The primer pool for a VH CDR3 length of 12 amino acids is referred to as H3-12a. Each primer in pool H3-12a comprises the same conserved sequences at the 5' and 3' ends as the primers in pool H3-8a, joined by one of multiple possible variant sequences. However, each variant sequence consists of 7 nucleotide triplet codons, i.e. 21 nucleotides in total. These codons are each independently selected to encode amino acids from the same list as in pool H3-8a. Within the pool as a whole, codons for said amino acids are present at the same frequencies as in pool H3-8a.

The primer pool for a VH CDR3 length of 13 amino acids is referred to as H3-13a. Each primer in pool H3-13a comprises the same conserved sequences at the 5' and 3' ends as the primers in pool H3-8a, joined by one of multiple possible variant sequences. However, each variant sequence consists of 8 nucleotide triplet codons, i.e. 24 nucleotides in total. These codons are each independently selected to encode amino acids from the same list as in pool H3-8a.

Within the pool as a whole, codons for said amino acids are present at the same frequencies as in pool H3-8a.

The primer pool for a VH CDR3 length of 14 amino acids is referred to as H3-14a. Each primer in pool H3-14a comprises the same conserved sequences at the 5' and 3' ends as the primers in pool H3-8a, joined by one of multiple possible variant sequences. However, each variant sequence consists of 9 nucleotide triplet codons, i.e. 27 nucleotides in total. These codons are each independently selected to encode amino acids from the same list as in pool H3-8a. Within the pool as a whole, codons for said amino acids are present at the same frequencies as in pool H3-8a.

The primer pool for a VH CDR3 length of 15 amino acids is referred to as H3-15a. Each primer in pool H3-15a comprises the same conserved sequences at the 5' and 3' ends as the primers in pool H3-8a, joined by one of multiple possible variant sequences. However, each variant sequence consists of 10 nucleotide triplet codons, i.e. 30 nucleotides in total. These codons are each independently selected to encode amino acids from the same list as in pool H3-8a. Within the pool as a whole, codons for said amino acids are present at the same frequencies as in pool H3-8a.

The primer pool for a VH CDR3 length of 16 amino acids is referred to as H3-16a. Each primer in pool H3-16a comprises the same conserved sequences at the 5' and 3' ends as the primers in pool H3-8a, joined by one of multiple possible variant sequences. However, each variant sequence consists of 11 nucleotide triplet codons, i.e. 33 nucleotides in total. These codons are each independently selected to encode amino acids from the same list as in pool H3-8a. Within the pool as a whole, codons for said amino acids are present at the same frequencies as in pool H3-8a.

The primer pool for a VH CDR3 length of 17 amino acids is referred to as H3-17a. Each primer in pool H3-17a comprises the same conserved sequences at the 5' and 3' ends as the primers in pool H3-8a, joined by one of multiple possible variant sequences. However, each variant sequence consists of 12 nucleotide triplet codons, i.e. 36 nucleotides in total. These codons are each independently selected to encode amino acids from the same list as in pool H3-8a. Within the pool as a whole, codons for said amino acids are present at the same frequencies as in pool H3-8a.

For VL CDR3, three different pools of primers were prepared, one pool for each of the permitted VL CDR3 lengths of 8, 9 and 10 amino acids.

The primer pool for a VL CDR3 length of 8 amino acids is referred to as K3-8a.

Each primer in pool K3-8a comprises a conserved sequence at the 5' end (GCA ACT TAT TAC TGT CAA CAG—SEQ ID NO: 17) and a conserved sequence at the 3' end (CYG YHC ACT TTT GGC CAG GGG AC—SEQ ID NO: 18), joined together by one of multiple possible variant sequences. The variant sequences each consist of three nucleotide triplet codons, i.e. 9 nucleotides in total. These codons are each independently selected to encode tyrosine, serine, glycine, alanine, phenylalanine, tryptophan, histidine, proline, valine, aspartate, asparagine, threonine or arginine. Within the pool as whole, in each of these codon positions, codons for the listed amino acids are present at the following frequencies: 25% Tyr, 15% Ser, 20% Gly, 5% Trp, 5% Ala, 5% Phe, 5% His, 5% Pro, 5% Val, 3% Asp, 3% Asn, 3% Thr and 1% Arg.

The primer pool for a VL CDR3 length of 9 amino acids is referred to as K3-9a. Each primer in pool K3-9a comprises the same conserved sequences at the 5' and 3' ends as the primers in pool K3-8a, joined by one of multiple possible variant sequences. However, each variant sequence consists of four nucleotide triplet codons, i.e. 12 nucleotides in total. These codons are each independently selected to encode amino acids from the same list as in pool K3-8a. Within the pool as a whole, codons for said amino acids are present at the same frequencies as in pool K3-8a.

The primer pool for a VL CDR3 length of 10 amino acids is referred to as K3-10a. Each primer in pool K3-10a comprises the same conserved sequences at the 5' and 3' ends as the primers in pool K3-8a, joined by one of multiple possible variant sequences. However, each variant sequence consists of 5 nucleotide triplet codons, i.e. 15 nucleotides in total. These codons are each independently selected to encode amino acids from the same list as in pool K3-8a. Within the pool as a whole, codons for said amino acids are present at the same frequencies as in pool K3-8a.

As a further example, to produce a library of category AL3, different pools of primers may be designed to introduce the desired diversity into different positions of the various CDRs of the human germline sequences, as well as different lengths of CDR. Exemplary pools of primers which may be used to produce a library of category AL3 may be as follows (and as summarised in FIGS. 1E and F):

For VH CDR1, the same pool of primers was used as for libraries of category AL1, that is pool H1-1a. For VH CDR2, the same pool of primers was used as for libraries of category AL2, that is pool H2-1a.

For VH CDR3, ten different pools of primers were prepared, one pool for each of the permitted VH CDR3 lengths of 8, 9, 10, 11, 12, 13, 14, 15, 16 and 17 amino acids.

The primer pool for a VH CDR3 length of 8 amino acids is referred to as H3-8b. Each primer in pool H3-8b comprises a conserved sequence at the 5' end (CT GTA TAT TAT TGT GCG CGC—SEQ ID NO: 15) and a conserved sequence at the 3' end (WTK GAC TAT TGG GGC CAG G—SEQ ID NO: 16), joined together by one of multiple possible variant sequences. The variant sequences each consist of three nucleotide triplet codons, i.e. 9 nucleotides in total. These codons are each independently selected to encode tyrosine, serine, glycine, alanine, phenylalanine, tryptophan, histidine, proline, valine, aspartate, asparagines, threonine or arginine. Within the pool as whole, in each of these codon positions, codons for the listed amino acids are present at the following frequencies: 20% Tyr, 15% Ser, 15% Gly, 5% Trp, 5% Ala, 5% Phe, 15% His, 5% Pro, 5% Val, 3% Asp, 3% Asn, 3% Thr and 1% Arg.

The primer pool for a VH CDR3 length of 9 amino acids is referred to as H3-9b. Each primer in pool H3-9b comprises the same conserved sequences at the 5' and 3' ends as the primers in pool H3-8b, joined by one of multiple possible variant sequences. However, each variant sequence consists of four nucleotide triplet codons, i.e. 12 nucleotides in total. These codons are each independently selected to encode amino acids from the same list as in pool H3-8b. Within the pool as a whole, codons for said amino acids are present at the same frequencies as in pool H3-8b.

The primer pool for a VH CDR3 length of 10 amino acids is referred to as H3-10b. Each primer in pool H3-10b comprises the same conserved sequences at the 5' and 3' ends as the primers in pool H3-8b, joined by one of multiple possible variant sequences. However, each variant sequence consists of 5 nucleotide triplet codons, i.e. 15 nucleotides in total. These codons are each independently selected to encode amino acids from the same list as in pool H3-8b. Within the pool as a whole, codons for said amino acids are present at the same frequencies as in pool H3-8b.

The primer pool for a VH CDR3 length of 11 amino acids is referred to as H3-11b. Each primer in pool H3-11b comprises the same conserved sequences at the 5' and 3' ends as the primers in pool H3-8b, joined by one of multiple possible variant sequences. However, each variant sequence consists of 6 nucleotide triplet codons, i.e. 18 nucleotides in total. These codons are each independently selected to encode amino acids from the same list as in pool H3-8b. Within the pool as a whole, codons for said amino acids are present at the same frequencies as in pool H3-8b.

The primer pool for a VH CDR3 length of 12 amino acids is referred to as H3-12b. Each primer in pool H3-12b comprises the same conserved sequences at the 5' and 3' ends as the primers in pool H3-8b, joined by one of multiple possible variant sequences. However, each variant sequence consists of 7 nucleotide triplet codons, i.e. 21 nucleotides in total. These codons are each independently selected to encode amino acids from the same list as in pool H3-8b. Within the pool as a whole, codons for said amino acids are present at the same frequencies as in pool H3-8b.

The primer pool for a VH CDR3 length of 13 amino acids is referred to as H3-13b. Each primer in pool H3-13b comprises the same conserved sequences at the 5' and 3' ends as the primers in pool H3-8b, joined by one of multiple possible variant sequences. However, each variant sequence consists of 8 nucleotide triplet codons, i.e. 24 nucleotides in total. These codons are each independently selected to encode amino acids from the same list as in pool H3-8b. Within the pool as a whole, codons for said amino acids are present at the same frequencies as in pool H3-8b.

The primer pool for a VH CDR3 length of 14 amino acids is referred to as H3-14b. Each primer in pool H3-14b comprises the same conserved sequences at the 5' and 3' ends as the primers in pool H3-8b, joined by one of multiple possible variant sequences. However, each variant sequence consists of 9 nucleotide triplet codons, i.e. 27 nucleotides in total. These codons are each independently selected to encode amino acids from the same list as in pool H3-8b. Within the pool as a whole, codons for said amino acids are present at the same frequencies as in pool H3-8b.

The primer pool for a VH CDR3 length of 15 amino acids is referred to as H3-15b. Each primer in pool H3-15b comprises the same conserved sequences at the 5' and 3' ends as the primers in pool H3-8b, joined by one of multiple possible variant sequences. However, each variant sequence consists of 10 nucleotide triplet codons, i.e. 30 nucleotides in total. These codons are each independently selected to encode amino acids from the same list as in pool H3-8b. Within the pool as a whole, codons for said amino acids are present at the same frequencies as in pool H3-8b.

The primer pool for a VH CDR3 length of 16 amino acids is referred to as H3-16b. Each primer in pool H3-16b comprises the same conserved sequences at the 5' and 3' ends as the primers in pool H3-8b, joined by one of multiple possible variant sequences. However, each variant sequence consists of 11 nucleotide triplet codons, i.e. 33 nucleotides in total. These codons are each independently selected to encode amino acids from the same list as in pool H3-8b. Within the pool as a whole, codons for said amino acids are present at the same frequencies as in pool H3-8b.

The primer pool for a VH CDR3 length of 17 amino acids is referred to as H3-17b. Each primer in pool H3-17b comprises the same conserved sequences at the 5' and 3' ends as the primers in pool H3-8b, joined by one of multiple possible variant sequences. However, each variant sequence consists of 12 nucleotide triplet codons, i.e. 36 nucleotides in total. These codons are each independently selected to encode amino acids from the same list as in pool H3-8b. Within the pool as a whole, codons for said amino acids are present at the same frequencies as in pool H3-8b.

For VL CDR3, three different pools of primers were prepared, one pool for each of the permitted VL CDR3 lengths of 8, 9 and 10 amino acids.

The primer pool for a VL CDR3 length of 8 amino acids is referred to as K3-8b. Each primer in pool K3-8b comprises a conserved sequence at the 5' end (GCA ACT TAT TAC TGT CAA CAG—SEQ ID NO: 17) and a conserved sequence at the 3' end (CYG YHC ACT TTT GGC CAG GGG AC—SEQ ID NO: 18), joined together by one of multiple possible variant sequences. The variant sequences each consist of three nucleotide triplet codons, i.e. 9 nucleotides in total. These codons are each independently selected to encode tyrosine, serine, glycine, alanine, phenylalanine, tryptophan, histidine, proline, valine, aspartate, asparagine, threonine or arginine. Within the pool as whole, in each of these codon positions, codons for the listed amino acids are present at the following frequencies: 25% Tyr, 15% Ser, 20% Gly, 5% Trp, 5% Ala, 5% Phe, 5% His, 5% Pro, 5% Val, 3% Asp, 3% Asn, 3% Thr and 1% Arg.

The primer pool for a VL CDR3 length of 9 amino acids is referred to as K3-9b. Each primer in pool K3-9b comprises the same conserved sequences at the 5' and 3' ends as the primers in pool K3-8b, joined by one of multiple possible variant sequences. However, each variant sequence consists of four nucleotide triplet codons, i.e. 12 nucleotides in total. These codons are each independently selected to encode amino acids from the same list as in pool K3-8b. Within the pool as a whole, codons for said amino acids are present at the same frequencies as in pool K3-8b.

The primer pool for a VL CDR3 length of 10 amino acids is referred to as K3-10b. Each primer in pool K3-10b comprises the same conserved sequences at the 5' and 3' ends as the primers in pool K3-8b, joined by one of multiple possible variant sequences. However, each variant sequence consists of 5 nucleotide triplet codons, i.e. 15 nucleotides in total. These codons are each independently selected to encode amino acids from the same list as in pool K3-8b. Within the pool as a whole, codons for said amino acids are present at the same frequencies as in pool K3-8b.

For VL CDR1, a single pool of primers was prepared, referred to as K1-1. Each primer in pool K1-1 comprises a conserved sequence at the 5' end (ACT TGC CGG GCA AGT CAG—SEQ ID NO: 19) and a conserved sequence at the 3' end (TAT TTA AAT TGG TAT CAG C—SEQ ID NO: 20), joined together by one of multiple possible variant sequences. The variant sequences each consist of four nucleotide triplet codons, i.e. 12 nucleotides in total. The second codon (nucleotides 4, 5, 6) is ATT. The third codon (nucleotides 7, 8, 9) is AGN. N indicates that the third base in the third codon is independently selected from A, T/U, C or G, each of which is equally preferred. Thus, within the pool as a whole, codons for serine and arginine are equally preferred in said third codon position. The first and fourth codons are each independently selected to encode tyrosine, serine, glycine, asparagine or alanine. Within the pool as whole, in each of these codon positions, codons for tyrosine, serine, glycine, asparagine and alanine are present at equal frequencies.

For VL CDR2, a single pool of primers was prepared, referred to as K2-1. Each primer in pool K2-1 comprises a conserved sequence at the 5' end (C CCT AAG CTC CTG ATC TAT—SEQ ID NO: 21) and a conserved sequence at the 3' end (GCA TCC AGT TTG CAA AGT—SEQ ID NO: 22), joined together by one of multiple possible variant sequences. The variant sequences each consist of one triplet codon, i.e. 3 nucleotides in total. This codon is independently selected to encode to encode tyrosine, serine, glycine, asparagine or alanine Within the pool as whole, in this codon position, codons for tyrosine, serine, glycine, asparagine and alanineare present at equal frequencies.

Whichever pool of primers of used, application of the above-described methods will result in a library of nucleic acid molecules in which each nucleic acid molecule encodes a different antibody molecule. The nucleic acid molecules are present within bacteriophage or phagemid vectors, and thus may be used to transform further *E. coli*, resulting in expression of the diverse antibody molecule products. That is, a library of antibody molecules of the invention is produced as a phage display library.

In accordance with the above, the present invention also provides a method of producing a library of antibody molecules. A preferred method comprises:

(i) preparing a population of bacteriophage or phagemid vectors containing a library of nucleic acid molecules according to the invention; and (ii) infecting a population of bacterial cells with said population of vectors under conditions which permit phage reproduction, optionally wherein said cells are *E. coli*.

Methods of Selecting Antibodies/Uses of Libraries

A library of antibody molecules according to the invention may be used in a method of selecting an antibody molecule that binds to an antigen. Such a library may be used to screen for an antibody molecule that binds to an antigen. Typically, a method of selecting an antibody molecule that binds to an antigen comprises:

(i) providing a library of antibody molecules according to the invention;

(ii) contacting said library with said antigen;

(iii) selecting an antibody molecule which binds to the antigen.

Such a method may include an additional step between steps (i) and (ii), in which the library is contacted with an antigen which is not of interest to remove non-specific antibody molecules. For example, antibody molecules reactive with streptavidin may be removed by initially incubating a library with streptavidin immobilised on a solid surface such as a bead.

An exemplary selection protocol for an antibody phage display library is as follows:
1. Negative selection. Solid support (e.g. magnetic beads) and/or negative selection proteins (non-target antigens) are added to the antibody phage display library. Phages that bind directly to the support or the non-target antigens are removed and the remaining phage stock is used for positive selection against the target antigen.
2. Positive selection. The output from step 1 is incubated with the target antigen, and target antigen binding phages are rescued.
3. The target binding phages are then amplified (in *E. coli*) and subjected to at least one further round of selection (positive or negative). Usually, the stringency (wash, antigen concentration etc.) is increased for each selection step.
4. The out-put from the selection rounds are then screened in a high throughput screening (HTS) system to identify individual target specific clones The antigen is typically a therapeutic target, such as a target associated with cancer. The target may be an immunomodulatory receptor, a checkpoint inhibitor, a growth factor receptor, an angiogenesis receptor, or a tumor antigen. Preferred targets include CD40, LTBR, Her2, VEGFR, CD30, CD40L, CXCR4, CD25, LIGHT, CD95, DR4, HLA-DR, PD-1, PD-L1, CD137, GITR, OX40, CTLA-4, CD27, HVEM, LtBR, LAG3, CD20, 5T4, MAGE, FGF, VEGF, Angiopoietin, MMP, Dll4, ErbB, EGFR, CEA, MUC-1, ras, p53, AFP and ephrin type-A receptor 2. CD40 and LTBR are particularly preferred.

The pH in a tumour microenvironment in vivo is significantly more acidic than that of healthy tissues. Ranges for tumours are reported as around pH 6.5 to 7.2 or 6.6 to 7.0, as compared to 7.2 to 7.4 for healthy tissues. This acidity is primarily due to anaerobic glycolysis in tumor regions subjected to short-term or long-term hypoxia as a result of poorly organized vasculature with diminished chaotic blood flow, and aerobic glycolysis (the Warburg effect), a common cancer phenotypic property in which the glycolytic metabolic pathways are used even in the presence of oxygen. Accordingly it is desirable to generate antibody molecules that specifically bind to their target at lower pH. Such an antibody molecule could advantageously be used for the treatment of tumors with lowered pH, since it would bind more effectively within the tumour microenvironment than in systemic circulation. As such it would have a greater therapeutic window and could thus result in lower toxicity.

AL3 has been designed to contain a very high histidine ratio (15%) in VH CDR3. In contrast, the typical histidine content of a VH CDR3 loop is roughly 2%. Histidine is an amino acid that typically is protonated at lower pH (pKa 2 6, pI 7.6) but mainly deprotonated and neutral at physiological pH (7.4). This amino acid would thus confer different binding properties at low and normal pH. A large proportion of histidines in the binding site should enable generation of antibody molecules that have one type of binding site at low pH (in tumors) and another at normal pH. The design of AL3 allows for selection of antibodies with a higher affinity for tumor-related targets at lower pH. By having a significantly higher affinity at lower pH, tumor specificity will be increased. This may also improve tumor penetration since the target affinity will increase as the pH gradient decreases inside the tumor. This effect may be enhanced by charge, since the antibody molecule will be more positively charged at lower pH, thereby "trapping" the antibody molecule inside the tumor. In short, libraries of category AL3 are particularly suitable for selecting antibody molecules with higher affinity at low pH, which improves tumor specificity, penetration and distribution.

An antibody molecule selected in accordance with a method of the invention may be isolated and sequenced, or a nucleic acid molecule encoding said antibody molecule may be isolated and sequenced, in order to determine the VH and VL domain sequences of said antibody molecule. Sequencing of amino acids or nucleic acids may be carried out according to any suitable method, such as set out in the Examples.

The present invention also provides for an antibody molecule, preferably a human IgG antibody molecule, which comprises the VH and VL domain sequences of an antibody molecule selected in accordance with a method of the invention. Such an antibody may be formulated in a composition, which optionally comprises a pharmaceutically acceptable diluent or carrier.

EXAMPLES

Example 1

Three different phage display libraries of scFV antibody molecules were designed and produced, designated category AL1, category AL2 and category AL3. Each library was constructed essentially as described by Sidhu S., and Fellouse F. (Chapter 8 "Making antibodies in bacteria"; Making and using antibodies. A practical handbook. CRC Press 2006; Pages 157-180; Print ISBN: 978-0-8439-3528-0)

The positions indicated below (IMGT numbering) in the various CDRs were targeted for the introduction of diversity in the libraries:

VH CDR1: positions 35, 36, 37, 38 and 40 (solvent accessible)
VH CDR2: positions 55, 57, 58, 59, 62, 63, 64 and 66 (solvent accessible)
VH CDR3: positions 107, 108, 109, 110, 111, 111.1, 111.2, 111.3, 111.4, 112.5, 112.4, 112.3, 112.2, 112.1, 112, 113 and 114 (solvent accessible), and position 115 (not solvent accessible)
VL CDR1: positions 28, 36 and 37 (solvent accessible)
VL CDR2: position 56 (solvent accessible)
VL CDR3: positions 107, 108, 109, 110, 112, 113 and 114 (solvent accessible), and positions 115 and 116 (not solvent accessible)

The designs of the three libraries may then be summarised as follows:

AL1

Diversity was introduced at positions in VH CDR1, 2 and 3, and VL CDR3 only.

Positions 35, 36, 37, 38 and 40 in VH CDR1 and positions 55, 57, 58, 59, 62, 63, 64 and 66 in VH CDR2 were independently restricted to tyrosine, serine and glycine in equal ratio. The applied diversity mimics the natural diversity found in CDRH1 and CDRH2, and the importance of these residues for antigen recognition has been demonstrated in several studies.

Positions 107, 108, 109, 110, 111, 111.1, 111.2, 111.3, 111.4, 112.5, 112.4, 112.3, 112.2, 112.1, 112, 113 and 114 in VH CDR3 and positions 107, 108, 109, 110, 112, 113 and 114 in VL CDR3 were independently restricted to the following amino acids at the frequencies indicated: 25% Tyr, 15% Ser, 15% Gly, 5% Ala, 5% Phe, 10% Trp, 5% His, 5% Pro, 5% Val, 3% Asp, 3% Asn, 3% Thr and 1% Arg.

Position 115 of VH CDR3 was independently restricted to phenylalanine, isoleucine, leucine and methionine in equal ratios. Position 115 of VL CDR3 was independently restricted to phenylalanine and leucine in equal ratios. Position 116 of VL CDR 3 was independently restricted to histidine, proline, leucine, tyrosine, serine and phenylalanine in equal ratios. The amino acids in these positions residues may affect the conformation of the CDR loops, but are generally not involved in antigen contact.

The lengths of the CDR-H3 loop and CDR-L3 loop were allowed to vary from 8 to 22 and 8 to 12, respectively.

AL2

Diversity was introduced at positions in VH CDR1, 2 and 3, and VL CDR3 only.

Positions 35, 36, 37, 38 and 40 in VH CDR1 and positions 55, 57, 58, 59, 62, 63, 64 and 66 in VH CDR2 were independently restricted to tyrosine, serine and glycine in equal ratio. The applied diversity mimics the natural diversity found in CDRH1 and CDRH2, and the importance of these residues for antigen recognition has been demonstrated in several studies.

Positions 107, 108, 109, 110, 111, 111.1, 111.2, 112.2, 112.1, 112, 113 and 114 in VH CDR3 and positions 107, 108, 109, 110, 112, 113 and 114 in VL CDR3 were independently restricted to the following amino acids at the frequencies indicated: 25% Tyr, 15% Ser, 20% Gly, 5% Ala, 5% Phe, 5% Trp, 5% His, 5% Pro, 5% Val, 3% Asp, 3% Asn, 3% Thr and 1% Arg. The lower Trp frequency will produce high affinity antibodies with high stability.

Position 115 of VH CDR3 was independently restricted to phenylalanine, isoleucine, leucine and methionine in equal ratios. Position 115 of VL CDR3 was independently restricted to phenylalanine and leucine in equal ratios. Position 116 of VL CDR 3 was independently restricted to histidine, proline, leucine, tyrosine, serine and phenylalanine in equal ratios. The amino acids in these positions residues may affect the conformation of the CDR loops, but are generally not involved in antigen contact.

The lengths of the CDR-H3 loop and CDR-L3 loop were allowed to vary from 8 to 17 and 8 to 12, respectively.

AL3

Diversity was introduced at positions in all six CDRs.

Positions 35, 36, 37, 38 and 40 in VH CDR1 and positions 55, 57, 58, 59, 62, 63, 64 and 66 in VH CDR2 were independently restricted to tyrosine, serine and glycine in equal ratio. The applied diversity mimics the natural diversity found in VH CDR1 and VH CDR2, and the importance of these residues for antigen recognition has been demonstrated in several studies.

Positions 107, 108, 109, 110, 111, 111.1, 111.2, 112.2, 112.1, 112, 113 and 114 in VH CDR3 were independently restricted to the following amino acids at the frequencies indicated: 20% Tyr, 15% Ser, 15% Gly, 5% Trp, 5% Ala, 5% Phe, 15% His, 5% Pro, 5% Val, 3% Asp, 3% Asn, 3% Thr and 1% Arg. The lower Trp frequency will produce high affinity antibodies with high stability. The higher His frequency will contribute to producing antibodies with high affinity and stability at lower pH.

Positions 107, 108, 109, 110, 112, 113 and 114 in VL CDR3 were independently restricted to the following amino acids at the frequencies indicated: 25% Tyr, 15% Ser, 20% Gly, 5% Ala, 5% Phe, 5% Trp, 5% His, 5% Pro, 5% Val, 3% Asp, 3% Asn, 3% Thr and 1% Arg. The lower Trp frequency will produce high affinity antibodies with high stability.

Position 115 of VH CDR3 was independently restricted to phenylalanine, isoleucine, leucine and methionine in equal ratios. Position 115 of VL CDR3 was independently restricted to phenylalanine and leucine in equal ratios. Position 116 of VL CDR 3 was independently restricted to histidine, proline, leucine, tyrosine, serine and phenylalanine in equal ratios. The amino acids in these positions residues may affect the conformation of the CDR loops, but are generally not involved in antigen contact.

Positions 28 and 37 in VL CDR1 were independently restricted to tyrosine, serine, glycine, asparagine and alanine in equal ratio. Position 36 of VL CDR1 was independently restricted to serine and arginine in equal ratio. Position 56 in VL CDR2 was independently restricted to tyrosine, serine, glycine, asparagine and alanine in equal ratio. The applied diversity mimics the natural diversity found in VL CDR1 and VL CDR2, and the importance of these residues for antigen recognition has been demonstrated in several studies.

The lengths of the CDR-H3 loop and CDR-L3 loop were allowed to vary from 8 to 17 and 8 to 12, respectively.

Library Production

Firstly, a phagemid vector was generated, with sequences arranged as in the following schematic:

VH—linker—VL—(optional additional sequences, e.g. FLAG-tag)—pIII pIII is the gene for the pIII coat protein, VH is the nucleic acid encoding SEQ ID NO: 3, and VL is the nucleic acid encoding SEQ ID NO: 6. Single colony dut–/ung– bacteria harboring the phagemid vector were inoculated into 2YT medium containing M13K07 helper phage (New England Biolabs, Beverly, Mass.)) (1010 pfu/ml) and antibiotics. Following overnight incubation and a standard PEG precipitation procedure, single stranded DNA (ssDNA) was purified using QIAprep Spin M13 Kit (Qiagen, Valencia, Calif.). Double stranded DNA (dsDNA) reactions were prepared by mixing mutagenic oligos, phosphorylated by T4 nucleotide kinase (NEB), and the ssDNA followed by the addition of T4 DNA ligase (NEB) and T7 and DNA ligase (NEB) in buffers described in detail by Sidhu S., and Fellouse F. (Chapter 8 "Making antibodies in bacteria"; Making and using antibodies. A practical handbook. CRC Press 2006; Pages 157-180; Print ISBN: 978-0-8439-3528-0). The mutagenic oligos were designed to introduce stop codons in the VH and/or VL sequences at sites targeted for the introduction of diversity, according to the Kunkel method (Methods of Enzymology 1987, 154, 367-382 and Sidhu et al., Methods of Enzymology 2000, 328, 353-363). The reaction mixes were electroplated into dut+/ung+ bacteria, and cells transformed were grown overnight in the presence of M13-VCS helper phage to produce phage particles that encapsulated the phagemid vector having stop codons introduced.

The resulting phagemid vectors comprise one of the following nucleic acid sequences:

```
For AL1:
                                            (SEQ ID NO: 25)
GAGGTGCAGCTGTTGGAGAGCGGGGGAGGCTTGGTACAGCCTGGGGGGTC

CCTGCGCCTCTCCTGTGCAGCCAGCGGATTCACCTTTAGCAGCTATGCCA

TGAGCTGGGTCCGCCAGGCTCCAGGGAAGGGGCTGGAGTGGGTCTCAGCT

ATTAGTGGTAGTGGTGGTAGCACATACTATGCAGACTCCGTGAAGGGCCG

GTTCACCATCTCCCGTGACAATTCCAAGAACACGCTGTATCTGCAAATGA

ACAGCCTGCGTGCCGAGGACACGGCTGTATATTATTGTGCGCGCTAATAA

TAATACTTTGACTATTGGGGCCAGGGAACCCTGGTCACCGTCTCCTCAGG

TGGAGGCGGTTCAGGCGGAGGTGGATCCGGCGGTGGCGGATCGGACATCC

AGATGACCCAGTCTCCATCCTCCCTGAGCGCATCTGTAGGAGACCGCGTC

ACCATCACTTGCCGGGCAAGTCAGAGCATTAGCAGCTATTTAAATTGGTA

TCAGCAGAAACCAGGGAAAGCCCCTAAGCTCCTGATCTATGCTGCATCCA

GTTTGCAAAGTGGGGTCCCATCACGTTTCAGTGGCAGTGGAAGCGGGACA

GATTTCACTCTCACCATCAGCAGTCTGCAACCTGAAGATTTTGCAACTTA

TTACTGTCAACAGAGTTAATAATAATACACTTTTGGCCAGGGGACCAAGC

TGGAGATCAAA

For AL2 and 3
                                            (SEQ ID NO: 26)
GAGGTGCAGCTGTTGGAGAGCGGGGGAGGCTTGGTACAGCCTGGGGGGTC

CCTGCGCCTCTCCTGTGCAGCCAGCGGATTCACCTTTAGCAGCTATGCCA

TGAGCTGGGTCCGCCAGGCTCCAGGGAAGGGGCTGGAGTGGGTCTCAGCT

ATTAGTGGTAGTGGTGGTAGCACATACTATGCAGACTCCGTGAAGGGCCG

GTTCACCATCTCCCGTGACAATTCCAAGAACACGCTGTATCTGCAAATGA

ACAGCCTGCGTGCCGAGGACACGGCTGTATATTATTGTGCGCGCTAATGA

TAATGACTCGAGTACTTTGACTATTGGGGCCAGGGAACCCTGGTCACCGT
```

-continued
```
CTCCTCAGGTGGAGGCGGTTCAGGCGGAGGTGGATCCGGCGGTGGCGGAT

CGGACATCCAGATGACCCAGTCTCCATCCTCCCTGAGCGCATCTGTAGGA

GACCGCGTCACCATCACTTGCCGGGCAAGTCAGAGCATTAGCAGCTATTT

AAATTGGTATCAGCAGAAACCAGGGAAAGCCCCTAAGCTCCTGATCTATG

CTGCATCCAGTTTGCAAAGTGGGGTCCCATCACGTTTCAGTGGCAGTGGA

AGCGGGACAGATTTCACTCTCACCATCAGCAGTCTGCAACCTGAAGATTT

TGCAACTTATTACTGTCAACAGAGTTACAGTACCCCTTATACTTTTGGCC

AGGGGACCAAGCTGGAGATCAAA
```

Phagemid vector comprising one of nucleic acid sequences SEQ ID NO: 25 or 26 was then used as the starting template for generation of the libraries themselves, by repeating the above steps of the Kunkel method, but with diversity being introduced using different tailored mixtures of mutagenic oligos. The mutagenic oligonucleotides for each library category are summarised in FIG. 1. For libraries of category AL2 and AL3, five sub reaction mixtures were prepared. The reactions differed in the mutagenic oligonucleotides for VH CDR3, where each sub-reaction contained the appropriate oligos to produce a VH CDR3 length of (i) 8 or 9 amino acids; (ii) 10 or 11 amino acids; (iii) 12 or 13 amino acids; (iv) 14 or 15 amino acids; and (v) 16 or 17 amino acids, according to IMGT nomenclature. For a library of category AL1, additional sub-reaction mixtures were prepared with the appropriate oligos to produce a VH CDR3 length of 18 to 22 amino acids. In each library, the reaction mixtures were electroporated into dut+/ung+ bacteria, and cells transformed were grown overnight in the presence of M13-VCS helper phage to produce phage particles that encapsulate the phagemid DNA with introduced diversity, and thus display diverse scFV fragments. Each library contained $1\times10^{10}$ unique members as measured by the number of obtained transformants. The quality of the libraries was confirmed by sequencing.

Example 2

Selection Based on Target Antigens

Phage display libraries of category AL1, AL2 and AL3 in ScFV format were tested separately in selection experiments using two different antigens, CD40 and LTBR. The two test antigens are members of the TNF receptor superfamily.

The general procedure for selecting the binding antibody clones against the two targets were as follows:

Phage stocks were initially pre-selected against streptavidin coated magnetic beads (Dynabeads M-280, Invitrogen, #112.06D) in order to remove potential streptavidin binders. An excess of Beriglobin (ZBL Behring) or Orencia (Bristol-Myer Squibb) was present in all selection rounds in order to remove presumptive Fc-binders. Selections against biotinylated Fc-fused CD40 or LTBR (R&D Systems, #629-LR) were performed for 5 rounds starting at 100 nM and decreasing by 10 times per selection round. Bovine serum albumin (BSA, #) was included as a blocking agent throughout the selection procedure at a final concentration of 1%.

The pre-selected ScFv phage library was incubated with and biotinylated CD40 or LTBR for at least 1 h and thereafter, phage expressing CD40 or LTBR binding ScFv were captured on streptavidin beads. The complex was washed repeatedly with increased stringency. Trypsin (Lonza, #17-161E) digestion was used to elute binding phage from the streptavidin beads and Aprotinin Roche,

1023662401) was added. Eluted phage was used for infection of log-phase XL1-Blue cells (originating from #200228, Stratagene) for 30 min at 37° C. and infected cells were spread on QTrays (2×YT Agar/Ampicillin/Tetracycline/Glucose 50 µg/mL, 10 µg/mL, 1%) and incubated over-night at 37° C.

The following day, Qtrays were scraped, the bacteria diluted and allowed to grow to log phase. Phage stock was made by infecting log phase XL1-Blue with an 20× excess of helper phage M13K07 (New England Biolabs, N0315S), the expression of phage surface displayed ScFv was induced by the addition of ITPG and the induced cultures were grown over-night at 30° C. Amplified phage stock was precipitated by adding ¼ volume PEG/NaCl (25%/2.5M) prior to the next selection round. The number of phage eluted as well as the number of input phage in the selection rounds was monitored by titration (i. e infection of log phase XL1-Blue cells and counting of colony forming units).

Screening and Sequence Determination of scFV Antibody Clones Specific for CD40

Screening for antibody clones binding to the two test targets and subsequent sequencing were performed. CD40 binders were identified by comparing binding to target (CD40) and non-target (Orencia) coated plates in an ELISA assay at a single dilution of antibody. The protocol for the ELISA assays was as follows:

Single clones from the later selection rounds were picked and cultured in 96-well deep-well plates and grown overnight. The following day, new plates were inoculated with the over-night cultures and grown in low glucose media (2×YT/Ampicillin/Tetracycline/Glucose 50 µg/mL, 10 µg/mL, 0.05%) and 20× excess of M13K07 helper phage (New England Biolabs, N0315S) was added when the cultures reached log-phase. The expression of phage surface displayed ScFv was induced by the addition of ITPG. The next day, supernatants were collected and used in phage-ELISA. An empty vector was used as negative control and a phagemid encoding a known CD40 or LTBR binder was included as a positive control. High binding plates (Greiner #781074) were coated with CD40 or LTBR (R&D Systems #629-LR) at 0.1-1 µg/ml, or with Beriglobin or Orencia (0.5 µg/ml). Coated wells were blocked and the phage containing supernatants were added at a single dilution. Binding phage was detected with anti M13-HRP (GE, 27-9421-01) and Super Signal Pico Chemiluminescent (ThermoScientific, #37069) was used as substrate. Orencia and Beriglobin were included to exclude the possibility of selecting phages that bind to Fc-regions. At the highest phage concentration tested, the response to Beriglobin was in all samples less that 4% of the corresponding response to CD40. The binding to target and non-target plates was compared. Antibodies which had a ratio of binding to target versus binding to non-target of greater than 20 were considered to be specific binders for CD40.

The identified antibody clones were sequenced and their CDRs (complementary determining regions) were determined. The sequences of the total number of identified antibody clones versus the number of identified unique sequences encoding antibody clones were analysed. The results are shown in the following table. All three libraries generated specific binding antibody clones to CD40-antigen.

| Proportion of unique sequences isolated from antibody libraries. | | |
|---|---|---|
| Library | Clones analysed, total | Unique clones (% of total) |
| AL1 | 409 | 90 (22%) |
| AL2 | 307 | 78 (25%) |
| AL3 | 52 | 22 (42%) |

The following table shows the total number of clones identified as specific binders, compared to the total number of isolated clones from libraries AL1 and AL2. Both libraries produced high ratios of specific binders to CD40.

| Proportion of specific antibody binders isolated from antibody libraries. | | |
|---|---|---|
| Library | Clones analysed | Specific clones (%) |
| AL1 | 21 | 15 (71%) |
| AL2 | 78 | 70 (90%) |

DNA sequencing of the specific binders was performed according to standard methods at MWG (Germany) using forward and reverse primers. CDR regions were determined using the IMGT system. Alignment tools are available at www.imgt.org.

Cloning to Full Antibody Format and Further Assaying for Binding to CD40

The antibody clones identified as specific binders for CD40 were re-cloned into full IgG format employing two expression vectors for VH and VL respectively. Plasmids were prepared and the constructs were verified by sequencing. 293 Freestyle cells (Invitrogen, #R790-07) were transfected with the plasmids VH and VL and after 6 days, supernatants were collected and the expressed full IgG were purified on Protein A FF columns (GE Healthcare). The purified antibodies were analysed using SDS-PAGE, A280 and HPLC. The sequences encoding for CDR1-3 were determined. Binding to CD40 was determined in a B cell proliferation assay, a CD40 binding ELISA, and a CD40L competition assay.

B cell proliferation is measured because the binding of agonistic anti-CD40 antibody to CD40 on B cells results in B cell activation and proliferation, homeotypic aggregation and up-regulation of surface markers. For the assay, B-cells were isolated by leucocyte filter from two donors and incubated with the purified full IgG molecules or other stimulant for three days. Human mega-CD40L (Alexis Biochemical, #ALX-522-110) was used as a positive control. The B-cell proliferation was measured with Cell-titer glow (Promega, #G7571) measuring the ATP content in the cells.

For the CD40 binding ELISA, high binding flat bottom LIA plates (Greiner #655074) were coated with Fc-fused CD40 (Ancell, #504-820) at 0.05 µg/ml, and milk powder were used at 3% for blocking and at 1% for dilution. The antibodies to be tested were added in serial dilutions starting at 2000 ng/ml and detection was carried out using HRP conjugated goat anti human Ig-Fc (Jackson ImmunoResearch, #109-035-098) and Super Signal Pico Chemiluminescent (ThermoScientific, #37069) was used as substrate.

For the CD40L competition assay, Wehi cells transfected with human CD40 were washed in FACS buffer (PBS, 0.5% FBS and 0.05% Sodium Azide) and preincubated with anti-CD40 antibodies (25 µg/ml) or an isotype control (human IgG1, 25 µg/ml) for 30 min at +4° C. Human CD40L (0.5 µg/ml) was added to the cells without washing and incubated for 30 minutes at +4° C. The cells were washed and a secondary antibody anti-HA-PE, detecting CD40L, was added for another 15 minutes. The cells were washed three times before FACS analyses. The assay determines whether or not the antibodies compete with CD40L for binding to CD40.

The results of the B cell proliferation assay, CD40 binding ELISA and CD40L competition assay for the isolated CD40 antibody clones are shown in the following table.

|  | Antibody | In vitro data | | |
|---|---|---|---|---|
|  |  | EC50 B cell (ug/ml) | EC50 ELISA (ng/ml) | CD40L BLOCK |
| AL1 | B03 | 0.44 |  | ND |
|  | D10 | 0.32 |  | +++ |
|  | F08 |  |  | ND |
|  | G01 |  |  | ND |
|  | 1107/1108 | 0.7 | 34 | +++ |
| AL2 | 1132/1133 | 2.2 | 280 | + |
|  | 1134/1135 | 1.0 | 25 | − |
|  | 1136/1137 | 1.0 | 1400 | + |
|  | 1138/1135 | 4.5 | 970 | − |
|  | 1140/1135 | 0.4 | 310 | − |
|  | 1142/1135 | 1.5 | 560 | − |
|  | 1146/1147 | 3.6 | 580 | + |
|  | 1148/1149 | 2.3 | 2200 | + |
|  | 1150/1151 | 0.9 | 41 | ND |

The following table shows the diversity in sequences for VH CDRs 1, 2 and 3 and VL CDR3

Figure 2:
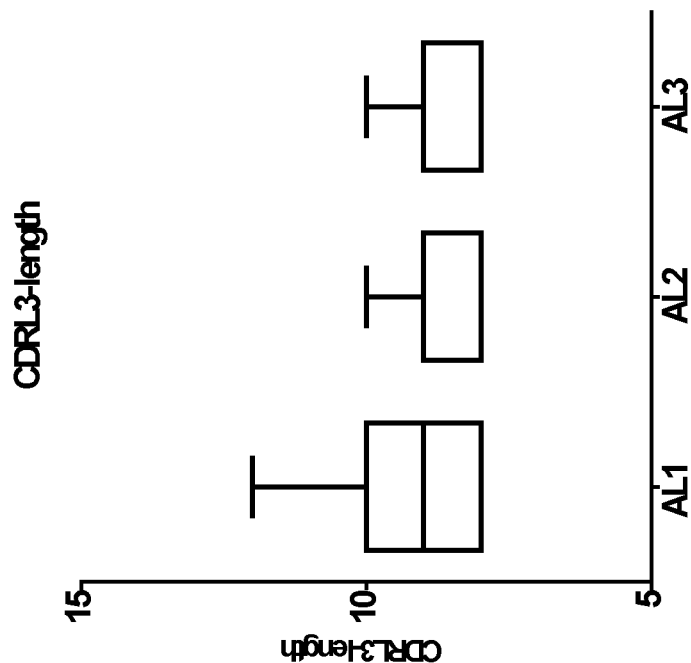
FIG. 2 shows the variation in lengths of the CDR3 loops for the VH (top half) and VL (bottom half) domains of anti-CD40 antibody clones from libraries AL1, 2 and 3.
Figure 2:
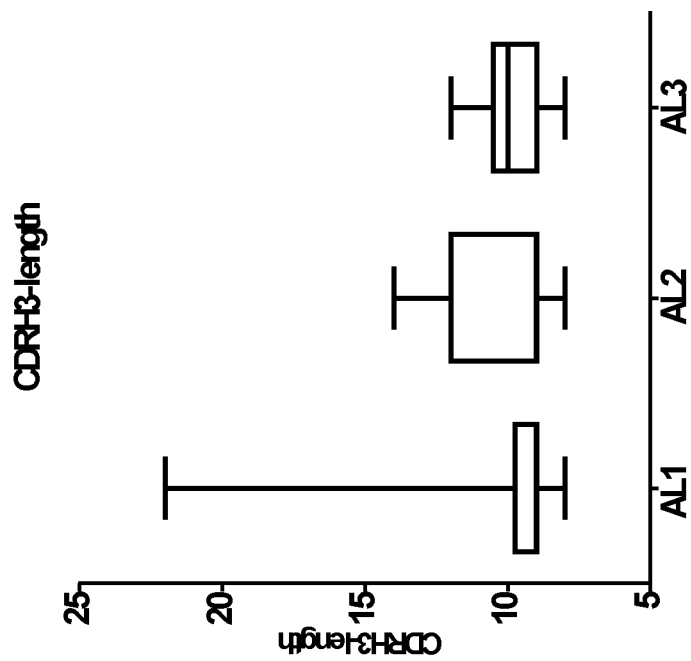

The loop lengths of VH CDR3 and VL CDR3 of each selected anti-CD40 antibody from AL1, AL2 and AL3 were also analysed. The results for AL1, AL2 and AL3 are shown in FIG. 2. The results for AL1 and AL2 are also summarised in the following table. The VH CDR3 lengths are shorter than those typically obtained from naturally occurring human IgG.

|  | Antibody | CDR length | |
|---|---|---|---|
|  |  | CDRL3 | CDRH3 |
| AL1 | B03 | 10 | 9 |
|  | D10 | 9 | 9 |
|  | F08 | 9 | 9 |
|  | G01 | 9 | 9 |
|  | 1107/1108 | 9 | 9 |
| AL2 | 1132/1133 | 9 | 10 |
|  | 1134/1135 | 9 | 12 |
|  | 1136/1137 | 10 | 9 |
|  | 1138/1135 | 9 | 12 |
|  | 1140/1135 | 9 | 12 |
|  | 1142/1135 | 9 | 12 |
|  | 1146/1147 | 9 | 9 |
|  | 1148/1149 | 9 | 9 |
|  | 1150/1151 | 9 | 10 |

Screening and Sequence Determination of scFV Antibody Clones Specific for LTBR

The AL1 ScFV antibody library was tested for binders to LTBR. The LTBR binding antibody clones were screened, selected and cloned into full IgG format as described above for CD40. Binding to LTBR for two selected anti-LTBR antibody clones was characterized by surface plasmon resonance (SPR). SPR analysis of LTBR antibodies was performed according to standard protocols. The LTBRhfc (R&Dsystems, USA) was immobilized to the BIAcore sensorchip, CM5, using conventional amine coupling. The anti-LTBR antibodies (serially diluted ⅓ from 1-0.012 nM)

|  | Antibody | VH CDR1 | | | | | VH CDR2 | | | | | | | VH CDR3 | | | | | | | |
|---|---|---|---|---|---|---|---|---|---|---|---|---|---|---|---|---|---|---|---|---|---|
|  |  | 35 | 36 | 37 | 38 | 40 | 55 | 57 | 58 | 59 | 62 | 63 | 64 | 66 | 107 | 108 | 109 | 110 | 112 | 113 | 114 | 115 |
| AL1 | B03 | S | S | Y | A | S | A | S | G | S | G | G | S | Y | S | V | W |  |  |  | G | F |
|  | D10 | S | S | Y | A | S | S | S | G | S | G | G | S | Y | R | V | W |  |  |  | G | F |
|  | F08 | G | Y | S | Y | S | G | S | S | S | S | S | S | Y | W | Y | H |  |  |  | S | F |
|  | G01 | G | S | S | Y | S | A | S | G | S | G | G | S | Y | H | Y | Y |  |  |  | A | F |
|  | 1107/1108 | S | S | Y | A | S | A | S | G | S | G | G | S | Y | R | V | W |  |  |  | G | F |
| AL2 | 1132/1133 | S | S | Y | A | S | G | G | S | Y | G | G | G | Y | Y | V | N |  |  | F | G | M |
|  | 1134/1135 | S | S | Y | A | S | S | Y | S | G | G | G | S | Y | G | P | A | Y | S | S | F | F |
|  | 1136/1137 | S | S | Y | A | S | A | S | G | S | G | G | S | Y | Y | V | F |  |  |  | G | I |
|  | 1138/1135 | S | S | Y | A | S | A | S | G | S | G | G | S | Y | G | F | V | Y | S | S | Y | I |
|  | 1140/1135 | S | S | Y | A | S | A | S | G | S | G | G | S | Y | G | P | V | Y | S | S | V | F |
|  | 1142/1135 | S | S | Y | A | S | A | S | G | S | G | G | S | Y | G | P | A | Y | S | T | V | L |
|  | 1146/1147 | S | S | Y | A | S | A | S | G | S | G | G | S | Y | R | V | F |  |  |  | G | F |
|  | 1148/1149 | S | S | Y | A | S | A | S | G | S | G | G | S | Y | A | V | F |  |  |  | G | F |
|  | 1150/1151 | S | S | Y | A | S | G | G | G | S | S | S | Y | S | Y | Y | S |  |  | Y | H | M |

|  | Antibody | VL CDR3 | | | | | | |
|---|---|---|---|---|---|---|---|---|
|  |  | 107 | 108 | 109 | 113 | 114 | 115 | 116 |
| AL1 | B03 | G | Y | H | V | W | L | Y |
|  | D10 | Y | G | V |  | Y | P | F |
|  | F08 | H | G | W |  | H | P | F |
|  | G01 | H | T |  |  | Y | P | F |
|  | 1107/1108 | Y | G | V |  | Y | P | F |
| AL2 | 1132/1133 | Y | G | R |  | N | P | P |
|  | 1134/1135 | S | Y | S |  | T | P | Y |
|  | 1136/1137 | A | Y | Y | A | G | L | F |
|  | 1138/1135 | S | Y | S |  | T | P | Y |
|  | 1140/1135 | S | Y | S |  | T | P | Y |
|  | 1142/1135 | S | Y | S |  | T | P | Y |
|  | 1146/1147 | Y | Y | Y |  | Y | P | F |
|  | 1148/1149 | A | Y | Y |  | F | P | H |
|  | 1150/1151 | Y | G | S |  | A | P | P | were analysed for binding in HBS-P (GE, BR-1003-68) at a flow rate of 30 μl/min at 37° C. and pH 7.3. The association was followed for 3 minutes and the dissociation for 10 minutes. Regeneration was performed twice using 50 mM NaOH for 30 seconds. The kinetic parameters and the affinity constants were calculated using BIAevaluation 4.1 software, and samples were run, using the Biacore 3000 instrument according to manufacturer's protocols.

The determined kinetic parameters/affinity constants and the lengths of VH CDR3 and VL CDR3 for the selected anti-LTBR antibodies are shown in the following table:

| Antibody | CDR length | | Kinetic paramenters | | |
|---|---|---|---|---|---|
| | CDRL3 | CDRH3 | ka (1/Ms) | kd (1/s) | KD (M) |
| LTBR-1 | 8 | 8 | 3.39E+06 | 4.55E−04 | 1.43E−10 |
| LTBR-3 | 9 | 11 | 2.23E+06 | 1.58E−03 | 7.34E−10 |

The following table shows the diversity in sequences of VH CDRs 1, 2 and 3 and VL CDR3 for the selected anti-LTBR antibodies

| | VH CDR1 | | | | | VH CDR2 | | | | | | | VH CDR3 | | |
|---|---|---|---|---|---|---|---|---|---|---|---|---|---|---|---|
| Antibody | 35 | 36 | 37 | 38 | 40 | 55 | 57 | 58 | 59 | 62 | 63 | 64 | 66 | 107 | 108 | 109 |
| LTBR-1 | G | S | Y | S | S | S | S | S | Y | Y | G | G | S | G | A | |
| LTBR-3 | S | S | Y | A | S | A | S | G | S | G | G | S | Y | Y | Y | W |

| | VH CDR3 | | | | VL CDR3 | | | | | |
|---|---|---|---|---|---|---|---|---|---|---|
| Antibody | 110 | 113 | 114 | 115 | 107 | 108 | 109 | 114 | 115 | 116 |
| LTBR-1 | | | Y | L | Y | Y | | F | P | F |
| LTBR-3 | G | W | Y | F | G | W | W | Y | P | L |

The analysed antibody clones obtained exhibited affinity for LTBR in the sub-nanomolar range and fast on-rates. The isolated CDR1-3s were of variable sequence, and the loops of H3 and L3, were of various sizes. Thus, the antibodies have high affinity for a clinically relevant target.

Example 3

Analysis of Amino Acid Preferences. Sequence Diversity and Lengths

The amino acid preferences and sequence diversity of antibody clones from libraries AL1. AL2 and AL3 were further analysed. Selection against human CD40 or LTBR was performed as described in Example 2. The CD40 binding antibodies obtained by phage display selection were screened using ELISA and isolated CD40 antibody clones were sequenced.

Figure 3A:
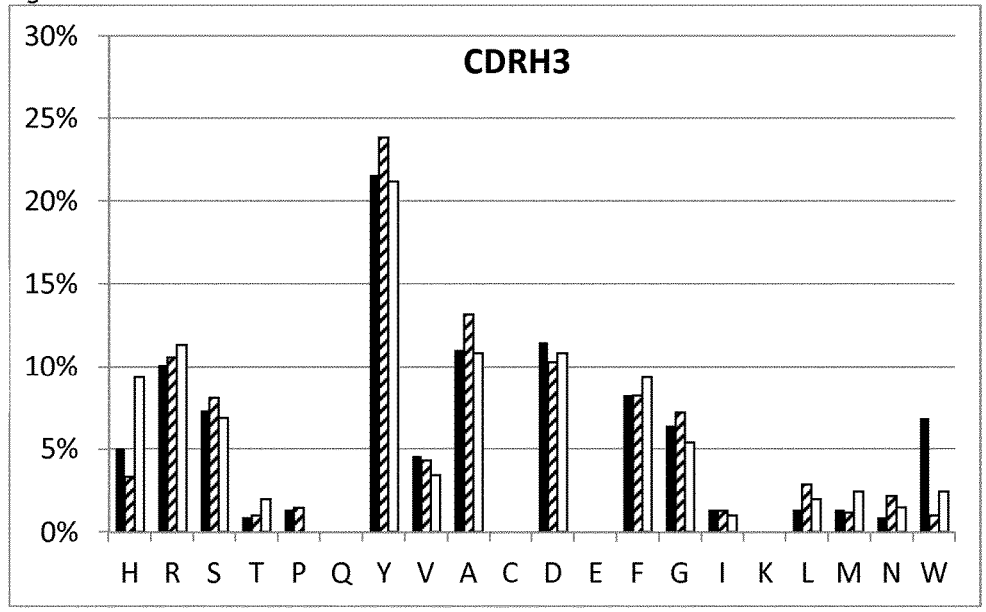
FIG. 3 shows the average overall frequency of each amino acid in (A) the VH CDR3 loops and (B) the VL CDR3 loops for isolated anti-CD40 antibody clones from library AL1 (filled bars), AL2 (hatched bars) and AL3 (empty bars)
Figure 3B:
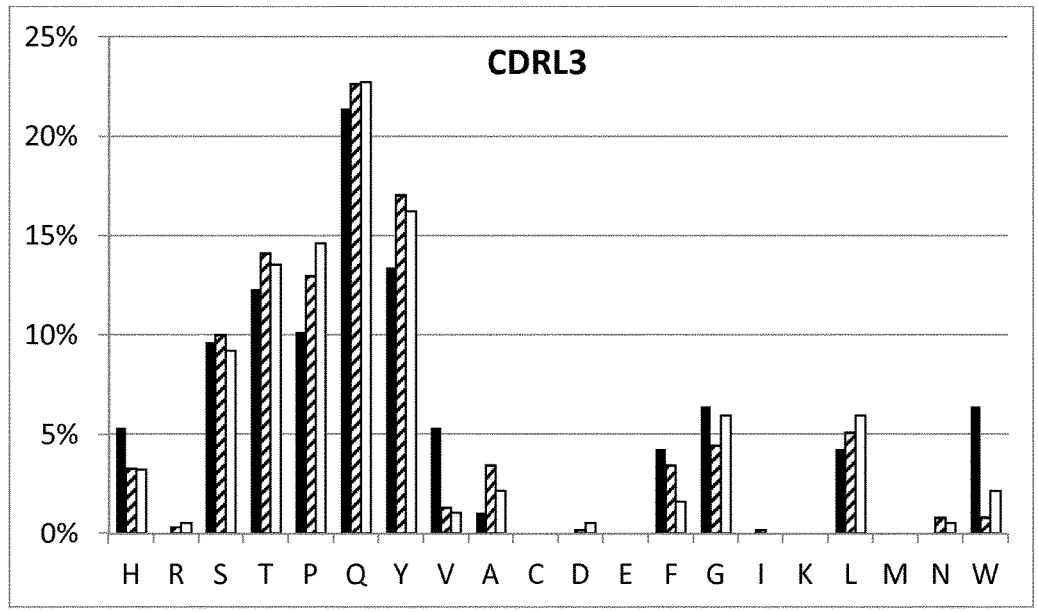

The frequency of each amino acid in the VH CDR3 and VL CDR3 of each antibody was calculated. The average amino acid frequencies for the antibodies from each library are shown in FIGS. 3A and B. As shown in FIG. 3A. the mean frequency of histidine in the VH CDR3 loops of antibodies selected from library AL3 is high relative to the natural repertoire (Birtalan et al. 2008. *J. Molecular Biology*). This is consistent with the designed high level of histidine for VH CDR3 of AL3. High histidine levels are advantageous for antibodies which will be used to treat cancers since the pH in a tumour microenvironment in vivo is significantly more acidic than that of healthy tissues.

The amino acid preferences in the CDRs of the selected antibodies were further analysed by investigating the frequency of each amino acid in each individual position of designed variability. The results are shown in the following tables. The amino acid usage varies between the libraries AL1, AL2 and AL3.

Results for Anti-CD40 Antibodies Selected from AL1
Amino Acid Frequency (%) in Each Position of Designed Diversity in VH CDR1

| Amino acid | IMGT number | | | | | |
|---|---|---|---|---|---|---|
| | 35 | 36 | 37 | 38 | 39 | 40 |
| H | 0.0 | 0.0 | 0.0 | 0.0 | 0.0 | 0.0 |
| R | 0.0 | 0.0 | 0.0 | 0.0 | 0.0 | 0.0 |

-continued

| Amino acid | IMGT number | | | | | |
|---|---|---|---|---|---|---|
| | 35 | 36 | 37 | 38 | 39 | 40 |
| S | 65.0 | 70.0 | 35.0 | 5.0 | 0.0 | 80.0 |
| T | 0.0 | 0.0 | 0.0 | 0.0 | 0.0 | 0.0 |
| P | 0.0 | 0.0 | 0.0 | 0.0 | 0.0 | 0.0 |
| Q | 0.0 | 0.0 | 0.0 | 0.0 | 0.0 | 0.0 |
| Y | 5.0 | 20.0 | 50.0 | 45.0 | 0.0 | 0.0 |
| V | 0.0 | 0.0 | 0.0 | 0.0 | 0.0 | 0.0 |
| A | 0.0 | 0.0 | 0.0 | 40.0 | 0.0 | 0.0 |
| C | 0.0 | 0.0 | 0.0 | 0.0 | 0.0 | 0.0 |
| D | 0.0 | 0.0 | 5.0 | 0.0 | 0.0 | 0.0 |
| E | 0.0 | 0.0 | 0.0 | 0.0 | 0.0 | 0.0 |
| F | 0.0 | 0.0 | 0.0 | 0.0 | 0.0 | 0.0 |
| G | 30.0 | 10.0 | 10.0 | 10.0 | 0.0 | 20.0 |
| I | 0.0 | 0.0 | 0.0 | 0.0 | 0.0 | 0.0 |
| K | 0.0 | 0.0 | 0.0 | 0.0 | 0.0 | 0.0 |
| L | 0.0 | 0.0 | 0.0 | 0.0 | 0.0 | 0.0 |
| M | 0.0 | 0.0 | 0.0 | 0.0 | 100 | 0.0 |
| N | 0.0 | 0.0 | 0.0 | 0.0 | 0.0 | 0.0 |
| W | 0.0 | 0.0 | 0.0 | 0.0 | 0.0 | 0.0 |

Amino Acid Frequency (%) in Each Position of Designed Diversity in VH CDR2

| Amino acid | IMGT number | | | | | | | | | |
|---|---|---|---|---|---|---|---|---|---|---|
| | 55 | 56 | 57 | 58 | 59 | 62 | 63 | 64 | 65 | 66 |
| H | 0.0 | 0.0 | 0.0 | 0.0 | 0.0 | 0.0 | 0.0 | 0.0 | 0.0 | 0.0 |
| R | 0.0 | 0.0 | 0.0 | 0.0 | 0.0 | 0.0 | 0.0 | 0.0 | 0.0 | 0.0 |
| S | 20.0 | 0.0 | 90.0 | 30.0 | 80.0 | 20.0 | 25.0 | 70.0 | 0.0 | 10.0 |
| T | 0.0 | 0.0 | 0.0 | 0.0 | 0.0 | 0.0 | 0.0 | 0.0 | 100 | 0.0 |
| P | 0.0 | 0.0 | 0.0 | 0.0 | 0.0 | 0.0 | 0.0 | 0.0 | 0.0 | 0.0 |
| Q | 0.0 | 0.0 | 0.0 | 0.0 | 0.0 | 0.0 | 0.0 | 0.0 | 0.0 | 0.0 |
| Y | 15.0 | 0.0 | 5.0 | 5.0 | 10.0 | 0.0 | 5.0 | 15.0 | 0.0 | 90.0 |
| V | 0.0 | 0.0 | 0.0 | 0.0 | 0.0 | 0.0 | 0.0 | 0.0 | 0.0 | 0.0 |
| A | 50.0 | 0.0 | 0.0 | 0.0 | 0.0 | 0.0 | 0.0 | 0.0 | 0.0 | 0.0 |
| C | 0.0 | 0.0 | 0.0 | 0.0 | 0.0 | 0.0 | 0.0 | 0.0 | 0.0 | 0.0 |
| D | 0.0 | 0.0 | 0.0 | 0.0 | 5.0 | 0.0 | 0.0 | 5.0 | 0.0 | 0.0 |
| E | 0.0 | 0.0 | 0.0 | 0.0 | 0.0 | 0.0 | 0.0 | 0.0 | 0.0 | 0.0 |
| F | 0.0 | 0.0 | 0.0 | 0.0 | 0.0 | 0.0 | 0.0 | 0.0 | 0.0 | 0.0 |
| G | 15.0 | 0.0 | 5.0 | 65.0 | 5.0 | 80.0 | 70.0 | 10.0 | 0.0 | 0.0 |
| I | 0.0 | 100 | 0.0 | 0.0 | 0.0 | 0.0 | 0.0 | 0.0 | 0.0 | 0.0 |
| K | 0.0 | 0.0 | 0.0 | 0.0 | 0.0 | 0.0 | 0.0 | 0.0 | 0.0 | 0.0 |
| L | 0.0 | 0.0 | 0.0 | 0.0 | 0.0 | 0.0 | 0.0 | 0.0 | 0.0 | 0.0 |
| M | 0.0 | 0.0 | 0.0 | 0.0 | 0.0 | 0.0 | 0.0 | 0.0 | 0.0 | 0.0 |
| N | 0.0 | 0.0 | 0.0 | 0.0 | 0.0 | 0.0 | 0.0 | 0.0 | 0.0 | 0.0 |
| W | 0.0 | 0.0 | 0.0 | 0.0 | 0.0 | 0.0 | 0.0 | 0.0 | 0.0 | 0.0 |

Amino Acid Frequency (%) in Each Position of Designed Diversity in VH CDR3

| Am Ac | IMGT number | | | | | | | | | | | | | | | | | |
|---|---|---|---|---|---|---|---|---|---|---|---|---|---|---|---|---|---|---|
| | 107 | 108 | 109 | 110 | 111 | 111.1 | 111.2 | 111.3 | 111.4 | 112.5 | 112.4 | 112.3 | 112.2 | 112.1 | 112 | 113 | 114 | 115 |
| H | 5.0 | 0.0 | 29.4 | 20.0 | 0.0 | 0.0 | 0.0 | 0.0 | 0.0 | 0.0 | 33.3 | 33.3 | 0.0 | 0.0 | 0.0 | 0.0 | 10.5 | 0.0 |
| R | 10.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| S | 25.0 | 15.0 | 5.9 | 20.0 | 33.3 | 0.0 | 0.0 | 0.0 | 0.0 | 0.0 | 0.0 | 0.0 | 0.0 | 33.3 | 0.0 | 20.0 | 15.8 | 0.0 |
| T | 0.0 | 0.0 | 0.0 | 0.0 | 0.0 | 0.0 | 0.0 | 0.0 | 0.0 | 50.0 | 0.0 | 0.0 | 0.0 | 0.0 | 0.0 | 20.0 | 0.0 | 0.0 |
| P | 0.0 | 5.0 | 0.0 | 0.0 | 0.0 | 0.0 | 0.0 | 0.0 | 0.0 | 0.0 | 0.0 | 0.0 | 33.3 | 0.0 | 0.0 | 0.0 | 5.3 | 0.0 |
| Q | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| Y | 20.0 | 20.0 | 23.5 | 40.0 | 0.0 | 66.7 | 33.3 | 33.3 | 50.0 | 0.0 | 0.0 | 0.0 | 66.7 | 0.0 | 50.0 | 40.0 | 10.5 | 0.0 |
| V | 10.0 | 30.0 | 0.0 | 0.0 | 0.0 | 0.0 | 0.0 | 0.0 | 50.0 | 0.0 | 0.0 | 0.0 | 0.0 | 0.0 | 0.0 | 0.0 | 5.3 | 0.0 |
| A | 0.0 | 0.0 | 5.9 | 0.0 | 0.0 | 0.0 | 0.0 | 0.0 | 0.0 | 0.0 | 0.0 | 0.0 | 0.0 | 0.0 | 50.0 | 0.0 | 5.3 | 0.0 |
| C | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| D | 0.0 | 10.0 | 0.0 | 0.0 | 66.7 | 0.0 | 0.0 | 33.3 | 0.0 | 0.0 | 0.0 | 0.0 | 0.0 | 0.0 | 0.0 | 0.0 | 0.0 | 0.0 |
| E | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| F | 0.0 | 5.0 | 17.6 | 20.0 | 0.0 | 0.0 | 0.0 | 0.0 | 0.0 | 0.0 | 0.0 | 0.0 | 0.0 | 0.0 | 0.0 | 0.0 | 5.3 | 60.0 |
| G | 10.0 | 5.0 | 0.0 | 0.0 | 0.0 | 33.3 | 0.0 | 0.0 | 0.0 | 0.0 | 0.0 | 33.3 | 0.0 | 0.0 | 0.0 | 20.0 | 42.1 | 0.0 |
| I | 0.0 | 0.0 | 0.0 | 0.0 | 0.0 | 0.0 | 0.0 | 33.3 | 0.0 | 0.0 | 0.0 | 0.0 | 0.0 | 0.0 | 0.0 | 0.0 | 0.0 | 10.0 |
| K | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| L | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 15.0 |
| M | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 15.0 |
| N | 0.0 | 10.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| W | 20.0 | 0.0 | 17.6 | 0.0 | 0.0 | 0.0 | 66.7 | 0.0 | 0.0 | 50.0 | 66.7 | 33.3 | 0.0 | 66.7 | 0.0 | 0.0 | 0.0 | 0.0 |

Amino Acid Frequency (%) in Each Position of Designed Diversity in VL CDR3

| Amino acid | IMGT number | | | | | | | | |
|---|---|---|---|---|---|---|---|---|---|
| | 107 | 108 | 109 | 110 | 112 | 113 | 114 | 115 | 116 |
| H | 15.0 | 0.0 | 21.4 | 0.0 | 0.0 | 0.0 | 15.0 | 0.0 | 5.0 |
| R | 0.0 | 0.0 | 0.0 | 0.0 | 0.0 | 0.0 | 0.0 | 0.0 | 0.0 |
| S | 15.0 | 35.0 | 21.4 | 25.0 | 0.0 | 25.0 | 5.0 | 0.0 | 5.0 |
| T | 0.0 | 5.0 | 0.0 | 0.0 | 0.0 | 0.0 | 10.0 | 0.0 | 0.0 |
| P | 0.0 | 0.0 | 0.0 | 0.0 | 0.0 | 12.5 | 0.0 | 75.0 | 15.0 |
| Q | 0.0 | 0.0 | 0.0 | 0.0 | 0.0 | 0.0 | 0.0 | 0.0 | 0.0 |
| Y | 15.0 | 20.0 | 28.6 | 25.0 | 0.0 | 0.0 | 45.0 | 0.0 | 20.0 |
| V | 5.0 | 5.0 | 14.3 | 0.0 | 100 | 37.5 | 10.0 | 0.0 | 0.0 |
| A | 5.0 | 0.0 | 0.0 | 0.0 | 0.0 | 0.0 | 5.0 | 0.0 | 0.0 |
| C | 0.0 | 0.0 | 0.0 | 0.0 | 0.0 | 0.0 | 0.0 | 0.0 | 0.0 |
| D | 0.0 | 0.0 | 0.0 | 0.0 | 0.0 | 0.0 | 0.0 | 0.0 | 0.0 |
| E | 0.0 | 0.0 | 0.0 | 0.0 | 0.0 | 0.0 | 0.0 | 0.0 | 0.0 |
| F | 0.0 | 0.0 | 0.0 | 0.0 | 0.0 | 0.0 | 0.0 | 0.0 | 40.0 |
| G | 15.0 | 25.0 | 7.1 | 0.0 | 0.0 | 25.0 | 5.0 | 0.0 | 0.0 |
| I | 0.0 | 0.0 | 0.0 | 0.0 | 0.0 | 0.0 | 0.0 | 0.0 | 0.0 |
| K | 0.0 | 0.0 | 0.0 | 0.0 | 0.0 | 0.0 | 0.0 | 0.0 | 0.0 |
| L | 0.0 | 0.0 | 0.0 | 0.0 | 0.0 | 0.0 | 0.0 | 25.0 | 15.0 |
| M | 0.0 | 0.0 | 0.0 | 0.0 | 0.0 | 0.0 | 0.0 | 0.0 | 0.0 |
| N | 0.0 | 0.0 | 0.0 | 0.0 | 0.0 | 0.0 | 0.0 | 0.0 | 0.0 |
| W | 30.0 | 10.0 | 7.1 | 50.0 | 0.0 | 0.0 | 5.0 | 0.0 | 0.0 |

Results for Anti-CD40 Antibodies Selected from AL2
Amino Acid Frequency (%) in Each Position of Designed Diversity in VH CDR1

| Amino acid | IMGT number | | | | | |
|---|---|---|---|---|---|---|
| | 35 | 36 | 37 | 38 | 39 | 40 |
| H | 1.4 | 1.4 | 0.0 | 1.4 | 0.0 | 0.0 |
| R | 0.0 | 0.0 | 0.0 | 0.0 | 0.0 | 0.0 |
| S | 68.1 | 66.7 | 24.6 | 10.1 | 0.0 | 76.8 |
| T | 0.0 | 0.0 | 0.0 | 0.0 | 0.0 | 1.4 |
| P | 1.4 | 0.0 | 0.0 | 0.0 | 0.0 | 0.0 |
| Q | 0.0 | 0.0 | 0.0 | 0.0 | 0.0 | 0.0 |
| Y | 8.7 | 27.5 | 71.0 | 26.1 | 0.0 | 0.0 |
| V | 0.0 | 0.0 | 0.0 | 0.0 | 0.0 | 0.0 |
| A | 0.0 | 0.0 | 0.0 | 50.7 | 0.0 | 0.0 |
| C | 0.0 | 0.0 | 0.0 | 0.0 | 0.0 | 0.0 |
| D | 0.0 | 0.0 | 0.0 | 0.0 | 0.0 | 0.0 |
| E | 0.0 | 0.0 | 0.0 | 0.0 | 0.0 | 0.0 |
| F | 0.0 | 0.0 | 0.0 | 0.0 | 0.0 | 0.0 |
| G | 20.3 | 4.3 | 4.3 | 11.6 | 0.0 | 21.7 |
| I | 0.0 | 0.0 | 0.0 | 0.0 | 0.0 | 0.0 |
| K | 0.0 | 0.0 | 0.0 | 0.0 | 0.0 | 0.0 |
| L | 0.0 | 0.0 | 0.0 | 0.0 | 0.0 | 0.0 |
| M | 0.0 | 0.0 | 0.0 | 0.0 | 100.0 | 0.0 |
| N | 0.0 | 0.0 | 0.0 | 0.0 | 0.0 | 0.0 |
| W | 0.0 | 0.0 | 0.0 | 0.0 | 0.0 | 0.0 |

Amino Acid Frequency (%) in Each Position of Designed Diversity in VH CDR2

| Amino acid | IMGT number | | | | | | | | | |
|---|---|---|---|---|---|---|---|---|---|---|
| | 55 | 56 | 57 | 58 | 59 | 62 | 63 | 64 | 65 | 66 |
| H | 0.0 | 0.0 | 0.0 | 0.0 | 1.4 | 0.0 | 0.0 | 1.4 | 0.0 | 0.0 |
| R | 0.0 | 0.0 | 0.0 | 0.0 | 0.0 | 0.0 | 0.0 | 0.0 | 0.0 | 0.0 |
| S | 18.8 | 0.0 | 66.7 | 27.5 | 68.1 | 18.8 | 22.1 | 72.5 | 0.0 | 10.1 |
| T | 0.0 | 0.0 | 0.0 | 0.0 | 0.0 | 0.0 | 0.0 | 0.0 | 100.0 | 0.0 |
| P | 0.0 | 0.0 | 0.0 | 1.4 | 1.4 | 0.0 | 0.0 | 0.0 | 0.0 | 0.0 |
| Q | 0.0 | 0.0 | 0.0 | 0.0 | 0.0 | 0.0 | 0.0 | 0.0 | 0.0 | 0.0 |
| Y | 11.6 | 0.0 | 4.3 | 13.0 | 8.7 | 13.0 | 10.3 | 10.1 | 0.0 | 84.1 |
| V | 0.0 | 0.0 | 0.0 | 0.0 | 0.0 | 0.0 | 0.0 | 0.0 | 0.0 | 0.0 |
| A | 42.0 | 0.0 | 0.0 | 0.0 | 0.0 | 0.0 | 0.0 | 0.0 | 0.0 | 0.0 |
| C | 0.0 | 0.0 | 0.0 | 0.0 | 0.0 | 0.0 | 0.0 | 0.0 | 0.0 | 0.0 |
| D | 0.0 | 0.0 | 0.0 | 0.0 | 0.0 | 0.0 | 1.5 | 0.0 | 0.0 | 0.0 |
| E | 0.0 | 0.0 | 0.0 | 0.0 | 0.0 | 0.0 | 0.0 | 0.0 | 0.0 | 0.0 |
| F | 0.0 | 0.0 | 0.0 | 0.0 | 0.0 | 0.0 | 0.0 | 0.0 | 0.0 | 0.0 |
| G | 27.5 | 0.0 | 29.0 | 58.0 | 20.3 | 68.1 | 66.2 | 15.9 | 0.0 | 5.8 |
| I | 0.0 | 100.0 | 0.0 | 0.0 | 0.0 | 0.0 | 0.0 | 0.0 | 0.0 | 0.0 |
| K | 0.0 | 0.0 | 0.0 | 0.0 | 0.0 | 0.0 | 0.0 | 0.0 | 0.0 | 0.0 |
| L | 0.0 | 0.0 | 0.0 | 0.0 | 0.0 | 0.0 | 0.0 | 0.0 | 0.0 | 0.0 |
| M | 0.0 | 0.0 | 0.0 | 0.0 | 0.0 | 0.0 | 0.0 | 0.0 | 0.0 | 0.0 |
| N | 0.0 | 0.0 | 0.0 | 0.0 | 0.0 | 0.0 | 0.0 | 0.0 | 0.0 | 0.0 |
| W | 0.0 | 0.0 | 0.0 | 0.0 | 0.0 | 0.0 | 0.0 | 0.0 | 0.0 | 0.0 |

Amino Acid Frequency (%) in Each Position of Designed Diversity in VH CDR3

| Amino acid | IMGT number | | | | | | | | | |
|---|---|---|---|---|---|---|---|---|---|---|
| | 107 | 108 | 109 | 110 | 111 | 112 | 112.1 | 113 | 114 | 115 |
| H | 8.7 | 2.9 | 11.1 | 0.0 | 0.0 | 5.6 | 0.0 | 18.2 | 1.5 | 0.0 |
| R | 2.9 | 0.0 | 1.6 | 0.0 | 0.0 | 0.0 | 0.0 | 0.0 | 1.5 | 0.0 |
| S | 14.5 | 10.1 | 15.9 | 15.0 | 0.0 | 55.6 | 0.0 | 21.2 | 13.2 | 0.0 |
| T | 4.3 | 0.0 | 0.0 | 0.0 | 0.0 | 5.6 | 0.0 | 9.1 | 0.0 | 0.0 |
| P | 0.0 | 14.5 | 0.0 | 0.0 | 0.0 | 0.0 | 0.0 | 0.0 | 0.0 | 0.0 |
| Q | 0.0 | 0.0 | 0.0 | 0.0 | 0.0 | 0.0 | 0.0 | 0.0 | 0.0 | 0.0 |
| Y | 23.2 | 30.4 | 23.8 | 65.0 | 50.0 | 11.1 | 33.3 | 18.2 | 29.4 | 0.0 |
| V | 2.9 | 20.3 | 6.3 | 0.0 | 0.0 | 11.1 | 0.0 | 0.0 | 11.8 | 0.0 |
| A | 7.2 | 0.0 | 11.1 | 0.0 | 25.0 | 0.0 | 33.3 | 3.0 | 10.3 | 0.0 |
| C | 0.0 | 0.0 | 0.0 | 0.0 | 0.0 | 0.0 | 0.0 | 0.0 | 0.0 | 0.0 |
| D | 0.0 | 1.4 | 0.0 | 0.0 | 25.0 | 0.0 | 0.0 | 0.0 | 0.0 | 0.0 |
| E | 0.0 | 0.0 | 0.0 | 0.0 | 0.0 | 0.0 | 0.0 | 0.0 | 0.0 | 0.0 |
| F | 7.2 | 2.9 | 15.9 | 15.0 | 0.0 | 0.0 | 33.3 | 6.1 | 2.9 | 46.4 |
| G | 21.7 | 4.3 | 3.2 | 5.0 | 0.0 | 5.6 | 0.0 | 24.2 | 29.4 | 0.0 |
| I | 0.0 | 0.0 | 0.0 | 0.0 | 0.0 | 0.0 | 0.0 | 0.0 | 0.0 | 13.0 |
| K | 0.0 | 0.0 | 0.0 | 0.0 | 0.0 | 0.0 | 0.0 | 0.0 | 0.0 | 0.0 |
| L | 0.0 | 0.0 | 0.0 | 0.0 | 0.0 | 0.0 | 0.0 | 0.0 | 0.0 | 29.0 |
| M | 0.0 | 0.0 | 0.0 | 0.0 | 0.0 | 0.0 | 0.0 | 0.0 | 0.0 | 11.6 |
| N | 0.0 | 13.0 | 7.9 | 0.0 | 0.0 | 5.6 | 0.0 | 0.0 | 0.0 | 0.0 |
| W | 7.2 | 0.0 | 3.2 | 0.0 | 0.0 | 0.0 | 0.0 | 0.0 | 0.0 | 0.0 |

Amino Acid Frequency (%) in Each Position of Designed Diversity in VL CDR3

| Amino acid | IMGT number | | | | | | |
|---|---|---|---|---|---|---|---|
| | 107 | 108 | 109 | 113 | 114 | 115 | 116 |
| H | 15.9 | 2.9 | 0.0 | 0.0 | 2.9 | 0.0 | 7.2 |
| R | 0.0 | 0.0 | 4.1 | 0.0 | 0.0 | 0.0 | 0.0 |
| S | 26.1 | 15.9 | 44.9 | 0.0 | 8.7 | 0.0 | 5.8 |
| T | 0.0 | 1.4 | 0.0 | 0.0 | 23.2 | 0.0 | 0.0 |
| P | 7.2 | 2.9 | 2.0 | 11.1 | 10.1 | 73.9 | 17.4 |
| Q | 0.0 | 0.0 | 0.0 | 0.0 | 0.0 | 0.0 | 0.0 |
| Y | 26.1 | 42.0 | 26.5 | 22.2 | 23.2 | 0.0 | 37.7 |
| V | 1.4 | 4.3 | 6.1 | 0.0 | 1.4 | 0.0 | 0.0 |
| A | 5.8 | 11.6 | 6.1 | 44.4 | 2.9 | 0.0 | 0.0 |
| C | 0.0 | 0.0 | 0.0 | 0.0 | 0.0 | 0.0 | 0.0 |
| D | 0.0 | 0.0 | 0.0 | 0.0 | 1.4 | 0.0 | 0.0 |
| E | 0.0 | 0.0 | 0.0 | 0.0 | 0.0 | 0.0 | 0.0 |
| F | 2.9 | 2.9 | 2.0 | 0.0 | 10.1 | 0.0 | 13.0 |
| G | 10.1 | 11.6 | 8.2 | 22.2 | 8.7 | 0.0 | 0.0 |
| I | 0.0 | 0.0 | 0.0 | 0.0 | 1.4 | 0.0 | 0.0 |
| K | 0.0 | 0.0 | 0.0 | 0.0 | 0.0 | 0.0 | 0.0 |
| L | 0.0 | 0.0 | 0.0 | 0.0 | 0.0 | 26.1 | 18.8 |
| M | 0.0 | 0.0 | 0.0 | 0.0 | 0.0 | 0.0 | 0.0 |
| N | 1.4 | 2.9 | 0.0 | 0.0 | 2.9 | 0.0 | 0.0 |
| W | 2.9 | 1.4 | 0.0 | 0.0 | 2.9 | 0.0 | 0.0 |

Results for Anti-CD40 Antibodies Selected from AL3

Amino Acid Frequency (%) in Each Position of Designed Diversity in VH CDR1

| Amino acid | IMGT number | | | | | |
|---|---|---|---|---|---|---|
| | 35 | 36 | 37 | 38 | 39 | 40 |
| H | 14.3 | 0.0 | 0.0 | 0.0 | 0.0 | 0.0 |
| R | 0.0 | 0.0 | 0.0 | 0.0 | 0.0 | 0.0 |
| S | 42.9 | 52.4 | 33.3 | 28.6 | 0.0 | 71.4 |
| T | 0.0 | 0.0 | 0.0 | 0.0 | 0.0 | 0.0 |
| P | 0.0 | 0.0 | 0.0 | 0.0 | 0.0 | 0.0 |
| Q | 0.0 | 0.0 | 0.0 | 0.0 | 0.0 | 0.0 |
| Y | 19.0 | 33.3 | 57.1 | 14.3 | 0.0 | 19.0 |
| V | 0.0 | 0.0 | 0.0 | 0.0 | 0.0 | 0.0 |
| A | 0.0 | 0.0 | 0.0 | 38.1 | 0.0 | 0.0 |
| C | 0.0 | 0.0 | 0.0 | 0.0 | 0.0 | 0.0 |
| D | 0.0 | 0.0 | 0.0 | 0.0 | 0.0 | 0.0 |
| E | 0.0 | 0.0 | 0.0 | 0.0 | 0.0 | 0.0 |
| F | 0.0 | 0.0 | 0.0 | 0.0 | 0.0 | 0.0 |
| G | 23.8 | 14.3 | 9.5 | 19.0 | 0.0 | 9.5 |
| I | 0.0 | 0.0 | 0.0 | 0.0 | 0.0 | 0.0 |
| K | 0.0 | 0.0 | 0.0 | 0.0 | 0.0 | 0.0 |
| L | 0.0 | 0.0 | 0.0 | 0.0 | 0.0 | 0.0 |
| M | 0.0 | 0.0 | 0.0 | 0.0 | 100.0 | 0.0 |
| N | 0.0 | 0.0 | 0.0 | 0.0 | 0.0 | 0.0 |
| W | 0.0 | 0.0 | 0.0 | 0.0 | 0.0 | 0.0 |

Amino Acid Frequency (%) in Each Position of Designed Diversity in VH CDR2

| Amino acid | IMGT number | | | | | | | | | |
|---|---|---|---|---|---|---|---|---|---|---|
| | 55 | 56 | 57 | 58 | 59 | 62 | 63 | 64 | 65 | 66 |
| H | 0.0 | 0.0 | 0.0 | 0.0 | 0.0 | 0.0 | 0.0 | 0.0 | 0.0 | 0.0 |
| R | 0.0 | 0.0 | 0.0 | 0.0 | 0.0 | 0.0 | 0.0 | 0.0 | 0.0 | 0.0 |
| S | 19.0 | 0.0 | 52.4 | 28.6 | 38.1 | 38.1 | 19.0 | 61.9 | 0.0 | 0.0 |
| T | 0.0 | 0.0 | 4.8 | 0.0 | 0.0 | 0.0 | 0.0 | 4.8 | 100.0 | 0.0 |
| P | 0.0 | 0.0 | 0.0 | 0.0 | 0.0 | 0.0 | 0.0 | 0.0 | 0.0 | 0.0 |
| Q | 0.0 | 0.0 | 0.0 | 0.0 | 0.0 | 0.0 | 0.0 | 0.0 | 0.0 | 0.0 |
| Y | 14.3 | 0.0 | 9.5 | 23.8 | 23.8 | 9.5 | 14.3 | 9.5 | 0.0 | 95.2 |
| V | 0.0 | 0.0 | 0.0 | 0.0 | 0.0 | 0.0 | 0.0 | 0.0 | 0.0 | 0.0 |
| A | 23.8 | 0.0 | 0.0 | 0.0 | 0.0 | 0.0 | 0.0 | 0.0 | 0.0 | 0.0 |
| C | 0.0 | 0.0 | 0.0 | 0.0 | 0.0 | 0.0 | 0.0 | 0.0 | 0.0 | 0.0 |
| D | 0.0 | 0.0 | 0.0 | 0.0 | 0.0 | 0.0 | 0.0 | 0.0 | 0.0 | 0.0 |
| E | 0.0 | 0.0 | 0.0 | 0.0 | 0.0 | 0.0 | 0.0 | 0.0 | 0.0 | 0.0 |
| F | 0.0 | 0.0 | 0.0 | 0.0 | 0.0 | 0.0 | 0.0 | 0.0 | 0.0 | 0.0 |
| G | 42.9 | 0.0 | 33.3 | 47.6 | 38.1 | 52.4 | 66.7 | 23.8 | 0.0 | 4.8 |
| I | 0.0 | 100.0 | 0.0 | 0.0 | 0.0 | 0.0 | 0.0 | 0.0 | 0.0 | 0.0 |
| K | 0.0 | 0.0 | 0.0 | 0.0 | 0.0 | 0.0 | 0.0 | 0.0 | 0.0 | 0.0 |
| L | 0.0 | 0.0 | 0.0 | 0.0 | 0.0 | 0.0 | 0.0 | 0.0 | 0.0 | 0.0 |
| M | 0.0 | 0.0 | 0.0 | 0.0 | 0.0 | 0.0 | 0.0 | 0.0 | 0.0 | 0.0 |
| N | 0.0 | 0.0 | 0.0 | 0.0 | 0.0 | 0.0 | 0.0 | 0.0 | 0.0 | 0.0 |
| W | 0.0 | 0.0 | 0.0 | 0.0 | 0.0 | 0.0 | 0.0 | 0.0 | 0.0 | 0.0 |

Amino Acid Frequency (%) in Each Position of Designed Diversity in VH CDR3

| Amino acid | IMGT number | | | | | | | |
|---|---|---|---|---|---|---|---|---|
| | 107 | 108 | 109 | 110 | 112 | 113 | 114 | 115 |
| H | 42.9 | 14.3 | 23.5 | 0.0 | 0.0 | 25.0 | 0.0 | 0.0 |
| R | 9.5 | 0.0 | 0.0 | 0.0 | 0.0 | 0.0 | 0.0 | 0.0 |
| S | 9.5 | 9.5 | 11.8 | 40.0 | 0.0 | 0.0 | 28.6 | 0.0 |
| T | 14.3 | 0.0 | 0.0 | 0.0 | 0.0 | 0.0 | 4.8 | 0.0 |
| P | 0.0 | 0.0 | 0.0 | 0.0 | 0.0 | 0.0 | 0.0 | 0.0 |
| Q | 0.0 | 0.0 | 0.0 | 0.0 | 0.0 | 0.0 | 0.0 | 0.0 |
| Y | 9.5 | 33.3 | 17.6 | 40.0 | 0.0 | 25.0 | 23.8 | 0.0 |
| V | 0.0 | 23.8 | 5.9 | 0.0 | 0.0 | 0.0 | 4.8 | 0.0 |
| A | 0.0 | 0.0 | 0.0 | 0.0 | 0.0 | 8.3 | 0.0 | 0.0 |
| C | 0.0 | 0.0 | 0.0 | 0.0 | 0.0 | 0.0 | 0.0 | 0.0 |
| D | 0.0 | 4.8 | 0.0 | 0.0 | 0.0 | 0.0 | 0.0 | 0.0 |
| E | 0.0 | 0.0 | 0.0 | 0.0 | 0.0 | 0.0 | 0.0 | 0.0 |

-continued

| Amino acid | IMGT number | | | | | | | |
|---|---|---|---|---|---|---|---|---|
| | 107 | 108 | 109 | 110 | 112 | 113 | 114 | 115 |
| F | 4.8 | 0.0 | 11.8 | 20.0 | 0.0 | 25.0 | 9.5 | 47.6 |
| G | 4.8 | 4.8 | 5.9 | 0.0 | 100.0 | 16.7 | 23.8 | 0.0 |
| I | 0.0 | 0.0 | 0.0 | 0.0 | 0.0 | 0.0 | 0.0 | 9.5 |
| K | 0.0 | 0.0 | 0.0 | 0.0 | 0.0 | 0.0 | 0.0 | 0.0 |
| L | 0.0 | 0.0 | 0.0 | 0.0 | 0.0 | 0.0 | 0.0 | 19.0 |
| M | 0.0 | 0.0 | 0.0 | 0.0 | 0.0 | 0.0 | 0.0 | 23.8 |
| N | 0.0 | 4.8 | 5.9 | 0.0 | 0.0 | 0.0 | 4.8 | 0.0 |
| W | 4.8 | 4.8 | 17.6 | 0.0 | 0.0 | 0.0 | 0.0 | 0.0 |

Amino Acid Frequency (%) in Each Position of Designed Diversity in VL CDR1

| Amino acid | IMGT number | | | |
|---|---|---|---|---|
| | 28 | 29 | 36 | 37 |
| H | 4.8 | 0.0 | 0.0 | 0.0 |
| R | 0.0 | 0.0 | 42.9 | 0.0 |
| S | 28.6 | 0.0 | 57.1 | 35.0 |
| T | 0.0 | 0.0 | 0.0 | 0.0 |
| P | 0.0 | 0.0 | 0.0 | 0.0 |
| Q | 0.0 | 0.0 | 0.0 | 0.0 |
| Y | 23.8 | 0.0 | 0.0 | 20.0 |
| V | 0.0 | 0.0 | 0.0 | 0.0 |
| A | 14.3 | 0.0 | 0.0 | 10.0 |
| C | 0.0 | 0.0 | 0.0 | 0.0 |
| D | 23.8 | 0.0 | 0.0 | 5.0 |
| E | 0.0 | 0.0 | 0.0 | 0.0 |
| F | 0.0 | 0.0 | 0.0 | 0.0 |
| G | 4.8 | 0.0 | 0.0 | 30.0 |
| I | 0.0 | 100.0 | 0.0 | 0.0 |
| K | 0.0 | 0.0 | 0.0 | 0.0 |
| L | 0.0 | 0.0 | 0.0 | 0.0 |
| M | 0.0 | 0.0 | 0.0 | 0.0 |
| N | 0.0 | 0.0 | 0.0 | 0.0 |
| W | 0.0 | 0.0 | 0.0 | 0.0 |

Amino Acid Frequency (%) in Each Position of Designed Diversity in VL CDR2

| Amino acid | IMGT number 56 |
|---|---|
| H | 0.0 |
| R | 0.0 |
| S | 0.0 |
| T | 0.0 |
| P | 0.0 |
| Q | 0.0 |
| Y | 0.0 |
| V | 0.0 |
| A | 95.2 |
| C | 0.0 |
| D | 0.0 |
| E | 0.0 |
| F | 0.0 |
| G | 4.8 |
| I | 0.0 |
| K | 0.0 |
| L | 0.0 |
| M | 0.0 |
| N | 0.0 |
| W | 0.0 |

Amino Acid Frequency (%) in Each Position of Designed Diversity in VL CDR3

| Amino acid | IMGT number | | | | | | |
|---|---|---|---|---|---|---|---|
| | 107 | 108 | 109 | 113 | 114 | 115 | 116 |
| H | 4.8 | 14.3 | 7.1 | 0.0 | 0.0 | 0.0 | 4.8 |
| R | 0.0 | 0.0 | 7.1 | 0.0 | 0.0 | 0.0 | 0.0 |
| S | 23.8 | 14.3 | 42.9 | 0.0 | 9.5 | 0.0 | 4.8 |
| T | 0.0 | 0.0 | 0.0 | 0.0 | 19.0 | 0.0 | 0.0 |
| P | 14.3 | 0.0 | 0.0 | 0.0 | 4.8 | 81.0 | 28.6 |
| Q | 0.0 | 0.0 | 0.0 | 0.0 | 0.0 | 0.0 | 0.0 |
| Y | 47.6 | 23.8 | 28.6 | 66.7 | 19.0 | 0.0 | 23.8 |
| V | 0.0 | 4.8 | 0.0 | 33.3 | 0.0 | 0.0 | 0.0 |
| A | 0.0 | 9.5 | 7.1 | 0.0 | 4.8 | 0.0 | 0.0 |
| C | 0.0 | 0.0 | 0.0 | 0.0 | 0.0 | 0.0 | 0.0 |
| D | 0.0 | 0.0 | 0.0 | 0.0 | 4.8 | 0.0 | 0.0 |
| E | 0.0 | 0.0 | 0.0 | 0.0 | 0.0 | 0.0 | 0.0 |
| F | 0.0 | 0.0 | 0.0 | 0.0 | 9.5 | 0.0 | 4.8 |
| G | 4.8 | 33.3 | 7.1 | 0.0 | 9.5 | 0.0 | 0.0 |
| I | 0.0 | 0.0 | 0.0 | 0.0 | 0.0 | 0.0 | 0.0 |
| K | 0.0 | 0.0 | 0.0 | 0.0 | 0.0 | 0.0 | 0.0 |
| L | 0.0 | 0.0 | 0.0 | 0.0 | 0.0 | 19.0 | 33.3 |
| M | 0.0 | 0.0 | 0.0 | 0.0 | 0.0 | 0.0 | 0.0 |
| N | 0.0 | 0.0 | 0.0 | 0.0 | 4.8 | 0.0 | 0.0 |
| W | 4.8 | 0.0 | 0.0 | 0.0 | 14.3 | 0.0 | 0.0 |

Results for Anti-LTBR Antibodies Selected from AL1
Amino Acid Frequency (%) in Each Position of Designed Diversity in VH CDR1

| Amino acid | IMGT number | | | | | |
|---|---|---|---|---|---|---|
| | 35 | 36 | 37 | 38 | 39 | 40 |
| H | 0 | 0 | 0 | 0 | 0 | 0 |
| R | 0 | 0 | 0 | 0 | 0 | 0 |
| S | 33 | 100 | 33 | 33 | 0 | 67 |
| T | 0 | 0 | 0 | 0 | 0 | 0 |
| P | 0 | 0 | 0 | 0 | 0 | 0 |
| Q | 0 | 0 | 0 | 0 | 0 | 0 |
| Y | 0 | 0 | 67 | 33 | 0 | 33 |
| V | 0 | 0 | 0 | 0 | 0 | 0 |
| A | 0 | 0 | 0 | 33 | 0 | 0 |
| C | 0 | 0 | 0 | 0 | 0 | 0 |
| D | 0 | 0 | 0 | 0 | 0 | 0 |
| E | 0 | 0 | 0 | 0 | 0 | 0 |
| F | 0 | 0 | 0 | 0 | 0 | 0 |
| G | 67 | 0 | 0 | 0 | 0 | 0 |
| I | 0 | 0 | 0 | 0 | 0 | 0 |
| K | 0 | 0 | 0 | 0 | 0 | 0 |
| L | 0 | 0 | 0 | 0 | 0 | 0 |
| M | 0 | 0 | 0 | 0 | 100 | 0 |
| N | 0 | 0 | 0 | 0 | 0 | 0 |
| W | 0 | 0 | 0 | 0 | 0 | 0 |

Amino Acid Frequency (%) in Each Position of Designed Diversity in VH CDR2

| Amino acid | IMGT number | | | | | | | | | |
|---|---|---|---|---|---|---|---|---|---|---|
| | 55 | 56 | 57 | 58 | 59 | 62 | 63 | 64 | 65 | 66 |
| H | 0 | 0 | 0 | 0 | 0 | 0 | 0 | 0 | 0 | 0 |
| R | 0 | 0 | 0 | 0 | 0 | 0 | 0 | 0 | 0 | 0 |
| S | 67 | 0 | 67 | 33 | 67 | 33 | 33 | 67 | 0 | 67 |
| T | 0 | 0 | 0 | 0 | 0 | 0 | 0 | 0 | 100 | 0 |
| P | 0 | 0 | 0 | 0 | 0 | 0 | 0 | 0 | 0 | 0 |
| Q | 0 | 0 | 0 | 0 | 0 | 0 | 0 | 0 | 0 | 0 |
| Y | 0 | 0 | 33 | 0 | 33 | 33 | 0 | 0 | 0 | 33 |
| V | 0 | 0 | 0 | 0 | 0 | 0 | 0 | 0 | 0 | 0 |
| A | 33 | 0 | 0 | 0 | 0 | 0 | 0 | 0 | 0 | 0 |
| C | 0 | 0 | 0 | 0 | 0 | 0 | 0 | 0 | 0 | 0 |
| D | 0 | 0 | 0 | 0 | 0 | 0 | 0 | 0 | 0 | 0 |

-continued

Amino Acid Frequency (%) in Each Position of Designed Diversity in VH CDR2

| Amino acid | IMGT number | | | | | | | | | |
|---|---|---|---|---|---|---|---|---|---|---|
| | 55 | 56 | 57 | 58 | 59 | 62 | 63 | 64 | 65 | 66 |
| E | 0 | 0 | 0 | 0 | 0 | 0 | 0 | 0 | 0 | 0 |
| F | 0 | 0 | 0 | 0 | 0 | 0 | 0 | 0 | 0 | 0 |
| G | 0 | 0 | 0 | 67 | 0 | 33 | 67 | 33 | 0 | 0 |
| I | 0 | 100 | 0 | 0 | 0 | 0 | 0 | 0 | 0 | 0 |
| K | 0 | 0 | 0 | 0 | 0 | 0 | 0 | 0 | 0 | 0 |
| L | 0 | 0 | 0 | 0 | 0 | 0 | 0 | 0 | 0 | 0 |
| M | 0 | 0 | 0 | 0 | 0 | 0 | 0 | 0 | 0 | 0 |
| N | 0 | 0 | 0 | 0 | 0 | 0 | 0 | 0 | 0 | 0 |
| W | 0 | 0 | 0 | 0 | 0 | 0 | 0 | 0 | 0 | 0 |

Amino Acid Frequency (%) in Each Position of Designed Diversity in VH CDR3

| Amino acid | IMGT number | | | | | | |
|---|---|---|---|---|---|---|---|
| | 107 | 108 | 109 | 110 | 113 | 114 | 115 |
| H | 0 | 0 | 0 | 0 | 0 | 0 | 0 |
| R | 0 | 0 | 0 | 0 | 0 | 0 | 0 |
| S | 0 | 0 | 0 | 0 | 0 | 0 | 0 |
| T | 0 | 0 | 0 | 0 | 0 | 0 | 0 |
| P | 0 | 0 | 0 | 0 | 0 | 0 | 0 |
| Q | 0 | 0 | 0 | 0 | 0 | 0 | 0 |
| Y | 33 | 67 | 50 | 0 | 0 | 100 | 0 |
| V | 0 | 0 | 0 | 0 | 0 | 0 | 0 |
| A | 0 | 33 | 0 | 0 | 0 | 0 | 0 |
| C | 0 | 0 | 0 | 0 | 0 | 0 | 0 |
| D | 0 | 0 | 0 | 0 | 50 | 0 | 0 |
| E | 0 | 0 | 0 | 0 | 0 | 0 | 0 |
| F | 0 | 0 | 0 | 0 | 0 | 0 | 33 |
| G | 67 | 0 | 0 | 50 | 0 | 0 | 0 |
| I | 0 | 0 | 0 | 0 | 0 | 0 | 0 |
| K | 0 | 0 | 0 | 0 | 0 | 0 | 0 |
| L | 0 | 0 | 0 | 0 | 0 | 0 | 33 |
| M | 0 | 0 | 0 | 0 | 0 | 0 | 33 |
| N | 0 | 0 | 0 | 0 | 0 | 0 | 0 |
| W | 0 | 0 | 50 | 50 | 50 | 0 | 0 |

Amino Acid Frequency (%) in Each Position of Designed Diversity in VL CDR3

| Amino acid | IMGT number | | | | | |
|---|---|---|---|---|---|---|
| | 107 | 108 | 109 | 114 | 115 | 116 |
| H | 0 | 0 | 0 | 0 | 0 | 0 |
| R | 0 | 0 | 0 | 0 | 0 | 0 |
| S | 0 | 0 | 0 | 0 | 0 | 0 |
| T | 0 | 0 | 0 | 0 | 0 | 0 |
| P | 0 | 0 | 0 | 0 | 67 | 33 |
| Q | 0 | 0 | 0 | 0 | 0 | 0 |
| Y | 33 | 33 | 0 | 33 | 0 | 0 |
| V | 0 | 0 | 0 | 0 | 0 | 0 |
| A | 33 | 0 | 0 | 0 | 0 | 0 |
| C | 0 | 0 | 0 | 0 | 0 | 0 |
| D | 0 | 0 | 0 | 33 | 0 | 0 |
| E | 0 | 0 | 0 | 0 | 0 | 0 |
| F | 0 | 0 | 0 | 33 | 0 | 33 |
| G | 33 | 0 | 0 | 0 | 0 | 0 |
| I | 0 | 0 | 0 | 0 | 0 | 0 |
| K | 0 | 0 | 0 | 0 | 0 | 0 |
| L | 0 | 0 | 0 | 0 | 33 | 33 |
| M | 0 | 0 | 0 | 0 | 0 | 0 |
| N | 0 | 0 | 0 | 0 | 0 | 0 |
| W | 0 | 67 | 100 | 0 | 0 | 0 |

Example 4

Selection Based on Further Target Antigen

Phage display libraries of category AL1, and a pooled mixture of AL2 and 3 (AL2/3) in ScFv format were tested separately in selection experiments using the antigen Green fluorescent protein, GFP.

The general procedure for selecting the binding antibody clones against the target GFP were as described in Example 2 for the target CD40. The non-biotinylated GFP protein was purchased from BioSite (#PAT-80285-1).

Screening and Sequence for Determination of scFv Antibody Clones Specific for GFP Screening for antibody clones binding to GFP and subsequent sequencing were performed. GFP binders were identified by comparing binding to target (GFP) and non-target (Orencia) coated plates in an ELISA assay at a single dilution of scFv antibody displayed on phage. The protocol for the ELISA assays was as described for CD40 binders in Example 2.

The identified antibody clones were sequenced and their CDRs (complementary determining regions) were determined. The sequences of the total number of identified antibody clones versus the number of identified unique sequences encoding antibody clones were analysed. The results are shown in the following table. All libraries tested generated specific binding antibody clones to GFP-antigen.

| Library | Unique clones (% of total sequenced clones) | Confirmed GFP binding in ELISA |
|---|---|---|
| AL1 | 14 (45%) | 10% |
| AL2/3 | 44 (53%) | 100% |

In mixed library AL2/3 the confirmed specific binding by the selected antibody clones to GFP was 100% as shown by ELISA in secondary (confirmatory) test.

Analysis of Amino Acid Preferences, Sequence Diversity and Lengths

The amino acid preferences and sequence diversity of antibody clones binding to GFP from libraries AL1, and pooled libraries AL2/3 were further analysed. Selection against human GFP was performed as described above. The binding antibody clones were obtained by phage display selection and screened using ELISA. The isolated antibody clones were subsequently sequenced.

The positions of the CDR regions were determined using the IMGT system. Alignment tools are available at www.imgt.org. The frequency of each amino acid in the VH CDR3 of each antibody was calculated. The average amino acid frequencies for the antibodies from each library are shown in FIG. 4.

Figure 4:
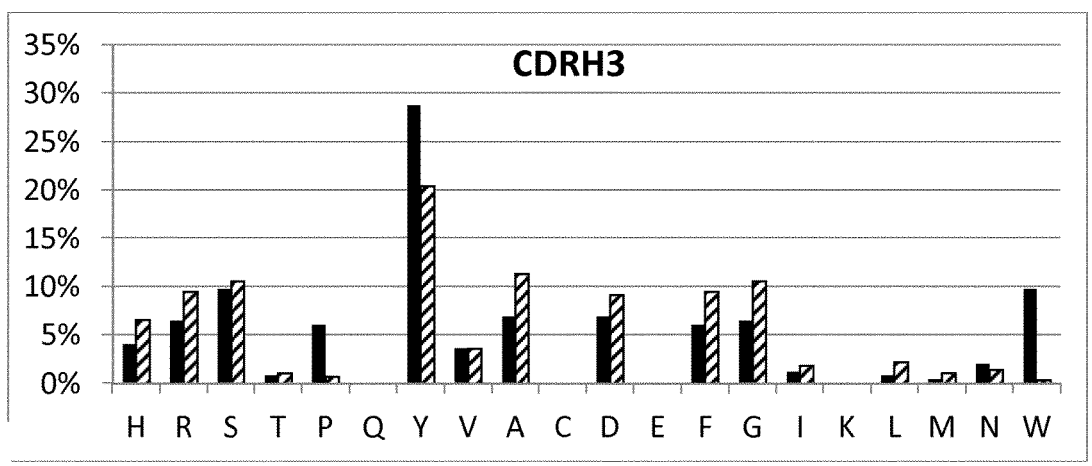
FIG. 4 shows the average overall frequency of each amino acid in the VH CDR3 loops for isolated anti-GFP antibody clones from library AL1 (filled bars), and pooled libraries AL2/AL3 (hatched bars).

In FIG. 4 the amino acid distributions of the VH CDR3 loops of antibody clones selected for GFP binding is shown. The VH CDR3 loops contain elevated tyrosine, glycine, serine, alanine, arginine, and aspartic acid. In contrast, threonine, valine, isoleucine, leucine, methionine, asparagine, and tryptophan are lowered. Cysteine, glutamic acid, proline, and lysine are designed to be absent in the VH CDR3 loop.

The observed amino acid distribution match demonstrated beneficial VH CDR3 amino acid diversity, with high levels of tyrosine, glycine, serine, and, or alanine, and low levels of all other amino acids. The frequency of functional binders isolated from the library will increase due to the beneficial amino acid profile, which supports high molecular recognition, optimal conformational diversity, charge, and structural integrity of the CDR loop.

The library design of the present invention results in lower tryptophan content in pooled AL2/3, compared to AL1, and the histidine content in pooled AL2/3 relative to AL1 is elevated. Further, the mean frequency of histidine in the VH CDR3 loops of antibodies selected from library AL3 is high relative to the natural repertoire. This is consistent with the designed high level of histidine for VH CDR3 of AL3. High histidine levels are advantageous when selecting for antibodies with preferential binding at low pH, which will be used to treat cancers since the pH in a tumour microenvironment in vivo is significantly more acidic than that of healthy tissues.

The loop lengths of VH CDR3 of each selected anti-GFP antibody from AL1 and AL2/3 were also analysed. The average lengths of the VH CDR3 loops of antibody clones binding to GFP isolated from the libraries were determined. For AL1, the average length was 17 (STDEV 4.5). For AL2/3, the average length was 11 (STDEV 1.6). The VH CDR3 lengths are shorter than those typically obtained from naturally occurring human IgG, particularly for AL2/3.

Summary of Examples

Examples 1 to 4 demonstrate that the libraries designed in accordance with the present invention, which are highly diverse libraries with minimal structural perturbations, are capable of generating high proportions of unique antibody binders with satisfactory affinities. The antibodies isolated from the libraries of the invention typically in fact have affinity in the nanomolar range.

The design of the amino acid composition of the VH CDR3 and VL CDR3 loops in all of the libraries of the invention results in binding domains characterised by beneficial amino acid profiles. In particular, as is demonstrated in FIGS. 3A and 4 (and the accompanying analysis above), for libraries of the invention, tyrosine is the dominating amino acid in the VH CDR3 loop. The levels of the amino acids, serine, alanine, glycine, arginine, and asparatic acid are also elevated in the VH CDR3 loop, whereas cysteine, glutamic acid, lysine, and glutamine are absent. These amino acid frequencies are advantageous, because tyrosine is known to have a dominating role in loop structure and antigen recognition, glycine contributes conformational flexibility to the loop structure, and serine and alanine are favorable for loop conformation due to their small and neutral side chains. By contrast, cysteine, glutamic acid, lysine, and glutamine are unfavourable for loop confirmation because they are large and/or highly charged.

In addition, the library designs for categories AL2 and AL3 (and pooled mixtures thereof) are shown to be particularly advantageous. The designs of library categories AL2 and AL3 result in shorter average VH CDR3 loop length (see Example 4) as well as a lower frequency of tryptophan and an elevated frequency of histidine in the VH CDR3 loops (see FIGS. 3A and 4), when compared to libraries of category AL1. This is significant because it was observed that non-specific binders isolated from a library of category AL1 typically contained a longer VH CDR3 loop with a relatively high proportion of tryptophan. Thus the library designs for categories AL2 and AL3 (and pooled mixtures thereof) result in a higher number and proportion of specific binders.

The invention claimed is:

1. A library of antibody molecules, wherein each antibody molecules comprises
   (i) a VH domain consisting of VH CDR1, CDR2, CDR3 and framework regions, wherein the VH domain amino acid sequence is a human germline antibody heavy chain sequence in which:
      (a) each solvent accessible residue in VH CDR1 and CDR2 is independently substituted with an amino acid selected from tyrosine, serine and glycine, wherein each of tyrosine, serine and glycine is equally preferred;
      (b) the VH CDR3 consists of between 8 and 17 amino acids;
      (c) each solvent accessible residue in VH CDR3 is independently substituted with an amino acid selected from tyrosine, serine, glycine, alanine, phenylalanine, tryptophan, histidine, proline, valine, aspartate, asparagines, threonine and arginine in the following relative order of preference: 25% Tyr, 15% Ser, 20% Gly, 5% Ala, 5% Phe, 5% Trp, 5% His, 5% Pro, 5% Val, 3% Asp, 3% Asn, 3% Thr, 1% Arg; and
      (d) the residue at position 115 in VH CDR3 is independently substituted with an amino acid selected from phenylalanine, isoleucine, leucine and methionine, wherein each of phenylalanine, isoleucine, leucine and methionine is equally preferred; and
   (ii) a VL domain consisting of VL CDR1, CDR2, CDR3 and framework regions, wherein the VL domain amino acid sequence is a human germline antibody light chain sequence in which:
      (a) the VL CDR3 consists of between 8 and 12 amino acids;
      (b) each solvent accessible residue in VL CDR3 is independently substituted with an amino acid selected from tyrosine, serine, glycine, alanine, phenylalanine, tryptophan, histidine, proline, valine, aspartate, asparagines, threonine and arginine in the following relative order of preference: 25% Tyr, 15% Ser, 20% Gly, 5% Ala, 5% Phe, 5% Trp, 5% His, 5% Pro, 5% Val, 3% Asp, 3% Asn, 3% Thr, 1% Arg;
      (c) the residue at position 115 in VL CDR3 is independently substituted with an amino acid selected from phenylalanine and leucine, wherein each of phenylalanine leucine is equally preferred; and
      (d) the residue at position 116 in VL CDR3 is independently substituted with an amino acid selected from histidine, proline, leucine, tyrosine, serine and phenylalanine, wherein each of histidine, proline, leucine, tyrosine, serine and phenylalanine is equally preferred;
   wherein the positions of the amino acid residues are defined in accordance with the IMGT numbering system; and
   wherein:
      the solvent accessible residues in VH CDR1 are at positions 35, 36, 37, 38 and 40; and/or
      the solvent accessible residues in VH CDR2 are at positions 55, 57, 58, 59, 62, 63, 64 and 66; and/or
      the solvent accessible residues in VH CDR3 are at positions 107, 108, 109, 110, 111, 111.1, 111.2, 112.2, 112.1, 112, 113 and 114, or positions 107, 108, 109, 110, 111, 111.1, 111.2, 111.3, 111.4, 112.5, 112.4, 112.3, 112.2, 112.1, 112, 113 and 114; and/or
      the solvent accessible residues in VL CDR3 are at positions 107, 108, 109, 110, 112, 113 and 114.

2. A library of antibody molecules in which a proportion of the antibody molecules are each as defined in claim 1 and a proportion of the antibody molecules are each defined as comprising:
   (i) a VH domain consisting of VH CDR1, CDR2, CDR3 and framework regions, wherein the VH domain amino acid sequence is a human germline antibody heavy chain sequence in which:
      (a) each solvent accessible residue in VH CDR1 and CDR2 is independently substituted with an amino acid selected from tyrosine, serine and glycine, wherein each of tyrosine, serine and glycine is equally preferred;
      (b) the VH CDR3 consists of between 8 and 17 amino acids;
      (c) each solvent accessible residue in VH CDR3 is independently substituted with an amino acid selected from tyrosine, glycine, serine, tryptophan, alanine, phenylalanine, histidine, proline, valine, aspartate, asparagines, threonine and arginine, in the following relative order of preference 20% Tyr, 15% Gly, 15% Ser, 5% Trp, 5% Ala, 5% Phe, 15% His, 5% Pro, 5% Val, 3% Asp, 3% Asn, 3% Thr, 1% Arg; and
      (d) the residue at position 115 of VH CDR3 is independently substituted with an amino acid selected from phenylalanine, isoleucine, leucine and methionine, wherein each of phenylalanine, isoleucine, leucine and methionine is equally preferred; and
   (ii) a VL domain consisting of VL CDR1, CDR2, CDR3 and framework regions, wherein the VL domain amino acid sequence is a human germline antibody light chain sequence in which:
      (e) the residues at positions 28 and 37 in VL CDR1 are each independently substituted with an amino acid selected from tyrosine, serine, glycine, asparagine and alanine, wherein each of tyrosine, serine, glycine, asparagine and alanine is equally preferred;
      (f) the residue at position 36 in VL CDR1 is independently substituted with an amino acid selected from serine and arginine, wherein each of serine and arginine is equally preferred;
      (g) the residue in position 56 of VL CDR2 is independently substituted with an amino acid selected from tyrosine, serine, glycine, asparagine and alanine, wherein each of tyrosine, serine, glycine, asparagine and alanine is equally preferred;
      (h) the VL CDR3 consists of between 8 and 12 amino acids;
      (i) each solvent accessible residue in VL CDR3 is independently substituted with an amino acid selected from tyrosine, glycine, serine, tryptophan, alanine, phenylalanine, histidine, proline, valine, aspartate, asparagines, threonine and arginine, in the following relative order of preference: 25% Tyr, 20% Gly, 15% Ser, 5% Trp, 5% Ala, 5% Phe, 5% His, 5% Pro, 5% Val, 3% Asp, 3% Asn, 3% Thr, 1% Arg;
      (j) the residue at position 115 in VL CDR3 is independently substituted with an amino acid selected from phenylalanine and leucine, wherein each of phenylalanine and leucine is equally preferred; and
      (k) the residue at position 116 in VL CDR3 is independently substituted with an amino acid selected from histidine, proline, leucine, tyrosine, serine and phenylalanine, wherein each of histidine, proline, leucine, tyrosine, serine and phenylalanine is equally preferred.

3. The library according to claim 1, wherein the human germline antibody heavy chain sequence comprises the IgHV3-23 sequence (SEQ ID NO: 1) linked to the Jµregion 00256 sequence (SEQ ID NO: 2); and/or the human germline antibody light chain sequence comprises the IgKV1-39 sequence (SEQ ID NO: 4) linked to JK delta region 00242 sequence (SEQ ID NO: 5).

4. The library according to claim 1, wherein the VH domain sequence is as defined in Table 1 and/or the VL domain sequence is as defined in Table 2.

5. The library according to claim 1, wherein each antibody molecule is an scFv molecule, in which the VH domain and the VL domain are joined by a linker.

6. The library according to claim 1, wherein each antibody molecule is fused to a coat protein of a filamentous bacteriophage.

7. The library according to claim 6, wherein the antibody molecules are displayed on filamentous bacteriophage.

\* \* \* \* \*